United States Patent
Brogdon et al.

(10) Patent No.: US 10,662,247 B2
(45) Date of Patent: *May 26, 2020

(54) COMPOSITIONS AND METHODS OF USE FOR AUGMENTED IMMUNE RESPONSE AND CANCER THERAPY

(71) Applicant: NOVARTIS AG, Basel (CH)

(72) Inventors: Jennifer Brogdon, Sudbury, MA (US); Daniela Cipolletta, Arlington, MA (US); Glenn Dranoff, Lexington, MA (US); Deborah A. Knee, Del Mar, CA (US); Fei Wang, San Diego, CA (US)

(73) Assignee: Novartis AG, Basel (CH)

( * ) Notice: Subject to any disclaimer, the term of this patent is extended or adjusted under 35 U.S.C. 154(b) by 191 days.

This patent is subject to a terminal disclaimer.

(21) Appl. No.: 15/517,867

(22) PCT Filed: Oct. 8, 2015

(86) PCT No.: PCT/US2015/054775
§ 371 (c)(1),
(2) Date: Apr. 7, 2017

(87) PCT Pub. No.: WO2016/057846
PCT Pub. Date: Apr. 14, 2016

(65) Prior Publication Data
US 2017/0306037 A1    Oct. 26, 2017

Related U.S. Application Data

(60) Provisional application No. 62/061,644, filed on Oct. 8, 2014, provisional application No. 62/198,673, filed on Jul. 29, 2015, provisional application No. 62/220,764, filed on Sep. 18, 2015.

(51) Int. Cl.
C07K 16/28    (2006.01)
A61K 39/00    (2006.01)
A61K 45/06    (2006.01)

(52) U.S. Cl.
CPC .......... *C07K 16/2878* (2013.01); *A61K 39/00* (2013.01); *A61K 45/06* (2013.01); *C07K 16/2818* (2013.01); *A61K 2039/505* (2013.01); *A61K 2039/507* (2013.01); *C07K 2317/24* (2013.01); *C07K 2317/33* (2013.01); *C07K 2317/51* (2013.01); *C07K 2317/515* (2013.01); *C07K 2317/56* (2013.01); *C07K 2317/567* (2013.01); *C07K 2317/732* (2013.01); *C07K 2317/74* (2013.01); *C07K 2317/75* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | |
|---|---|---|
| 6,165,476 A | 12/2000 | Strom |
| 6,503,184 B1 | 1/2003 | Ni |
| 7,612,181 B2 | 11/2009 | Ghayur |
| 7,799,902 B2 | 9/2010 | Garber |
| 7,812,135 B2 | 10/2010 | Rosenzweig |
| 7,947,271 B2 | 5/2011 | Garber |
| 8,084,026 B2 | 12/2011 | Glaser |
| 8,388,967 B2 | 3/2013 | Rosenzweig |
| 8,409,577 B2 | 4/2013 | Thompson |
| 8,709,424 B2 | 4/2014 | Presta |
| 2002/0150993 A1 | 10/2002 | Goddard |
| 2003/0133936 A1 | 7/2003 | McHugh |
| 2004/0242847 A1 | 12/2004 | Tsunoda |
| 2005/0014224 A1 | 1/2005 | McHugh |
| 2005/0069521 A1 | 3/2005 | Way |
| 2005/0069983 A1 | 3/2005 | Goddard |
| 2006/0002932 A1 | 1/2006 | Vieweg |
| 2006/0051350 A1 | 3/2006 | Lobato Van Esch |
| 2006/0099171 A1 | 5/2006 | Tone |
| 2006/0141573 A1 | 6/2006 | Goddard |
| 2007/0098719 A1 | 5/2007 | Rosenzweig |
| 2007/0154476 A1 | 7/2007 | Garber |

(Continued)

FOREIGN PATENT DOCUMENTS

| | | |
|---|---|---|
| CL | 201600460 | 3/2017 |
| CL | 201603136 | 8/2017 |

(Continued)

OTHER PUBLICATIONS

Tame (J. Comput. Aided Mol. Des. Mar. 1999; 13 (2): 99-108).*
Dixon (Proteins. 1997; Suppl 1: 198-204).*
Lensink et al. (Proteins. 2007; 69: 704-718).*
Gussow et al. (Methods in Enzymology. 1991; 203: 99-121).*
Karu, A., et al., "Recombinant Antibody Technology", ILAR J. 37(3):132-141. 1995.
Brown, et al., "Tolerance to Single, but Not Multiple, Amino Acid Replacements in Antibody Vh CDR2", The Journal of Immunology, 156:3285-3291. 1996.
Murray et al., Human Biochemistry, Mir, 1:34. 1993.

(Continued)

*Primary Examiner* — Brad Duffy
(74) *Attorney, Agent, or Firm* — Kun Wang; Genomics Institute of the Novartis Research Foundation

(57) ABSTRACT

The present invention provides antibody compositions, including, e.g., antibodies, engineered antibodies and antibody fragments that bind to a tumor necrosis factor receptor superfamily member (i.e., 18). Provided compositions are useful in enhancing CD4+ and CD8+ T cell responses, and in the treatment, amelioration and prevention of diseases that can be counteracted with an augmented immune response, e.g., cancers. Also provided in the invention are polynucleotides and vectors that encode such molecules and host cells that harbor the polynucleotides or vectors; as well as pharmaceutical compositions that comprise such molecules and methods of use thereof.

23 Claims, 14 Drawing Sheets
Specification includes a Sequence Listing.

(56) References Cited

U.S. PATENT DOCUMENTS

| | | |
|---|---|---|
| 2008/0221016 A1 | 9/2008 | McHugh |
| 2009/0130105 A1 | 5/2009 | Hariharan |
| 2009/0136494 A1 | 5/2009 | Rosenzweig |
| 2009/0155255 A1 | 6/2009 | MacLaren |
| 2009/0162380 A1 | 6/2009 | Glaser |
| 2009/0175867 A1 | 7/2009 | Ledbetter |
| 2009/0214533 A1 | 8/2009 | Clynes |
| 2009/0232811 A1 | 9/2009 | Klein |
| 2010/0010195 A1 | 1/2010 | Goddard |
| 2010/0069614 A1 | 3/2010 | Logtenberg |
| 2010/0266542 A1 | 10/2010 | Bailly |
| 2010/0316645 A1 | 12/2010 | Klein |
| 2010/0322934 A1 | 12/2010 | Klein |
| 2011/0033483 A1 | 2/2011 | Thompson |
| 2011/0059109 A1 | 3/2011 | Rosenzweig |
| 2011/0076722 A1 | 3/2011 | Takahashi |
| 2011/0177070 A1 | 7/2011 | Misher |
| 2011/0212086 A1 | 9/2011 | Roberts |
| 2012/0034245 A9 | 2/2012 | Thompson |
| 2012/0189639 A1 | 7/2012 | Presta |
| 2012/0282184 A1 | 11/2012 | Nolan |
| 2013/0039911 A1 | 2/2013 | Ravi |
| 2013/0071403 A1 | 3/2013 | Doukas |
| 2013/0095097 A1 | 4/2013 | Tan |
| 2013/0108641 A1 | 5/2013 | Dabdoubi |
| 2013/0183321 A1 | 7/2013 | Ponte |
| 2013/0336977 A1 | 12/2013 | Ledbetter |
| 2014/0065152 A1 | 3/2014 | Kwon |
| 2014/0072566 A1 | 3/2014 | Kwon |
| 2014/0127203 A1 | 5/2014 | Thompson |
| 2014/0141022 A1 | 5/2014 | Thompson |
| 2014/0154250 A1 | 6/2014 | Ledbetter |
| 2014/0154252 A1 | 6/2014 | Ledbetter |
| 2014/0294759 A1 | 10/2014 | Chu |
| 2014/0294825 A1 | 10/2014 | Tsurushita |

FOREIGN PATENT DOCUMENTS

| | | |
|---|---|---|
| CL | 2018001369 | 7/2018 |
| EP | 2332992 A1 | 6/2011 |
| EP | 2343320 A1 | 7/2011 |
| EP | 2418223 A2 | 2/2012 |
| EP | 1866339B1 B1 | 5/2013 |
| JP | 2008-278814 A | 11/2008 |
| JP | 2013-503632 A | 2/2013 |
| WO | 1998006842 A1 | 2/1998 |
| WO | 9940196 A1 | 8/1999 |
| WO | 1999051638 A1 | 10/1999 |
| WO | 2000005374 A2 | 2/2000 |
| WO | 2000009143 A1 | 2/2000 |
| WO | 200032778 A2 | 6/2000 |
| WO | 200053753 A2 | 9/2000 |
| WO | 200053757 A2 | 9/2000 |
| WO | 200053758 A2 | 9/2000 |
| WO | 200073452 A2 | 12/2000 |
| WO | 2001003720 A2 | 1/2001 |
| WO | 2001058957 A2 | 8/2001 |
| WO | 0208293 A2 | 1/2002 |
| WO | 2004058191 A2 | 7/2004 |
| WO | 2004060319 A2 | 7/2004 |
| WO | 2004107618 A2 | 12/2004 |
| WO | 2005092927 A1 | 10/2005 |
| WO | 2005115451 A2 | 12/2005 |
| WO | 2006074399 A2 | 7/2006 |
| WO | 2006083289 A2 | 8/2006 |
| WO | 2006105021 A2 | 10/2006 |
| WO | 06117782 A2 | 11/2006 |
| WO | 2006132272 A1 | 12/2006 |
| WO | 2007044887 A2 | 4/2007 |
| WO | 2007048037 A2 | 4/2007 |
| WO | 2007109254 A2 | 9/2007 |
| WO | 2007133822 A1 | 11/2007 |
| WO | 2007146968 A2 | 12/2007 |
| WO | 2009009116 A2 | 1/2009 |
| WO | 2009018386 A1 | 2/2009 |
| WO | 2010003118 A1 | 1/2010 |
| WO | 2010028798 A1 | 3/2010 |
| WO | 2011028683 A1 | 3/2011 |
| WO | 11051726 A2 | 5/2011 |
| WO | 11071871 A1 | 6/2011 |
| WO | 2011090754 A1 | 7/2011 |
| WO | 11109789 A2 | 9/2011 |
| WO | 2012025525 A1 | 3/2012 |
| WO | 2012025530 A1 | 3/2012 |
| WO | 2012088461 A2 | 6/2012 |
| WO | 2012158818 A2 | 11/2012 |
| WO | 2012178137 A1 | 12/2012 |
| WO | 2013039954 A1 | 3/2013 |
| WO | 2013043569 A1 | 3/2013 |
| WO | 13055745 A2 | 4/2013 |
| WO | 2013049254 A1 | 4/2013 |
| WO | 2013142255 A2 | 9/2013 |
| WO | 2014012479 A1 | 1/2014 |
| WO | 2014022592 A1 | 2/2014 |
| WO | 2014089113 A1 | 6/2014 |
| WO | 2014116846 A2 | 7/2014 |
| WO | 2014145907 A1 | 9/2014 |
| WO | 2015031667 A2 | 3/2015 |

OTHER PUBLICATIONS

McHugh, et al., "CD4+CD25+ Immunoregulatory T Cells: Gene Expression Analysis Reveals a Functional Role for the Glucocorticoid-Induced TNF Receptor", Immunity, 16:311-323. 2002.

Cohen, Adam D., et al., "Agonist Anti-GITR Antibody Enhances Vaccine-Induced CD8+ T-Cell Responses and Tumor Immunity", Cancer Research, 66(9):4904-4912. (2006).

Ko, Kuibeom et al., "Treatment of advanced tumors with agonistic anti-GITR mAb and its effects on tumor-infiltrating Foxp3+CD25+ CD4+ regulatory T cells", The Journal of Experimental Medicine, 202(7):885-891. (2005).

\* cited by examiner

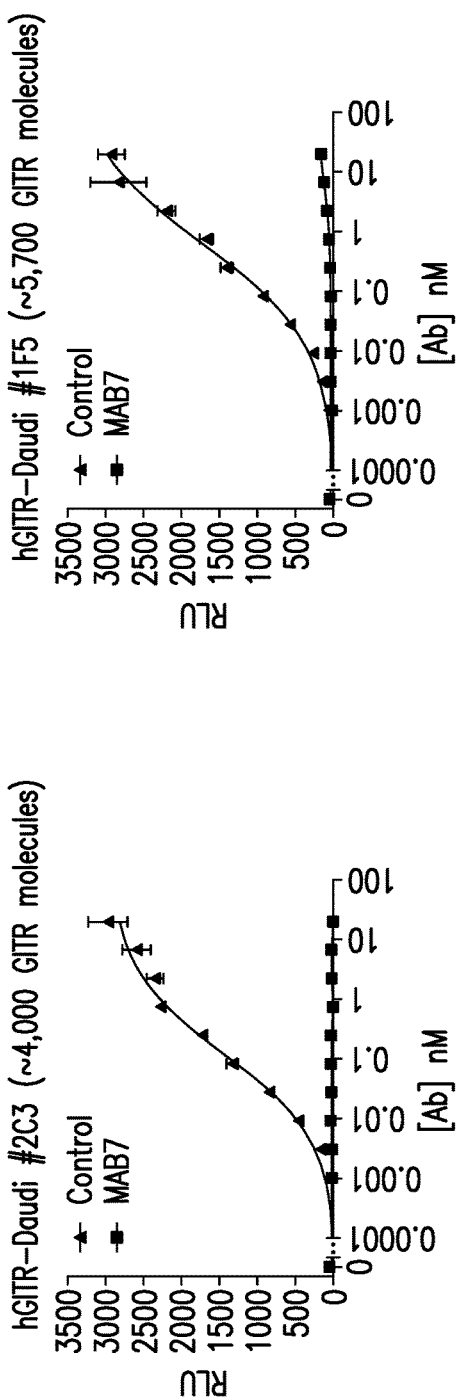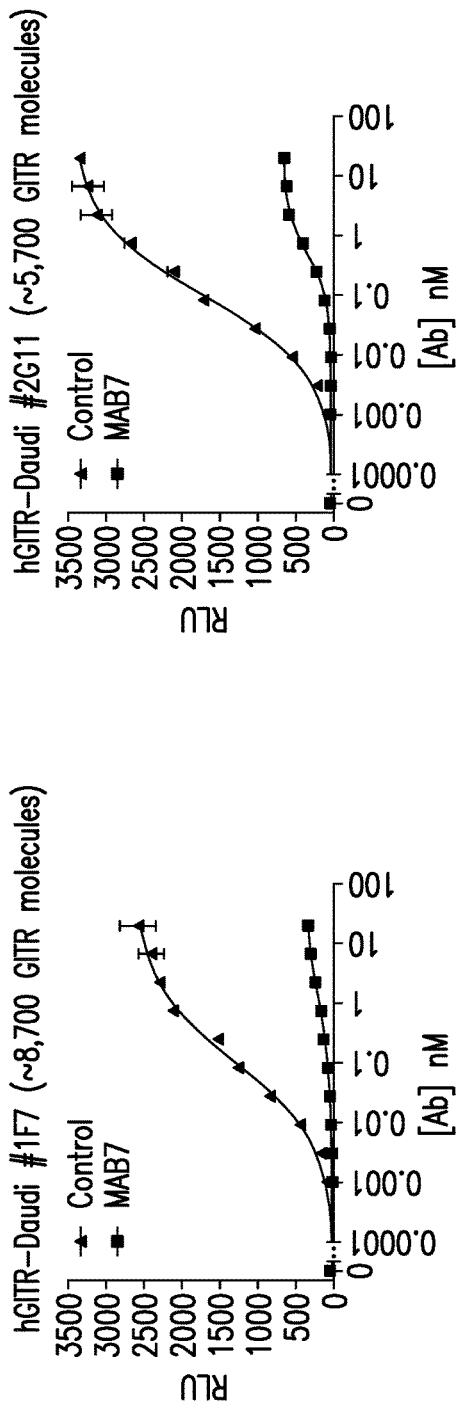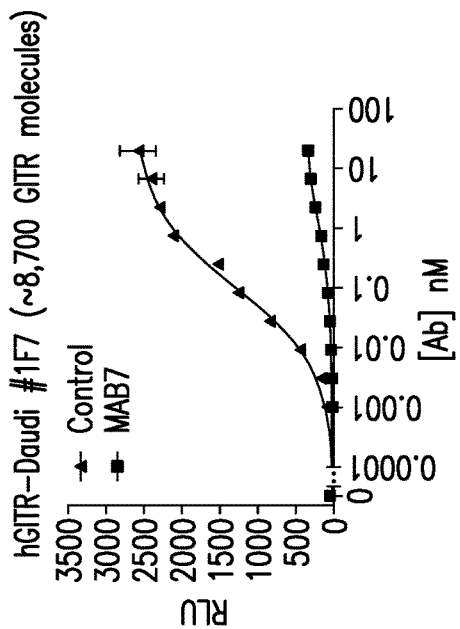

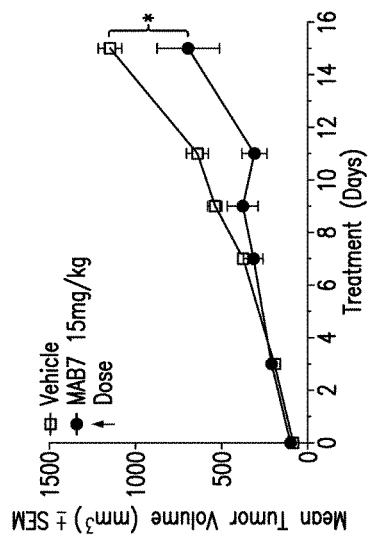
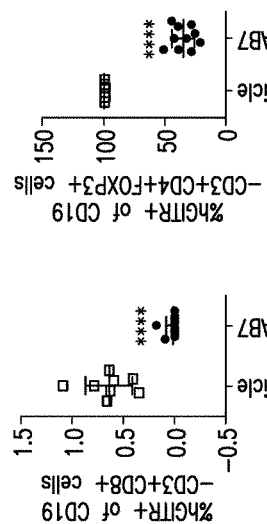
FIG. 7A, FIG. 7B, FIG. 7C, FIG. 7D, FIG. 7E

COMPOSITIONS AND METHODS OF USE FOR AUGMENTED IMMUNE RESPONSE AND CANCER THERAPY

RELATED APPLICATIONS

This application is a U.S. National Phase filing of International Application No. PCT/US2015/054775 filed 8 Oct. 2015, which claims priority to and the benefit of U.S. Provisional Application No. 62/061,644, filed Oct. 8, 2014, U.S. Provisional Application No. 62/198,673, filed Jul. 29, 2015, and U.S. Provisional Application No. 62/220,764, filed Sep. 18, 2015, each of which is hereby incorporated by reference in its entirety.

FIELD OF THE INVENTION

The present invention relates to antibodies, antibody fragments, and antigen binding molecules that bind to tumor necrosis factor receptor superfamily member 18/glucocorticoid induced TNFR-related protein ("GITR"), and more specifically that are agonists, stimulate signaling through the receptor and/or modulate immune response.

BACKGROUND OF THE INVENTION

Glucocorticoid-induced TNFR-related protein ("GITR") is a member of the Tumor Necrosis Factor Superfamily (TNFRSF) which includes more than 20 type I transmembrane proteins, several splicing variants and several viral proteins, all of which have a cysteine-rich domain as a common structural feature. The extracellular domain (ECD) of GITR consists of 3 cysteine-rich domains (CRDs), followed by a transmembrane domain (TM) and an intracellular domain (ICD).

GITR expression is detected constitutively on murine and human CD4+CD25+ regulatory T cells which can be further increased upon activation. In contrast, effector CD4+CD25− T cells and CD8+CD25− T cells express low to undetectable levels of GITR, which is rapidly upregulated following T cell receptor activation. Expression of GITR has also been detected on activated NK cells, dendritic cells, and macrophages. Signal transduction pathway downstream of GITR has been shown to involve MAPK and the canonical NFicB pathways. Various TRAF family members have been implicated as signaling intermediates downstream of GITR (Nocentini et al. (2005) Eur. J. Immunol., 35:1016-1022).

Cellular activation through GITR is believed to serve several functions depending on the cell type and microenvironment including, but not limited to, costimulation to augment proliferation and effector function, inhibition of suppression by regulatory T cells, and protection from activation-induced cell death (Shevach and Stephens (2006) Nat. Rev. Immunol., 6:613-618). Ko et al. ((2005) J. Exp. Med., 202:885-891) first demonstrated that an agonistic monoclonal antibody against mouse GITR effectively induced tumor-specific immunity and eradicated established tumors in a mouse syngeneic tumor model. Additionally and/or alternatively, an anti-mGITR which has functional Fc effector activity has been shown in some preclinical models to deplete regulatory T cells, as well as enhance T effector cell proliferation and cytokine secretion in select tumor environment. These findings suggest that an agonistic antibody to mGITR can disrupt immune tolerance balance, which in turn will allow T cells to combat tumors and persistent viral infections. However, studies to date have largely focused on use of surrogate antibodies in rodent systems. Due to the divergence of structure among mouse and human GITR, it is unknown whether findings seen with surrogate studies in mouse would translate to modification of human GITR function.

DESCRIPTION OF THE INVENTION

We have identified antibodies that specifically bind to human glucocorticoid-induced tumor necrosis factor receptor superfamily member 18 ("GITR"), wherein the antibodies have in vitro hGITR agonist activity when cross-linked in vitro, and wherein the antibodies confer hGITR activity in vivo and induce an elevated Teff:Treg ratio at tumor sites, resulting in inhibition of tumor progression. Thus, the present invention provides agonist antibodies, antibody fragments, and antigen binding molecules that specifically bind to and promote intracellular signaling and/or modulate immune response through targeting cells expressing human GITR. In one aspect, the invention provides isolated antibodies, antibody fragments, and antigen binding molecules that specifically bind to human GITR, wherein the antibody, antibody fragment, or the antigen binding molecule binds to an epitope comprising the cysteine-rich domain 1 ("CRD1", SEQ ID NO:4:

```
CGPGRLLLGTGTDARCCRVHTTRCCRDYPGEECCSEWDC)
and
the cysteine-rich domain 2

("CRD2", SEQ ID NO: 5:
MCVQPEFHCGDPCCTTCRHHPCPPGQGVQSQGKFSFGFQC),
``` and wherein the antibody, antibody fragment, or the antigen binding molecule is an agonist of GITR, and wherein the antibody, antibody fragment, or the antigen binding molecule optionally has an intact or increased FcR effector function.

In some embodiments, the antibody, antibody fragment, or the antigen binding molecule binds to an epitope comprising SEQ ID NO:88) of human GITR. In some embodiments, the antibody, antibody fragment, or antigen binding molecule competes with an antibody or antibody fragment that binds to an epitope comprising SEQ ID NO:88 of human GITR. In some embodiments, the antibody, antibody fragment, or antigen binding molecule binds to at least one amino acid residue within SEQ ID NO:88 of human GITR, for example, the antibody, antibody fragment, or antigen binding molecule binds to an epitope that overlaps with SEQ ID NO:88 of human GITR.

In some embodiments, the antibody, antibody fragment, or the antigen binding molecule binds to an epitope comprising CRD1 (residues 34-72, SEQ ID NO:4) and residue 78 of human GITR. In some embodiments, the antibody, antibody fragment, or antigen binding molecule competes with an antibody or antibody fragment that binds to an epitope within CRD1 (residues 34-72, SEQ ID NO:4) and residue 78 of human GITR. In some embodiments, the antibody, antibody fragment, or antigen binding molecule binds to at least one amino acid residue within CRD1 (residues 34-72, SEQ ID NO:4) and residue 78 of human GITR, for example, the antibody, antibody fragment, or antigen binding molecule binds to an epitope that overlaps with CRD1 (residues 34-72, SEQ ID NO:4) and residue 78 of human GITR.

In some embodiments, the antibody, antibody fragment, or antigen binding molecule binds to SEQ ID NO:1 and comprises (a) a heavy chain variable region comprising a human heavy chain wherein: i) the heavy chain CDR1 comprises SEQ ID NO:22, and ii) the heavy chain CDR2 comprises a sequence selected from any one of SEQ ID NO:23, SEQ ID NO:24, SEQ ID NO:25, SEQ ID NO:26, and SEQ ID NO:27, and iii) the heavy chain CDR3 comprises SEQ ID NO:29 or SEQ ID NO:109; and (b) a light chain variable region, wherein i) the light chain CDR1 comprises SEQ ID NO:30 or SEQ ID NO:31, and ii) the light chain CDR2 comprises SEQ ID NO:33, and iii) the light chain CDR3 comprises SEQ ID NO:34.

In some embodiments, the antibody, antibody fragment, or antigen binding molecule binds to SEQ ID NO:88 and comprises (a) a heavy chain variable region comprising a human heavy chain wherein: i) the heavy chain CDR1 comprises SEQ ID NO:22, and ii) the heavy chain CDR2 comprises a sequence selected from any one of SEQ ID NO:23, SEQ ID NO:24, SEQ ID NO:25, SEQ ID NO:26, and SEQ ID NO:27, and iii) the heavy chain CDR3 comprises SEQ ID NO:29 or SEQ ID NO:109; and (b) a light chain variable region, wherein i) the light chain CDR1 comprises SEQ ID NO:30 or SEQ ID NO:31, and ii) the light chain CDR2 comprises SEQ ID NO:33, and iii) the light chain CDR3 comprises SEQ ID NO:34.

With respect to further embodiments of the antibodies, antibody fragments, or antigen binding molecules, in some embodiments the heavy chain variable region has at least 95%, 96%, 97%, 98%, 99%, or 100% amino acid sequence identity to the variable region of SEQ ID NO:16 and the light chain variable region has at least 95%, 96%, 97%, 98%, 99%, or 100% amino acid sequence identity to the variable region of SEQ ID NO:17. In particular embodiments, the antibody, antibody fragment, or antigen binding molecule comprises a heavy chain comprising SEQ ID NO:16 and a light chain comprising SEQ ID NO:17. In some embodiments, the antibody, antibody fragment, or antigen binding molecule competes with an antibody that comprises a heavy chain comprising SEQ ID NO:16 and a light chain comprising SEQ ID NO:17.

In some embodiments, the heavy chain FR4 is a human germline FR4. In particular embodiments, the heavy chain FR4 is SEQ ID NO:42.

In some embodiments, the light chain FR4 is a human germline FR4. In particular embodiments, the light chain FR4 is SEQ ID NO:50.

In some embodiments, provided is an antibody, antibody fragment or antigen binding molecule wherein :i) the heavy chain CDR1 comprises SEQ ID NO:22 or SEQ ID NO:84; ii) the heavy chain CDR2 comprises SEQ ID NO:28 or SEQ ID NO:80; iii) the heavy chain CDR3 comprises SEQ ID NO:29 or SEQ ID NO:109; iv) the light chain CDR1 comprises SEQ ID NO:30 or SEQ ID NO:85; v) the light chain CDR2 comprises SEQ ID NO:33 or SEQ ID NO:82, and vi) the light chain CDR3 comprises SEQ ID NO:34 or SEQ ID NO:83.

In some embodiments, provided is an antibody, antibody fragment or antigen binding molecule wherein: wherein: i) the heavy chain CDR1 comprises SEQ ID NO:22; ii) the heavy chain CDR2 comprises SEQ ID NO:23; iii) the heavy chain CDR3 comprises SEQ ID NO:29; iv) the light chain CDR1 comprises SEQ ID NO:30; v) the light chain CDR2 comprises SEQ ID NO:33, and vi) the light chain CDR3 comprises SEQ ID NO:34.

In some embodiments, provided is an antibody, antibody fragment or antigen binding molecule wherein: wherein: i) the heavy chain CDR1 comprises SEQ ID NO:22; ii) the heavy chain CDR2 comprises SEQ ID NO:24; iii) the heavy chain CDR3 comprises SEQ ID NO:29; iv) the light chain CDR1 comprises SEQ ID NO:31; v) the light chain CDR2 comprises SEQ ID NO:33, and vi) the light chain CDR3 comprises SEQ ID NO:34.

In some embodiments, provided is an antibody, antibody fragment or antigen binding molecule wherein: wherein: i) the heavy chain CDR1 comprises SEQ ID NO:22; ii) the heavy chain CDR2 comprises SEQ ID NO:25; iii) the heavy chain CDR3 comprises SEQ ID NO:29; iv) the light chain CDR1 comprises SEQ ID NO:30; v) the light chain CDR2 comprises SEQ ID NO:33, and vi) the light chain CDR3 comprises SEQ ID NO:34.

In some embodiments, provided is an antibody, antibody fragment or antigen binding molecule wherein: wherein: i) the heavy chain CDR1 comprises SEQ ID NO:22; ii) the heavy chain CDR2 comprises SEQ ID NO:26; iii) the heavy chain CDR3 comprises SEQ ID NO:29; iv) the light chain CDR1 comprises SEQ ID NO:30; v) the light chain CDR2 comprises SEQ ID NO:33, and vi) the light chain CDR3 comprises SEQ ID NO:34.

In some embodiments, provided is an antibody, antibody fragment or antigen binding molecule wherein: wherein: i) the heavy chain CDR1 comprises SEQ ID NO:22; ii) the heavy chain CDR2 comprises SEQ ID NO:27; iii) the heavy chain CDR3 comprises SEQ ID NO:29; iv) the light chain CDR1 comprises SEQ ID NO:30; v) the light chain CDR2 comprises SEQ ID NO:33, and vi) the light chain CDR3 comprises SEQ ID NO:34.

In some embodiments, provided is an antibody, antibody fragment or antigen binding molecule wherein: wherein: i) the heavy chain CDR1 comprises SEQ ID NO:22; ii) the heavy chain CDR2 comprises SEQ ID NO:25; iii) the heavy chain CDR3 comprises SEQ ID NO:109; iv) the light chain CDR1 comprises SEQ ID NO:30; v) the light chain CDR2 comprises SEQ ID NO:33, and vi) the light chain CDR3 comprises SEQ ID NO:34.

In a further aspect, the invention provides antibodies, antibody fragments, or antigen binding molecules that specifically bind GITR, wherein the antibody or antibody fragment comprises a heavy chain variable region and a light chain variable regionwherein: i) the CDR1 of the heavy chain comprises an amino acid sequence selected from the group consisting of SEQ ID NO:22, SEQ ID NO: 79, or SEQ ID NO:84; ii) the CDR2 of the heavy chain comprises an amino acid sequence selected from the group consisting of SEQ ID NO:23, SEQ ID NO:24, SEQ ID NO:25, SEQ ID NO:26, SEQ ID NO:27, SEQ ID NO:62, and SEQ ID NO:80; iii) the CDR3 of the heavy chain comprises SEQ ID NO:29 or SEQ ID NO:109; iv) the CDR1 of the light chain comprises an amino acid sequence selected from the group consisting of SEQ ID NO:30, SEQ ID NO:31, SEQ ID NO:63, SEQ ID NO:81, SEQ ID NO:85, and SEQ ID NO:86; v) the CDR2 of the light chain comprises an amino acid sequence selected from the group consisting of SEQ ID NO:33, SEQ ID NO:64, and SEQ ID NO:82; and the CDR3 of the light chain comprises SEQ ID NO:34 or SEQ ID NO:83.

In other embodiments of the antibodies, antibody fragments, or antigen binding molecules, the heavy chain variable region has at least 90%, 93%, 95%, 96%, 97%, 98%, 99%, or 100% amino acid sequence identity to the variable region of a sequence selected from the group consisting of SEQ ID NO:6, SEQ ID NO:8, SEQ ID NO:12, SEQ ID NO:14, SEQ ID NO:99 and SEQ ID NO:105, and the light chain variable region has at least 90%, 93%, 95%, 96%, 97%, 98%, 99%, or 100% amino acid sequence identity to the variable region of a sequence selected from the group consisting of SEQ ID NO:9 and SEQ ID NO:7. In particular embodiments, the isolated antibody, antibody fragment, or antigen binding molecule comprises a heavy chain variable domain comprising a sequence selected from any of SEQ ID NO:6, SEQ ID NO:8, SEQ ID NO:10, SEQ ID NO:12, SEQ ID NO:14, SEQ ID NO:99 and SEQ ID NO:105; and light chain variable domain comprising SEQ ID NO:7 or SEQ ID NO:9. In some embodiments, the isolated antibody, antibody fragment, or antigen binding molecule comprises a heavy chain variable domain of SEQ ID NO:6 and a light chain variable domain of SEQ ID NO:7. In some embodiments, the isolated antibody or antibody fragment comprises a heavy chain variable domain comprising SEQ ID NO:8 and a light chain variable domain comprising SEQ ID NO:9. In other embodiments, the isolated antibody or antibody fragment comprises a heavy chain variable domain comprising SEQ ID NO:10 and a light chain variable domain comprising SEQ ID NO:7. In other embodiments, the isolated antibody or antibody fragment comprises a heavy chain variable domain comprising SEQ ID NO:12 and a light chain variable domain comprising SEQ ID NO:7. In other embodiments, the isolated antibody or antibody fragment comprises a heavy chain variable domain comprising SEQ ID NO:14 and a light chain variable domain comprising SEQ ID NO:7.

With respect to further embodiments of the antibodies, antibody fragments, or antigen binding molecules, in some embodiments the heavy chain variable region has at least 90%, 93%, 95%, 96%, 97%, 98%, 99%, or 100% amino acid sequence identity to the variable region of SEQ ID NO:99 and the light chain variable region has at least 90%, 93%, 95%, 96%, 97%, 98%, 99%, or 100% amino acid sequence identity to the variable region of SEQ ID NO:7. In some embodiments, the isolated antibody or antibody fragment comprises a heavy chain variable domain comprising the SEQ ID NO:99 and a light chain variable domain comprising SEQ ID NO:7.

With respect to further embodiments of the antibodies, antibody fragments, or antigen binding molecules, in some embodiments the heavy chain variable region has at least 90%, 93%, 95%, 96%, 97%, 98%, 99%, or 100% amino acid sequence identity to the variable region of SEQ ID NO:105 and the light chain variable region has at least 90%, 93%, 95%, 96%, 97%, 98%, 99%, or 100% amino acid sequence identity to the variable region of SEQ ID NO:7. In some embodiments, the isolated antibody or antibody fragment comprises a heavy chain variable domain comprising the SEQ ID NO:105 and a light chain variable domain comprising SEQ ID NO:7.

In some embodiments, the antibody, antibody fragment, or antigen binding molecule that binds to GITR is humanized. In certain embodiments, the antibody or antibody fragment comprises a human constant region.

In some embodiments, the antibody fragment is a Fab' fragment. In some embodiments, the antibody fragment is a single chain antibody (scFv). In some embodiments, the antibody fragment is a single-domain antibody or nanobody.

In some embodiments, the antibody or antibody fragment is cross-linked to a second antibody or antibody fragment. In some embodiments, the antibody is glycosylated.

In some embodiments, the antibody, antibody fragment, or antigen binding molecule is an IgG. In certain embodiments the antibody, antibody fragment, or antigen binding molecule comprises an IgG isotype antibody Fc region. In particular embodiments the antibody, antibody fragment, or antigen binding molecule comprises an IgG1 or an IgG2 isotype antibody Fc region. In certain embodiments the antibody, antibody fragment, or antigen binding molecule is an IgG1 or an IgG2 antibody. In some embodiments, the antibody, antibody fragment, or antigen binding molecule contains at least one mutation that modulates (i.e., increases or decreases) binding of the antibody or antibody fragment to an Fc receptor. In some embodiments, the antibody, antibody fragment, or antigen binding molecule contains at least one mutation that modulates (i.e., increases or decreases) the antibody, antibody fragment, or antigen binding molecule to activate an Fc receptor. In particular embodiments, the antibody, antibody fragment, or antigen binding molecule contains at least one mutation that increases binding of the antibody or antibody fragment to an Fc receptor. In certain embodiments, the antibody, antibody fragment, or antigen binding molecule contains at least one mutation that increases the antibody, antibody fragment, or antigen binding molecule to activate an Fc receptor.

In some embodiments, the antibody, antibody fragment, or antigen binding molecule cross-reacts with human and non-human primate GITR. In some embodiments, the antibody, antibody fragment, or antigen binding molecule does not cross-react with rodent GITR, e.g., rat GITR or mouse GITR.

In a related aspect, the invention further provides polynucleotides encoding an antibody, antibody fragment or antigen binding molecule of the invention as described herein. In some embodiments, the polynucleotide encoding the light chain variable region has at least 90%, 93%, 95%, 96%, 97%, 98%, 99%, or 100% nucleic acid sequence identity to a nucleic acid sequence selected from SEQ ID NO:52, SEQ ID NO:54 and SEQ ID NO:102. In some embodiments, the polynucleotide encoding the heavy chain variable region has at least 90%, 93%, 95%, 96%, 97%, 98%, 99%, or 100% nucleic acid sequence identity to a nucleic acid sequence selected from SEQ ID NO:51, SEQ ID NO:53, SEQ ID NO:55, SEQ ID NO:56, SEQ ID NO:57, SEQ ID NO:101, and SEQ ID NO:107. In some embodiments, the polynucleotide encoding the light chain variable region has a nucleic acid sequence selected from SEQ ID NO:52, SEQ ID NO:54, and SEQ ID NO:102. In some embodiments, the polynucleotide encoding the heavy chain variable region has a nucleic acid sequence selected from SEQ ID NO:51, SEQ ID NO:53, SEQ ID NO:55, SEQ ID NO:56, SEQ ID NO:57 SEQ ID NO:101 and SEQ ID NO:107.

In a related aspect, the invention further provides compositions comprising an antibody, antibody fragment, or antigen binding molecule of the invention, as described herein, and a pharmaceutically acceptable carrier. In some embodiments, the invention provides pharmaceutical compositions comprising an antibody, antibody fragment, or antigen binding molecule of the invention for administering to an individual.

In some embodiments, the composition further comprises a target antigen, for example, a cancer-associated antigen or a tumor-associated antigen. In some embodiments, the target antigen is a viral antigen, a bacterial antigen, a fungal antigen or a parasitic antigen.

In some embodiments, the composition further comprises an antagonist of CTLA4. In some embodiments, the composition further comprises an antagonist of LAG3. In some embodiments, the composition further comprises an antagonist of TIM3. In some embodiments, the composition further comprises an inhibitor of PD-1/PD-L1 (e.g., B7-H1 or analogue thereof, PD-1 antibody) interaction. In certain embodiments the composition further comprises an antagonist of PD-1. In certain embodiments the composition further comprises an antagonist of PD-L1.

In a further aspect, the invention further provides kits comprising an antibody or antibody fragment of the invention, as described herein.

In some embodiments, kits further comprise a second agent for co-administration with the antibody. In some embodiments, the second agent is a target antigen, for example, a cancer-associated antigen or a tumor-associated antigen. In some embodiments, the target antigen is a viral antigen, a bacterial antigen, a fungal antigen or a parasitic antigen.

In some embodiments, the second agent is an antagonist of CTLA4. In some embodiments, the second agent is an antagonist of TIM3. In some embodiments, the second agent is an antagonist of LAG3. In some embodiments, the second agent is an inhibitor of PD-1/PD-L1 (e.g., B7-H1 or analogue thereof, PD-1 antibody) interaction. In certain embodiments the second agent is an antagonist of PD-1. In certain embodiments the second agent is an antagonist of PD-L1.

Optionally, the antibody or antibody fragment and second agent are provided as a mixture. Optionally, the antibody or antibody fragment and the second agent are provided in separate formulations.

In another aspect, the invention provides methods of enhancing a T cell response in an individual in need thereof, comprising administering to the individual a therapeutically effective amount of an anti-GITR agonist antibody or antibody fragment of the invention, as described herein. In a further aspect, the invention provides an anti-GITR agonist antibody or antibody fragment of the invention for use in enhancing a T cell response in an individual. In a further aspect, the invention provides a composition comprising an antibody or antibody fragment of the invention for use in enhancing a T cell response in an individual.

In a further aspect, the invention provides methods of treating tumor growth of a cancer that expresses a tumor associated antigen in an individual in need thereof, comprising administering to the individual a therapeutically effective amount of an anti-GITR agonist antibody, antibody fragment, or antigen binding molecule of the invention, as described herein. The invention further provides an anti-GITR agonist antibody or antibody fragment of the invention for use in treating tumor growth of a cancer in an individual. The invention further provides a composition comprising an antibody or antibody fragment of the invention for use in reducing, inhibiting or preventing tumor growth of a cancer that expresses a tumor associated antigen in an individual.

With respect to embodiments of the methods and medical uses, in some embodiments, the anti-GITR agonist antibody, antibody fragment, or antigen binding molecule is co-administered with an antigen. In some embodiments, the antigen is a cancer-associated antigen or a tumor-associated antigen. In some embodiments, the anti-GITR agonist antibody or antibody fragment is co-administered with cancer cells from the patient, i.e., autologous cancer cells.

In some embodiments, the anti-GITR agonist antibody, antibody fragment, or antigen binding molecule is co-administered with an antagonist of CTLA4. In some embodiments, the anti-GITR agonist antibody, antibody fragment, or antigen binding molecule is co-administered with an antagonist of LAG3. In some embodiments, the anti-GITR agonist antibody, antibody fragment, or antigen binding molecule is co-administered with an antagonist of TIM3. In some embodiments, the anti-GITR agonist antibody or antibody fragment is co administered with an inhibitor of PD-1/PD-L1 (e.g., B7-H1) interaction. In certain embodiments, the anti-GITR agonist antibody, antibody fragment, or antigen binding molecule is co-administered with an antagonist of PD-1. In certain embodiments, the anti-GITR agonist antibody, antibody fragment, or antigen binding molecule is co-administered with an antagonist of PD-L1.

In some embodiments, the anti-GITR agonist antibody, antibody fragment, or antigen binding molecule is co-administered with a chemotherapeutic agent or a cytotoxin.

In some embodiments, the T cell response is a CD8+ cytotoxic T lymphocyte (CTL) T cell response. In some embodiments, the T cell response is a CD4+ helper T cell (Th) response.

In some embodiments, the patient has a cancer that expresses a tumor associated antigen. In some embodiments, the cancer is selected from the group consisting of melanoma, ovarian cancer, colorectal cancer, prostate, non-small cell lung cancer (NSCLC) and breast cancer. In one embodiment, the type of cancer is selected from the group consisting of: pancreatic cancer, melanomas, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, head and neck squamous cell carcinoma (HNSCC), liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

In some embodiments, the patient has an infectious disease, for example, a viral infection, a bacterial infection, a fungal antigen or a parasitic antigen. In some embodiments, the anti-GITR agonist antibody is co-administered with a viral antigen (e.g., from HCV, HSV or HIV). In some embodiments, the anti-GITR agonist antibody is co-administered with a bacterial antigen. In some embodiments, the anti-GITR agonist antibody is co-administered with a fungal antigen. In some embodiments, the anti-GITR agonist antibody is co-administered with a parasitic antigen (e.g., filariasis).

In still other embodiments, provided is an isolated antibody, antibody fragment, or antigen binding molecule for use in for use in therapy. In certain embodiments the antibody, antibody fragment or antigen binding molecule are provided for use enhancing a T cell response in an individual in need thereof. In certain embodiments the antibody, antibody fragment or antigen binding molecule are provided for use in the treatment of tumor growth in an individual in need thereof.

Definitions

An "antibody" refers to a polypeptide of the immunoglobulin family that is capable of noncovalently, reversibly, and specifically binding a corresponding antigen. An exemplary antibody structural unit comprises a tetramer. Each tetramer is composed of two identical pairs of polypeptide chains, each pair having one "light" chain (about 25 kD) and one "heavy" chain (about 50-70 kD), connected through a disulfide bond. Recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. Antibodies of the invention can be of any isotype/class (e.g., IgG, IgM, IgA, IgD, and IgE), or any subclass (e.g., IgG1, IgG2, IgG3, IgG4, IgA1, IgA2). The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. In addition to V regions, both heavy chains and light chains contain a constant (C) region or domain. A secreted form of a immunoglobulin C region is made up of three C domains, CH1, CH2, CH3, optionally CH4 (C µ), and a hinge region. A membrane-bound form of an immunglobulin C region also has membrane and intracellular domains. Each light chain has a VL at the N-terminus followed by a constant domain (C) at its other end. The VL is aligned with the VH and the CL is aligned with the first constant domain of the heavy chain. The pairing of a VH and VL together forms a single antigen-binding site. A "conventional antibody" IgG immunoglobulin as used herein refers to an antibody in a configuration that occurs in nature. Typically, a conventional antibody IgG has four chains, two identical heavy chains and two identical light chains linked together through disulfide bonds. As used herein, an "antibody" also encompasses variations of antibodies and conventional antibody structures that possess a particular binding specificity, i.e., for GITR. Thus, within the scope of this concept are full length antibodies, chimeric antibodies, and humanized antibodies, that possess a particular binding specificity for GITR.

Antibodies exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab' which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region. Paul, *Fundamental Immunology* 3d ed. (1993). While various antibody fragments are defined in terms of the digestion of an intact antibody, one of skill will appreciate that such fragments may be synthesized de novo either chemically or by using recombinant DNA methodology. As used herein, an "antibody fragment" refers to one or more portions of an antibody, either produced by the modification of whole antibodies, or those synthesized de novo using recombinant DNA methodologies, that retain binding specificity and agonist activity for GITR. Examples of antibody fragments include Fv fragments, single chain antibodies (ScFv), Fab, Fab', Fd (Vh and CH1 domains), dAb (Vh and an isolated CDR); and multimeric versions of these fragments (e.g., $F(ab')_2$,) with the same binding specificity. Antibody fragments can also be incorporated into single domain antibodies, maxibodies, minibodies, diabodies, triabodies, tetrabodies, vNAR, bis-scFv, and other variations of antibody-like compounds to achieve the binding specificity and activity provided in the present invention.

A "Fab" domain as used in the context of the invention comprises a heavy chain variable domain, a constant region CH1 domain, a light chain variable domain, and a light chain constant region CL domain. The interaction of the domains is stabilized by a disulfide bond between the CH1 and CL domains. In some embodiments, the heavy chain domains of the Fab are in the order, from N-terminus to C-terminus, VH-CH and the light chain domains of a Fab are in the order, from N-terminus to C-terminus, VL-CL. In some embodiments, the heavy chain domains of the Fab are in the order, from N-terminus to C-terminus, CH-VH and the light chain domains of the Fab are in the order CL-VL. Although Fabs were historically identified by papain digestion of an intact immunoglobulin, in the context of this invention, a "Fab" is typically produced recombinantly by any method. Each Fab fragment is monovalent with respect to antigen binding, i.e., it has a single antigen- binding site.

The C-terminal portion of the immunoglobulin heavy chains, comprising the CH2 and CH3 domains, is the "Fc" domain. An "Fc region" as used herein refers to the constant region of an antibody excluding the first constant region immunoglobulin domain. Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ. It is understood in the art that the boundaries of the Fc region may vary, however, the human IgG heavy chain Fc region is usually defined to comprise residues C226 or P230 to its carboxyl-terminus, using the numbering is according to the EU index as in Kabat et al. (1991, NIH Publication 91-3242, National Technical Information Service, Springfield, Va.). "Fc region" may refer to this region in isolation or this region in the context of an antibody or antibody fragment. "Fc region" includes naturally occurring allelic variants of the Fc region, e.g., in the CH2 and CH3 region, as well as modifications that modulate effector function. Fc regions also include variants that don't result in alterations to biological function. For example, one or more amino acids can be deleted from the N-terminus or C-terminus of the Fc region of an immunoglobulin without substantial loss of biological function. For example, in certain embodiments a C-terminal lysine may be modified replaced or removed. In particular embodiments one or more C-terminal residues in the Fc region is altered or removed. In certain embodiments one or more C-terminal residues in the Fc (e.g., the terminal lysine) is deleted. In certain other embodiments one or more C-terminal residues in the Fc is substituted with an alternate amino acid (e.g., the terminal lysine is replaced). Such variants can be selected according to general rules known in the art so as to have minimal effect on activity (see, e.g., Bowie, et al., Science 247:306-1310, 1990). The Fc domain is the portion of the Ig recognized by cell receptors, such as the FcR, and to which the complement-activating protein, C1 q, binds. The lower hinge region, which is encoded in the 5' portion of the CH2 exon, provides flexibility within the antibody for binding to FcR receptors.

"Complementarity-determining domains" or "complementary-determining regions" ("CDRs") interchangeably refer to the hypervariable regions of $V_L$ and $V_H$. CDRs are the target protein-binding site of the antibody chains that harbors specificity for such target protein. There are three CDRs (CDR1-3, numbered sequentially from the N-terminus) in each human $V_L$ or $V_H$, constituting about 15-20% of the variable domains. CDRs are structurally complementary to the epitope of the target protein and are thus directly responsible for the binding specificity. The remaining stretches of the $V_L$ or $V_H$, the so-called framework regions, exhibit less variation in amino acid sequence (Kuby, Immunology, 4th ed., Chapter 4. W.H. Freeman & Co., New York, 2000).

Positions of the CDRs and framework regions can be determined using various well known definitions in the art, e.g., Kabat, Chothia, international ImMunoGeneTics database (IMGT) (on the worldwide web at imgt.cines.fr/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Under Kabat, CDR amino acid residues in the $V_H$ are numbered 31-35 (HCDR1), 50-65 (HCDR2), and 95-102 (HCDR3); and the CDR amino acid residues in the $V_L$ are numbered 24-34 (LCDR1), 50-56 (LCDR2), and 89-97 (LCDR3). Under Chothia, CDR amino acids in the $V_H$ are numbered 26-32 (HCDR1), 52-56 (HCDR2), and 95-102 (HCDR3); and the amino acid residues in $V_L$ are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

The term "binding specificity determinant" or "BSD" interchangeably refer to a minimum contiguous or non-contiguous amino acid sequence within a complementary determining region necessary for determining the binding specificity of an antibody. A minimum binding specificity determinant can be within one or more CDR sequences. In some embodiments, the minimum binding specificity determinants reside within (i.e., are determined solely by) a portion or the full-length of the CDR3 sequences of the heavy and light chains of the antibody.

An "antibody light chain" or an "antibody heavy chain" as used herein refers to a polypeptide comprising the $V_L$ or $V_H$, respectively. The endogenous $V_L$ is encoded by the gene segments V (variable) and J (junctional), and the endogenous $V_H$ by V, D (diversity), and J. Each of $V_L$ or $V_H$ includes the CDRs as well as the framework regions. In this application, antibody light chains and/or antibody heavy chains may, from time to time, be collectively referred to as "antibody chains." These terms encompass antibody chains containing mutations that do not disrupt the basic structure of $V_L$ or $V_H$, as one skilled in the art will readily recognize.

The term "valency" as used herein refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different molecules, e.g., different antigens, or different epitopes on the same molecule). A conventional antibody, for example, has two binding sites and is bivalent. The antibodies, antigen binding molecules, and fragments thereof, can be monovalent (i.e., bind one target molecule), bivalent, or multivalent (i.e., bind more than one target molecule).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., Monoclonal Antibodies and Cancer Therapy, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express primatized or humanized antibodies. Alternatively, phage display technology can be used to identify antibodies and heteromeric Fab fragments that specifically bind to selected antigens (see, e.g., McCafferty et al., supra; Marks et al., *Biotechnology,* 10:779-783, (1992)).

Methods for primatizing or humanizing non-human antibodies are well known in the art. Generally, a primatized or humanized antibody has one or more amino acid residues introduced into it from a source which is non-primate or non-human. These non-primate or non-human amino acid residues are often referred to as import residues, which are typically taken from an import variable domain. Humanization can be essentially performed following the method of Winter and co-workers (see, e.g., Jones et al., *Nature* 321: 522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, primatized or humanized antibodies are typically primate or human antibodies in which some complementary determining region ("CDR") residues and possibly some framework ("FR") residues are substituted by residues from analogous sites in an originating species (e.g., rodent antibodies) to confer binding specificity.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, and drug; or (b) the variable region, or a portion thereof, is altered, replaced or exchanged with a variable region having a different or altered antigen specificity.

Antibodies or antigen-binding molecules of the invention further include one or more immunoglobulin chains that are chemically conjugated to, or expressed as, fusion proteins with other proteins. It also includes bispecific antibody. A bispecific or bifunctional antibody is an artificial hybrid antibody having two different heavy/light chain pairs and two different binding sites. Other antigen-binding fragments or antibody portions of the invention include bivalent scFv (diabody), bispecific scFv antibodies where the antibody molecule recognizes two different epitopes, single binding domains (dAbs), and minibodies.

The various antibodies or antigen-binding fragments described herein can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or native and immunocompetent sources.

The term "antigen binding molecule" or "non-antibody ligand" refers to antibody mimics that use non-immunoglobulin protein scaffolds, including but not limited to, adnectins, avimers, single chain polypeptide binding molecules, and antibody-like binding peptidomimetics.

The term "variable region" or "V-region" interchangeably refer to a heavy or light chain comprising FR1-CDR1-FR2-CDR2-FR3-CDR3-FR4. An endogenous variable region is encoded by immunoglobulin heavy chain V-D-J genes or light chain V-J genes. A V-region can be naturally occurring, recombinant or synthetic.

As used herein, the term "variable segment" or "V-segment" interchangeably refer to a subsequence of the variable region including FR1-CDR1-FR2-CDR2-FR3. An endogenous V-segment is encoded by an immunoglobulin V-gene. A V-segment can be naturally occurring, recombinant or synthetic.

As used herein, the term "J-segment" refers to a subsequence of the variable region encoded comprising a C-terminal portion of a CDR3 and the FR4. An endogenous J-segment is encoded by an immunoglobulin J-gene. A J-segment can be naturally occurring, recombinant or synthetic.

A "humanized" antibody is an antibody that retains the reactivity (e.g., binding specificity, activity) of a non-human antibody while being less immunogenic in humans. This can be achieved, for instance, by retaining non-human CDR regions and replacing the remaining parts of the antibody with human counterparts. See, e.g., Morrison et al., *Proc. Natl. Acad. Sci. USA*, 81:6851-6855 (1984); Morrison and Oi, *Adv. Immunol.*, 44:65-92 (1988); Verhoeyen et al., *Science*, 239:1534-1536 (1988); Padlan, *Molec. Immun.*, 28:489-498 (1991); Padlan, *Molec. Immun.*, 31(3):169-217 (1994).

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementary determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 93%, 94%, 95%, 96%, 97%, 98%, 99%, or 100% sequence identity with the reference variable region nucleic acid or amino acid sequence. Corresponding human germline sequences can be determined, for example, through the publicly available international ImMunoGeneTics database (IMGT) (on the worldwide web at imgt.cines.fr/) and V-base (on the worldwide web at vbase.mrc-cpe.cam.ac.uk).

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agents with a particular binding specificity bind to a particular antigen at least ten (10) times the background and do not substantially bind in a significant amount to other antigens present in the sample. Specific binding to an antibody or binding agent under such conditions may require the antibody or agent to have been selected for its specificity for a particular protein (e.g., human GITR). As used herein, specific binding includes antibodies fragments thereof and binding molecules that selectively bind to human GITR and do not include antibodies that cross-react with, e.g., murine GITR molecules or other TNF receptor superfamily members. In some embodiments, antibodies or antibody fragments are selected that cross-react with non-human primate GITR (e.g., cynomolgus GITR).

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "equilibrium dissociation constant ($K_D$, M)" refers to the dissociation rate constant ($k_d$, time$^{-1}$) divided by the association rate constant ($k_a$, time$^{-1}$, M$^{-1}$). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M. In some embodiments, the isolated antibody or antibody fragment binds to human GITR with an equilibrium dissociation constant ($K_D$) of about 1 nM or less. In some embodiments, the antibody or antibody fragment binds to human GITR with a $K_D$ that is less than 1 nM. In some embodiments, the antibody or antibody fragment binds to human GITR with a $K_D$ that is in the range of from about 0.5 nM to about 1.0 nM.

As used herein, the term "antigen-binding region" refers to a domain of the GITR-binding molecule of this invention that is responsible for the specific binding between the molecule and GITR. An antigen-binding region includes at least one antibody heavy chain variable region and at least one antibody light chain variable region. There are at least one such antigen-binding regions present in each GITR-binding molecule of this invention, and each of the antigen-binding regions may be identical or different from the others. In some embodiments, at least one of the antigen-binding regions of a GITR-binding molecule of this invention acts as an agonist of GITR.

The term "antibody agonist" or "agonist" interchangeably refer to an antibody capable of activating a receptor to induce a full or partial receptor-mediated response. For example, an agonist of GITR binds to GITR and induces GITR-mediated intracellular signaling (e.g., increased NF-κB expression activation). The antibody agonist stimulates signaling through GITR similarly to the native ligand, GITR-L. Binding of GITR-L to GITR induces NFκB activation due to degradation of IκB. In some embodiments, a GITR antibody agonist can be identified by its ability to bind GITR and induce T cell (e.g., CD8$^+$ CTLs or CD4$^+$ Th cells) proliferation, survival, cytolytic activity and/or cytokine production (e.g., IFNγ, IL-10, IL-13, TNFα) or as otherwise described herein.

The term "GITR" or "glucocorticoid-induced tumor necrosis factor receptor receptor" or "tumor necrosis factor receptor superfamily, member 18" or "TNFRSF18" interchangeably refer to a type I transmembrane protein that is a member of the TNF-receptor superfamily. GITR is expressed at high levels on CD4$^+$ CD25$^+$ and on activated effector CD4$^+$ and CD8$^+$ T cells. The nucleic acid and amino acid sequences of GITR are known, and have been published in NM_148902.1, NM_005092 or SEQ ID NOs:1-4. Functionally, agonism of rodent GITR inhibits, at least transiently, suppressor activity of CD25$^+$ regulatory T cells (Treg). GITR agonism further enhances immunoactivity, e.g., proliferation, survival, cytokine production and cytolytic activity of activated effector CD4$^+$ and CD8$^+$ T cells. See, e.g., Nocentini, et al., *Eur J Immunol* (2007) 37:1165-1169; *Expert Opin Ther Patents* (2007) 17(5):567-757; Shevach and Stephens, *Nature Reviews Immunology* (2006) 6:613-618.

"Activity" of a polypeptide of the invention refers to structural, regulatory, or biochemical functions of a polypeptide in its native cell or tissue. Examples of activity of a polypeptide include both direct activities and indirect activities. Exemplary activities of GITR agonism include intracellular signaling that results in increased activation of NF-κB, increased proliferation, survival, cytokine production (e.g., IFNγ, IL-10, IL-13, TNFα), and cytolytic activity of activated effector CD4$^+$ and CD8$^+$ T cells. Therapeutically, agonism of GITR augments antitumor and antiviral T-cell responses in vivo.

The term "isolated," when applied to a nucleic acid or protein, denotes that the nucleic acid or protein is essentially

```
GenBank Accession Nos. NM_004195.2→NP_004186.1 (isoform 1 precursor), SEQ ID NO: 1:
    1   maqhgamgaf ralcglallc alslgqrptg gpgcgpgrll lgtgtdarcc rvhttrccrd 61   ypgeeccsew dcmcvqpefh cgdpccttcr hhpcppgqgv qsqgkfsfgf qcidcasgtf 121   sggheghckp wtdctqfgfl tvfpgnkthn avcvpgsppa eplgwltvvl lavaacvlll 181   tsaqlglhiw qlrsqcmwpr etqlllevpp stedarscqf peeergersa eekgrlgdlw 241   v;

NM_148901.1→NP_683699.1 (isoform 2 precursor), SEQ ID NO: 2:
    1   maqhgamgaf ralcglallc alslgqrptg gpgcgpgrll lgtgtdarcc rvhttrccrd 61   ypgeeccsew dcmcvqpefh cgdpccttcr hhpcppgqgv qsqgkfsfgf qcidcasgtf 121   sggheghckp wtdccwrcrr rpktpeaass prksgasdrq rrrggwetcg cepgrppgpp 181   taaspspgap qaagalrsal grallpwqqk wvqeggsdqr pgpcssaaaa gperreretq 241   swppsslagp dgvgs;
and NM_148902.1→NP_683700.1 (isoform 3 precursor), SEQ ID NO: 3:
    1   maqhgamgaf ralcglallc alslgqrptg gpgcgpgrll lgtgtdarcc rvhttrccrd 61   ypgeeccsew dcmcvqpefh cgdpccttcr hhpcppgqgv qsqgkfsfgf qcidcasgtf 121   sggheghckp wtdctqfgfl tvfpgnkthn avcvpgsppa eplgwltvvl lavaacvlll 181   tsaqlglhiw qlrktqllle vppstedars cqfpeeerge rsaeekgrlg dlwv.

See also, Gen-Bank Accession No. NM_005092→NP 005083.2.
```

Structurally, a GITR amino acid sequence is a type I transmembrane protein that is a member of the TNF-receptor superfamily having a signal peptide, an extracellular domain (ECD) comprising three cysteine-rich domains (CRDs) and has over its full length at least about 90%, 91%, 92%, 93%, 94%, 95%, 96%, 97%, 98%, 99%, or 100% sequence identity with the amino acid sequence of GenBank accession numbers NP_004186.1(SEQ ID NO:1), NP_683699.1(SEQ ID NO:2), NP_683700.1(SEQ ID NO:3), or NP_005083.2. Structurally, a GITR nucleic acid sequence has over its full length at least about 90%, 91%, 92%, 93%, 94%, 95%, 96%, 97%, 98%, 99%, or 100% sequence identity with the nucleic acid sequence of GenBank accession numbers NM_004195.2, NM_148901.1, free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., at least 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. The invention provides polypeptides or polynucleotides that are substantially identical to the polypeptides or polynucleotides, respectively, exemplified herein (e.g., the variable regions exemplified in any one of SEQ ID NOS:6-10, 12, 14, 59 and 61; the variable segments exemplified in any one of SEQ ID NOS:16-17; the CDRs exemplified in any one of SEQ ID NOS:22-34; the FRs exemplified in any one of SEQ ID NOS:35-50; and the nucleic acid sequences exemplified in any on of SEQ ID NOS:51-58 and 60). Optionally, the identity exists over a region that is at least about 15, 25 or 50 nucleotides in length, or more preferably over a region that is 100 to 500 or 1000 or more nucleotides in length, or over the full length of the reference sequence. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "link," when used in the context of describing how the antigen-binding regions are connected within a GITR-binding molecule of this invention, encompasses all possible means for physically joining the regions. The multitude of antigen-binding regions are frequently joined by chemical bonds such as a covalent bond (e.g., a peptide bond or a disulfide bond) or a non-covalent bond, which can be either a direct bond (i.e., without a linker between two antigen-binding regions) or indirect bond (i.e., with the aid of at least one linker molecule between two or more antigen-binding regions).

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

As used herein, the terms "treat," "treating," or "treatment" of any disease or disorder refer in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of the disease or disorder.

The term "therapeutically acceptable amount" or "therapeutically effective dose" interchangeably refer to an amount sufficient to effect the desired result (i.e., a reduction in tumor size, inhibition of tumor growth, prevention of metastasis, inhibition or prevention of viral, bacterial, fungal or parasitic infection). In some embodiments, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of a GITR agonizing antibody of the invention can prevent the onset of, or result in a decrease in severity of, respectively, disease symptoms, including symptoms associated with cancer or infectious disease.

The term "co-administer" refers to the simultaneous presence of two active agents in the blood of an individual. Active agents that are co-administered can be concurrently or sequentially delivered.

As used herein, the phrase "consisting essentially of" refers to the genera or species of active pharmaceutical agents included in a method or composition, as well as any inactive carrier or excipients for the intended purpose of the methods or compositions. In some embodiments, the phrase "consisting essentially of" expressly excludes the inclusion of one or more additional active agents other than an agonist anti-GITR antibody of the invention. In some embodiments, the phrase "consisting essentially of" expressly excludes the inclusion of one or more additional active agents other than an agonist anti-GITR antibody of the invention and a second co-administered agent.

The terms "cancer-associated antigen" or "tumor-associated antigen" or "tumor-specific marker" or "tumor marker" interchangeably refers to a molecule (typically protein, carbohydrate or lipid) that is preferentially expressed on the surface of a cancer cell in comparison to a normal cell, and which is useful for the preferential targeting of a pharmacological agent to the cancer cell. Oftentimes, a cancer-associated antigen is a cell surface molecule that is overexpressed in a cancer cell in comparison to a normal cell, for instance, 1-fold over expression, 2-fold overexpression, 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal.

As used herein, the terms "first", "second", "third" and "fourth", with respect to antigen binding moieties, e.g., Fabs, are used for convenience of distinguishing when there is more than one of each moiety. Use of these terms is not intended to confer a specific order or orientation of the antibody unless otherwise stated.

The terms "a," "an," and "the" include plural referents, unless the context clearly indicates otherwise Agonist Anti-GITR Antibodies The present invention provides antibodies, antibody fragments, and antigen binding molecules that bind to and stimulate signaling through GITR and/or induce a potentiated immune response in vivo. The antibodies, antibody fragments, and antigen binding molecules find uses in enhancing CD4+ T helper (Th) and/or CD8+ cytolytic T lymphocyte (CTL) responses against a target antigen. They also find uses in treating disease conditions whose progression can be reversed or inhibited by an effective immune response, including cancers and infectious diseases.

The antibodies, antibody fragments and antigen binding molecules of the present invention show suitable properties to be used in human patients, for example, they have low risk for immunogenicity issues for uses in human (they are encoded by human germline nucleic acid sequences, with the exception of of the binding specificity determining regions (BSD), in particular at least CDR3); have high affinity to GITR (e.g., $K_D$ is at least less than 5 nM); do not cross-react with other members of the TNFR superfamily; cross-react with human and non-human primate GITR; and agonize GITR signaling at low doses (e.g., in concentrations of less than 5 nM in in vitro assays). Other activities and characteristics are also demonstrated throughout the specification.

Accordingly, the present invention provides antibodies, antibody fragments, and antigen-binding molecules that are agonists of GITR. Provided anti-GITR antibodies, antibody fragments, or antigen-binding molecules contain a minimum binding sequence determinant (BSD) within the CDR3 of the heavy and light chains derived from the originating or reference monoclonal antibody, for example, the antibodies described in Table 1 and Table 2 below. The remaining sequences of the heavy chain and light chain variable regions (CDR and FR), e.g., V-segment and J-segment, are from corresponding human germline and affinity matured amino acid sequences. The V-segments can be selected from a human V-segment library. Further sequence refinement can be accomplished by affinity maturation or other methods known in the art to optimize binding activity or activity of the antibodies, antibody fragments or antigen binding molecules of the invention.

In another embodiment, heavy and light chains of the anti-GITR antibodies or antibody fragments contain a human V-segment from the corresponding human germline sequence (FR1-CDR1-FR2-CDR2-FR3), e.g., selected from a human V-segment library, and a CDR3-FR4 sequence segment from the originating monoclonal antibody (e.g., the antibodies as described in Table 1 and Table 2). The CDR3-FR4 sequence segment can be further refined by replacing sequence segments with corresponding human germline sequences and/or by affinity maturation. For example, the FR4 and/or the CDR3 sequence surrounding the BSD can be replaced with the corresponding human germline sequence, while the BSD from the CDR3 of the originating monoclonal antibody is retained.

In some embodiments, the corresponding human germline sequence for the heavy chain V-segment is VH3 3-13/30: EVQLVESGGGLVQPGGSLRLSCAASGFTFSSYGMH-WVRQAPGKGLEWVAVIRYDGSNKYYADSVKGR-FTISRDNSKNTLYLQMNSLRAEDTAVYYCAK (SEQ ID NO:89). In one embodiment, the last amino acid in SEQ ID NO:89, lysine ("K"), is substituted with arginine ("R"). In some embodiments, the corresponding human germline sequence for the heavy chain J-segment is JH4. In some embodiments, the heavy chain J-segment comprises the human germline JH4 partial sequence WGQGTLVTVSS (SEQ ID NO:90). The full-length J-segment from human germline JH4 is YFDYWGQGTLVTVSS (SEQ ID NO:91). The variable region genes are referenced in accordance with the standard nomenclature for immunoglobulin variable region genes. Current immunoglobulin gene information is available through the worldwide web, for example, on the ImMunoGeneTics (IMGT), V-base and PubMed databases. See also, Lefranc, *Exp Clin Immunogenet.* 2001; 18(2):100-16; Lefranc, *Exp Clin Immunogenet.* 2001; 18(3):161-74; *Exp Clin Immunogenet.* 2001;18(4):242-54; and Giudicelli, et al., *Nucleic Acids Res.* 2005 Jan. 1; 33(Database issue): D256-61.

In some embodiments, the corresponding human germline sequence for the light chain V-segment is VKIII L16/A27: EIVMTQSPATLSVSPGERATLSCRASQSVSSNLAWY-QQKPGQAPRLLIYGASTRATGIPDRFSGSGSGTD-FTLTISRLEPEDFAVYYCQQYGSSP (SEQ ID NO:92). In some embodiments, the corresponding human germline sequence for the light chain J-segment is JK2. In some embodiments, the light chain J-segment comprises the human germline Jk2 partial sequence FGQGTKLEIK (SEQ ID NO:93). The full-length J segment from human germline Jk2 is YTFGQGTKLEIK (SEQ ID NO:94).

In some embodiments, the heavy chain V-segment has at least 95%, 96%, 97%, 98%, 99% or 100% sequence identity to the amino acid sequence (E/Q)VQLVESGGGLVQ(P/S) GGSLRLSCAASGFSLSSYGVDWVRQAPGKGLEW(L/V)GVIWGGGGTYY(A/T)(A/S)S(L/V)M(A/G) RFTISRDNSKNTLYLQMNSLRAEDTAVYYCA(K/R)(H/N)AYGHDGGFAMDYWGQGTLVTVSS (SEQ ID NO:16).

In some embodiments, the light chain V-segment has at least 95%, 96%, 97%, 98%, 99% or 100% sequence identity to the amino acid sequence EIVMTQSPATLSVSPGER-ATLSCRAS(E/Q)SVSSN(L/V)AWYQQ(K/R) PGQAPRLLIYGASNRATGIP(D/A)RFSGSGSGTD-FTLTISRLEPEDFAVYYCGQSYSYPFTFGQGTKLEIK (SEQ ID NO:17).

In some embodiments, i) the heavy chain CDR3 comprises the amino acid sequence HAYGHDGGFAMDY (SEQ ID NO: 29) or NAYGHDGGFAMDY (SEQ ID NO:109); and ii) the light chain CDR3 variable region comprises the amino acid sequence GQSYSYPFT (SEQ ID NO:34), or SYSYPF (SEQ ID NO:83).

In some embodiments, the antibodies or antibody fragments of the invention comprise a heavy chain variable region comprising a CDR1 comprising an amino acid sequence SYGVD (SEQ ID NO:22), or GFSLSSY (SEQ ID NO:84); a CDR2 comprising an amino acid sequence VIWGGGGTYY(A/T)(A/S)S(L/V)M(A/G) (SEQ ID NO:28), or WGGGG (SEQ ID NO:80); and a CDR3 comprising an amino acid sequence of HAYGHDGGFAMDY (SEQ ID NO:29) or NAYGHDGGFAMDY (SEQ ID NO:109).

In some embodiments, the antibodies or antibody fragments of the invention comprise a light chain variable region comprising a CDR1 comprising an amino acid sequence RAS(E/Q)SVSSN(L/V)A (SEQ ID NO:32) or S(E/Q)SVSSN (SEQ ID NO:87); a CDR2 comprising an amino acid sequence GASNRAT (SEQ ID NO:33), or GAS (SEQ ID NO:82); and a CDR3 comprising an amino acid sequence of GQSYSYPFT (SEQ ID NO:34), or SYSYPF (SEQ ID NO:83).

In some embodiments, the antibodies or antibody fragments of the invention comprise a heavy chain variable region comprising a CDR1 comprising an amino acid sequence SYGVD (SEQ ID NO:22), or GFSLSSY (SEQ ID NO:84); a CDR2 comprising an amino acid sequence VIWGGGGTYY(A/T)(A/S)S(L/V)M(A/G) (SEQ ID NO:28) or WGGGG (SEQ ID NO:80); and a CDR3 comprising an amino acid sequence of HAYGHDGGFAMDY (SEQ ID NO:29) or NAYGHDGGFAMDY (SEQ ID NO:109). Such antibodies or antibody fragments of the invention further comprise a light chain variable region comprising a CDR1 comprising an amino acid sequence RAS(E/Q)SVSSN(L/V)A (SEQ ID NO:32), or S(E/Q)SVSSN (SEQ ID NO:87); a CDR2 comprising an amino acid sequence GASNRAT (SEQ ID NO:33), or GAS (SEQ ID NO:82); and a CDR3 comprising an amino acid sequence of GQSYSYPFT (SEQ ID NO:34), or SYSYPF (SEQ ID NO:83).

In some embodiments, the antibodies or antibody fragments of the invention comprise a heavy chain variable region comprising a CDR1 comprising an amino acid sequence SYGVD (SEQ ID NO:22), or GFSLRSY (SEQ ID NO:79); a CDR2 comprising an amino acid sequence VIWGGGGTNYNSALMA (SEQ ID NO:62), or WGGGG (SEQ ID NO:80); and a CDR3 comprising an amino acid sequence of HAYGHDGGFAMDY (SEQ ID NO:29) or NAYGHDGGFAMDY (SEQ ID NO:109). In some embodiments, the antibodies or antibody fragments are humanized.

In some embodiments, the antibodies or antibody fragments of the invention comprise a light chain variable region comprising a CDR1 comprising an amino acid sequence KASENVDTFVS (SEQ ID NO:63), or SENVDTF (SEQ ID NO:81); a CDR2 comprising an amino acid sequence GASNRYT (SEQ ID NO:64), or GAS (SEQ ID NO:82); and a CDR3 comprising an amino acid sequence of GQSYSYPFT (SEQ ID NO:34), or SYSYPF (SEQ ID NO:83). In some embodiments, the antibodies or antibody fragments are humanized.

In some embodiments, the antibodies or antibody fragments of the invention comprise a heavy chain variable region comprising a CDR1 comprising an amino acid sequence SYGVD (SEQ ID NO:22), or GFSLRSY (SEQ ID NO:79); a CDR2 comprising an amino acid sequence VIWGGGGTNYNSALMA (SEQ ID NO:62), or WGGGG (SEQ ID NO:80); and a CDR3 comprising an amino acid sequence of HAYGHDGGFAMDY (SEQ ID NO:29) or NAYGHDGGFAMDY (SEQ ID NO:109). Such antibodies or antibody fragments further comprise a light chain variable region comprising a CDR1 comprising an amino acid sequence KASENVDTFVS (SEQ ID NO:63), or SENVDTF (SEQ ID NO:81); a CDR2 comprising an amino acid sequence GASNRYT (SEQ ID NO:64), or GAS (SEQ ID NO:82); and a CDR3 comprising an amino acid sequence of GQSYSYPFT (SEQ ID NO:34), or SYSYPF (SEQ ID NO:83). In some embodiments, the antibodies or antibody fragments are humanized.

In some embodiments, the heavy chain variable region comprises a FR1 comprising the amino acid sequence of (E/Q)VQLVESGGGLVQ(P/S)GGSLRLSCAASGFSLS (SEQ ID NO:37); a FR2 comprising the amino acid sequence of WVRQAPGKGLEW(L/V)G (SEQ ID NO:40); a FR3 comprising the amino acid sequence of RFTISRDN-SKNTLYLQMNSLRAEDTAVYYCA(K/R) (SEQ ID NO:41); and a FR4 comprising the amino acid sequence of WGQGTLVTVSS (SEQ ID NO:42). In some embodiments, the heavy chain variable region comprises a FR1 comprising the amino acid sequence selected from QVQLVES-GGGLVQPGGSLRLSCAASGFSLS (SEQ ID NO:35) and QVQLVESGGGLVQPGGSLRLSCAASGFSLS (SEQ ID NO:36); a FR2 comprising the amino acid sequence selected from WVRQAPGKGLEWVG (SEQ ID NO:38) and WVRQAPGKGLEWLG (SEQ ID NO:39); a FR3 comprising the amino acid sequence of SEQ ID NO:41; and a FR4 comprising the amino acid sequence of SEQ ID NO:42. The identified amino acid sequences may have one or more substituted amino acids (e.g., from affinity maturation) or one or two conservatively substituted amino acids.

In some embodiments, the light chain variable region comprises a FR1 comprising an amino acid sequence of EIVMTQSPATLSVSPGERATLSC (SEQ ID NO:43); a FR2 comprising the amino acid sequence of WYQQ(K/R)PGQAPRLLIY (SEQ ID NO:46); a FR3 comprising the amino acid sequence of GIP(A/D)RFSGSGSGTDFTLTISRLEPEDFAVYYC (SEQ ID NO:49); and a FR4 comprising the amino acid sequence of SEQ ID NO:50. In some embodiments, the light chain variable region comprises a FR1 comprising an amino acid sequence of SEQ ID NO:43; a FR2 comprising the amino acid sequence selected from WYQQRPGQAPRLLIY (SEQ ID NO:44) and WYQQKPGQAPRLLIY (SEQ ID NO:45); a FR3 comprising the amino acid sequence selected from GIPARFSGSGSGTDFTLTISRLEPEDFAVYYC (SEQ ID NO:47) and GIPDRFSGSGSGTDFTLTISRLEPEDFAVYYC (SEQ ID NO:48); and a FR4 comprising the amino acid sequence of FGQGTKLEIK (SEQ ID NO:50). The identified amino acid sequences may have one or more substituted amino acids (e.g., from affinity maturation) or one or two conservatively substituted amino acids.

Over their full length, the variable regions of the anti-GITR antibodies of the present invention generally will have an overall variable region (e.g., FR1-CDR1-FR2-CDR2-FR3-CDR3-FR4) amino acid sequence identity of at least about 85%, for example, at least about 85%, 89%, 90%, 91%, 92%, 93%, 94%, 95%, 96%, 97%, 98%, 99%, or 100% to the corresponding human germline variable region amino acid sequence. For example, the heavy chain of the anti-GITR antibodies can have at least about 85%, 89%, 90%, 91%, 92%, 93%, 94%, 95%, 96%, 97%, 98%, 99%, or 100% amino acid sequence identity to the human germline variable region EVQLVESGGGLVQPGGSLRLSCAASGFTFSSYGMHWVRQAPGKGLEWVAVIRYDGSNKYYADSVKGRFTISRDNSKNTLYLQMNSLRAEDTAVYYCAKYFDYWGQGTLVTVSS (SEQ ID NOS:89 and 91)(VH3 3-13/30+CDR3+JH4, the hyphen represents CDR3, which may be variable in length). In one embodiment, the last amino acid in SEQ ID NO: 89, lysine (K), is substituted with arginine (R). The light chain of the anti-GITR antibodies can have at least about 85%, 89%, 90%, 91%, 92%, 93%, 94%, 95%, 96%, 97%, 98%, 99%, or 100% amino acid sequence identity to the human germline variable region EIVMTQSPATLSVSPGERATLSCRASQSVSSNLAWYQQKPGQAPRLLIYGASTRATGIPDRFSGSGSGTDFTLTISRLEPEDFAVYYC-YTFGQGTKLEIK (SEQ ID NOS:98 and 94) (VKIII L16/A27+CDR3+JK2; the hyphen represents CDR3, which may be variable in length). In some embodiments, only amino acids within the framework regions are added, deleted, or substituted. In some embodiments, the sequence identity comparison excludes the CDR3.

TABLE 1

Examples of anti-GITR agonist antibodies of the present invention.

| SEQ ID NO: Amino acid or polynucleotide (PN) description | Sequence |
| --- | --- |
| 61: VH, MAB1 | QVQLKESGPGLVAPSQSLSITCTVSGFSLRSYGVDWVRQPPGKGLEWLGVIWGGGGTNYNSALMAKLSISKDKSKSQVFLKMNSLQTDDTAMYYCAKHAYGHDGGFAMDYWGQGTSVTVSS |
| 59: VL, MAB1 | NIVMTQSPKSMSMSVGERVTLSCKASENVDTFVSWYQQKPDHSPKLLIYGASNRYTGVPDRFTGSGSATDFTLTISSVQAEDLADYHCGQSYSYPFTFGSGTKLEIK |
| 60: PN of VH, MAB1 encoding SEQ ID NO: 61 (VH) | CAGGTGCAGCTGAAGGAGTCAGGACCTGGCCTGGTGGCGCCCTCACAGAGCCTGTCCATCACTTGCACTGTCTCTGGGTTTTCATTAAGGAGCTATGGTGTAGACTGGGTTCGCCAGCCTCCAGGAAAGGGTCTGGAGTGGCTGGGAGTTATATGGGGTGGTGGAGGCACAAATTATAATTCAGCTCTCATGGCCAAACTGAGTATCAGCAAAGACAAGTCCAAGAGCCAAGTTTTCTTAAAAATGAACAGTCTGCAAACTGATGACACAGCCATGTACTACTGTGCCAAACATGCCTATGGTCACGACGGCGGTTTTGCTATGGACTACTGGGGTCAAGGAACCTCAGTCACCGTCTCCTCA |
| 58: PN of VL, MAB1 encoding SEQ ID NO: 59 (VL) | AACATTGTAATGACCCAATCTCCCAAATCCATGTCCATGTCAGTAGGAGAGAGGGTCACCTTGAGCTGCAAGGCCAGTGAGAATGTGGATACTTTTGTATCCTGGTATCAACAGAAACCAGACCACTCTCCTAAACTACTGATATACGGGGCATCCAACCGGTACACTGGGGTCCCCGATCGCTTCACAGGCAGTGGATCTGCAACAGATTTCACTCTGACCATCAGCAGTGTGCAGGCTGAAGACCTTGCAGATTATCACTGTGGACAGAGTTACAGCTATCCATTCACGTTCGGCTCGGGGACAAAGTTGGAAATAAAA |
| 6: VH, MAB2 | QVQLVESGGGLVQPGGSLRLSCAASGFSLSSYGVDWVRQAPGKGLEWVGVIWGGGGTYYASSVMARFTISRDNSKNTLYLQMNSLRAEDTAVYYCAKHAYGHDGGFAMDYWGQGTLVTVSS |
| 7: VL, MAB2 | EIVMTQSPATLSVSPGERATLSCRASESVSSNVAWYQQRPGQAPRLLIYGASNRATGIPARFSGSGSGTDFTLTISRLEPEDFAVYYCGQSYSYPPFTFGQGTKLEIK |

TABLE 1-continued

Examples of anti-GITR agonist antibodies of the present invention.

| SEQ ID NO: Amino acid or polynucleotide (PN) description | Sequence |
| --- | --- |
| 65: Heavy chain, MAB2 | QVQLVESGGGLVQPGGSLRLSCAASGFSLSSYGVDWVRQAPGKGLEWVGVI WGGGGTYYASSVMARFTISRDNSKNTLYLQMNSLRAEDTAVYYCAKHAYG HDGGFAMDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTYICN VNHKPSNTKVDKRVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRE EMTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 66: Light chain, MAB2 | EIVMTQSPATLSVSPGERATLSCRASESVSSNVAWYQQRPGQAPRLLIYGAS NRATGIPARFSGSGSGTDFTLTISRLEPEDFAVYYCGQSYSYPFTFGQGTKLEI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGEC |
| 51: PN of VH, MAB2 encoding SEQ ID NO: 6 | CAGGTGCAGCTGGTGGAGTCTGGGGGAGGCTTGGTACAGCCTGGGGGGT CCCTGAGACTCTCCTGTGCAGCCTCTGGATTCTCCCTCAGCAGCTATGGT GTGGACTGGGTTCGCCAGGCTCCAGGAAAGGGTCTGGAGTGGGTGGGAG TTATATGGGGTGGTGGAGGCACATATTATGCTTCTTCTGTCATGGCCAGA TTCACCATCTCCAGAGACAATTCCAAGAACACGCTGTATCTGCAAATGAA CAGCCTGAGAGCTGAGGACACGGCCGTGTATTACTGCGCCAAACATGCC TATGGCCATGATGGCGGCTTTGCTATGGATTATTGGGGCCAGGGTACCCT TGTGACCGTGAGCTCA |
| 52: PN of VL, MAB2 encoding SEQ ID NO: 7 | GAAATAGTGATGACGCAGTCTCCAGCCACCCTGTCTGTTTCTCCAGGAGA AAGAGCCACCCTCTCCTGCAGGGCCAGTGAGAGTGTTAGCAGTAATGTA GCCTGGTACCAGCAGAGACCTGGCCAGGCACCCAGGCTCCTCATCTACG GGGCATCCAACCGGGCCACTGGCATCCCAGCCAGGTTCAGTGGCAGTGG GTCTGGGACAGACTTCACTCTCACCATCAGCAGACTGGAGCCTGAAGATT TTGCAGTGTACTACTGCGGCCAGAGCTATAGCTATCCATTTACCTTTGGC CAGGGGCACCAAGCTTGAAATTAAG |
| 67: PN of HC, MAB2 encoding SEQ ID NO: 65 | CAGGTGCAGCTGGTGGAGTCTGGGGGAGGCTTGGTACAGCCTGGGGGGT CCCTGAGACTCTCCTGTGCAGCCTCTGGATTCTCCCTCAGCAGCTATGGT GTGGACTGGGTTCGCCAGGCTCCAGGAAAGGGTCTGGAGTGGGTGGGAG TTATATGGGGTGGTGGAGGCACATATTATGCTTCTTCTGTCATGGCCAGA TTCACCATCTCCAGAGACAATTCCAAGAACACGCTGTATCTGCAAATGAA CAGCCTGAGAGCTGAGGACACGGCCGTGTATTACTGCGCCAAACATGCC TATGGCCATGATGGCGGCTTTGCTATGGATTATTGGGGCCAGGGTACCCT TGTGACCGTGAGCTCAGCTAGCACCAAGGGCCCCAGCGTGTTCCCCCTGG CCCCCAGCAGCAAGAGCACCAGCGGCGGCACAGCCGCCCTGGGCTGCCT GGTGAAGGACTACTTCCCCGAGCCCGTGACCGTGTCCTGGAACAGCGGA GCCCTGACCTCCGGCGTGCACACCTTCCCCGCCGTGCTGCAGAGCAGCGG CCTGTACAGCCTGTCCAGCGTGGTGACAGTGCCCAGCAGCAGCCTGGGC ACCCAGACCTACATCTGCAACGTGAACCACAAGCCCAGCAACACCAAGG TGGACAAGAGAGTGGAGCCCAAGAGCTGCGACAAGACCCACACCTGCCC CCCCTGCCCAGCCCCAGAGCTGCTGGGCGGACCCTCCGTGTTCCTGTTCC CCCCCAAGCCCAAGGACACCCTGATGATCAGCAGGACCCCCGAGGTGAC CTGCGTGGTGGTGGACGTGAGCCACGAGGACCCAGAGGTGAAGTTCAAC TGGTACGTGGACGGCGTGGAGGTGCACAACGCCAAGACCAAGCCCAGAG AGGAGCAGTACAACAGCACCTACAGGGTGGTGTCCGTGCTGACCGTGCT GCACCAGGACTGGCTGAACGGCAAGGAATACAAGTGCAAGGTCTCCAAC AAGGCCCTGCCAGCCCCCATCGAAAAGACCATCAGCAAGGCCAAGGGCC AGCCACGGGAGCCCCAGGTGTACACCCTGCCCCCCTCCCGGGAGGAGAT GACCAAGAACCAGGTGTCCCTGACCTGTCTGGTGAAGGGCTTCTACCCCA GCGACATCGCCGTGGAGTGGGAGAGCAACGGCCAGCCCGAGAACAACTA CAAGACCACCCCCCCAGTGCTGGACAGCGACGGCAGCTTCTTCCTGTACA GCAAGCTGACCGTGGACAAGTCCAGGTGGCAGCAGGGCAACGTGTTCAG CTGCAGCGTGATGCACGAGGCCCTGCACAACCACTACACCCAGAAGAGC CTGAGCCTGTCCCCCGGCAAG |
| 68: PN of LC, MAB 2 encoding SEQ ID NO: 66 | GAAATAGTGATGACGCAGTCTCCAGCCACCCTGTCTGTTTCTCCAGGAGA AAGAGCCACCCTCTCCTGCAGGGCCAGTGAGAGTGTTAGCAGTAATGTA GCCTGGTACCAGCAGAGACCTGGCCAGGCACCCAGGCTCCTCATCTACG GGGCATCCAACCGGGCCACTGGCATCCCAGCCAGGTTCAGTGGCAGTGG GTCTGGGACAGACTTCACTCTCACCATCAGCAGACTGGAGCCTGAAGATT TTGCAGTGTACTACTGCGGCCAGAGCTATAGCTATCCATTTACCTTTGGC CAGGGGCACCAAGCTTGAAATTAAGCGTACGGTGGCCGCTCCCAGCGTGT TCATCTTCCCCCCCAGCGACGAGCAGCTGAAGAGCGGCACCGCCAGCGT GGTGTGCCTGCTGAACAACTTCTACCCCCGGGAGGCCAAGGTGCAGTGG |

TABLE 1-continued

Examples of anti-GITR agonist antibodies of the present invention.

| SEQ ID NO: Amino acid or polynucleotide (PN) description | Sequence |
|---|---|
| | AAGGTGGACAACGCCCTGCAGAGCGGCAACAGCCAGGAGAGCGTCACC GAGCAGGACAGCAAGGACTCCACCTACAGCCTGAGCAGCACCCTGACCC TGAGCAAGGCCGACTACGAGAAGCATAAGGTGTACGCCTGCGAGGTGAC CCACCAGGGCCTGTCCAGCCCCGTGACCAAGAGCTTCAACAGGGGCGAG TGC |
| 8: VH, MAB3 | QVQLVESGGGLVQPGGSLRLSCAASGFSLSSYGVDWVRQAPGKGLEWLGVI WGGGGTYYTASLMGRFTISRDNSKNTLYLQMNSLRAEDTAVYYCAKHAYG HDGGFAMDYWGQGTLVTVSS |
| 9: VL, MAB3 | EIVMTQSPATLSVSPGERATLSCRASQSVSSNLAWYQQKPGQAPRLLIYGAS NRATGIPDRFSGSGSGTDFTLTISRLEPEDFAVYYCGQSYSYPFTFGQGTKLEI K |
| 69: Heavy chain, MAB3 | QVQLVESGGGLVQPGGSLRLSCAASGFSLSSYGVDWVRQAPGKGLEWLGVI WGGGGTYYTASLMGRFTISRDNSKNTLYLQMNSLRAEDTAVYYCAKHAYG HDGGFAMDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTYICN VNHKPSNTKVDKRVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRE EMTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 70: Light chain, MAB3 | EIVMTQSPATLSVSPGERATLSCRASQSVSSNLAWYQQKPGQAPRLLIYGAS NRATGIPDRFSGSGSGTDFTLTISRLEPEDFAVYYCGQSYSYPFTFGQGTKLEI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGEC |
| 53: PN of VH, MAB3 encoding SEQ ID NO: 8 | CAGGTGCAGCTGGTGGAGTCTGGGGGAGGCTTGGTACAGCCTGGGGGGT CCCTGAGACTCTCCTGTGCAGCCTCTGGATTCTCCCTCAGCAGCTATGGT GTGGACTGGGTTCGCCAGGCTCCAGGAAAGGGTCTGGAGTGGCTGGGAG TTATATGGGGTGGTGGAGGCACATATTATACTGCTTCTCTCATGGGCAGA TTCACCATCTCCAGAGACAATTCCAAGAACACGCTGTATCTGCAAATGAA CAGCCTGAGAGCTGAGGACACGGCCGTGTATTACTGCGCCAAACATGCC TATGGCCATGATGGCGGCTTTGCTATGGATTATTGGGGCCAGGGTACCCT TGTGACCGTGAGCTCA |
| 54: PN of VL, MAB3 encoding SEQ ID NO: 9 | GAAATAGTGATGACGCAGTCTCCAGCCACCCTGTCTGTGTCTCCAGGGGA AAGAGCCACCCTCTCCTGCAGGGCCAGTCAGAGTGTTAGCAGCAACTTA GCCTGGTACCAGCAGAAACCTGGCCAGGCTCCCAGGCTCCTCATCTACGG GGCATCCAACCGGGCCACTGGCATCCCAGACAGGTTCAGTGGCAGTGGG TCTGGGACAGACTTCACTCTCACCATCAGCAGACTGGAGCCTGAAGATTT TGCAGTTTACTACTGCGGCCAGAGCTATAGCTATCCATTTACCTTTGGCC AGGGCACCAAGCTTGAAATTAAA |
| 71: PN of HC, MAB3 encoding SEQ ID NO: 69 | CAGGTGCAGCTGGTGGAGTCTGGGGGAGGCTTGGTACAGCCTGGGGGGT CCCTGAGACTCTCCTGTGCAGCCTCTGGATTCTCCCTCAGCAGCTATGGT GTGGACTGGGTTCGCCAGGCTCCAGGAAAGGGTCTGGAGTGGCTGGGAG TTATATGGGGTGGTGGAGGCACATATTATACTGCTTCTCTCATGGGCAGA TTCACCATCTCCAGAGACAATTCCAAGAACACGCTGTATCTGCAAATGAA CAGCCTGAGAGCTGAGGACACGGCCGTGTATTACTGCGCCAAACATGCC TATGGCCATGATGGCGGCTTTGCTATGGATTATTGGGGCCAGGGTACCCT TGTGACCGTGAGCTCAGCTAGCACCAAGGGCCCCAGCGTGTTCCCCCTGG CCCCCAGCAGCAAGAGCACCAGCGGCGGCACAGCCGCCCTGGGCTGCCT GGTGAAGGACTACTTCCCCGAGCCCGTGACCGTGTCCTGGAACAGCGGA GCCCTGACCTCCGGCGTGCACACCTTCCCCGCCGTGCTGCAGAGCAGCGG CCTGTACAGCCTGTCCAGCGTGGTGACAGTGCCCAGCAGCAGCCTGGGC ACCCAGACCTACATCTGCAACGTGAACCACAAGCCCAGCAACACCAAGG TGGACAAGAGAGTGGAGCCCAAGAGCTGCGACAAGACCCACACCTGCCC CCCCTGCCCAGCCCCAGAGCTGCTGGGCGGACCCTCCGTGTTCCTGTTCC CCCCCAAGCCCAAGGACACCCTGATGATCAGCAGGACCCCCGAGGTGAC CTGCGTGGTGGTGGACGTGAGCCACGAGGACCCAGAGGTGAAGTTCAAC TGGTACGTGGACGGCGTGGAGGTGCACAACGCCAAGACCAAGCCCAGAG AGGAGCAGTACAACAGCACCTACAGGGTGGTGTCCGTGCTGACCGTGCT GCACCAGGACTGGCTGAACGGCAAGGAATACAAGTGCAAGGTCTCCAAC AAGGCCCTGCCAGCCCCCATCGAAAAGACCATCAGCAAGGCCAAGGGCC AGCCACGGGAGCCCCAGGTGTACACCCTGCCCCCCTCCCGGGAGGAGAT GACCAAGAACCAGGTGTCCCTGACCTGTCTGGTGAAGGGCTTCTACCCCA GCGACATCGCCGTGGAGTGGGAGAGCAACGGCCAGCCCGAGAACAACTA CAAGACCACCCCCCCAGTGCTGGACAGCGACGGCAGCTTCTTCCTGTACA |

TABLE 1-continued

Examples of anti-GITR agonist antibodies of the present invention.

| SEQ ID NO: Amino acid or polynucleotide (PN) description | Sequence |
|---|---|
| | GCAAGCTGACCGTGGACAAGTCCAGGTGGCAGCAGGGCAACGTGTTCAG<br>CTGCAGCGTGATGCACGAGGCCCTGCACAACCACTACACCCAGAAGAGC<br>CTGAGCCTGTCCCCCGGCAAG |
| 72:PN of LC, MAB 3 encoding SEQ ID NO: 70 | GAAATAGTGATGACGCAGTCTCCAGCCACCCTGTCTGTGTCTCCAGGGGA<br>AAGAGCCACCCTCTCCTGCAGGGCCAGTCAGAGTGTTAGCAGCAACTTA<br>GCCTGGTACCAGCAGAAACCTGGCCAGGCTCCCAGGCTCCTCATCTACGG<br>GGCATCCAACCGGGCCACTGGCATCCCAGACAGGTTCAGTGGCAGTGGG<br>TCTGGGACAGACTTCACTCTCACCATCAGCAGACTGGAGCCTGAAGATTT<br>TGCAGTTTACTACTGCGGCCAGAGCTATAGCTATCCATTTACCTTTGGCC<br>AGGGCACCAAGCTTGAAATTAAACGTACGGTGGCCGCTCCCAGCGTGTT<br>CATCTTCCCCCCCAGCGACGAGCAGCTGAAGAGCGGCACCGCCAGCGTG<br>GTGTGCCTGCTGAACAACTTCTACCCCCGGGAGGCCAAGGTGCAGTGGA<br>AGGTGGACAACGCCCTGCAGAGCGGCAACAGCCAGGAGAGCGTCACCG<br>AGCAGGACAGCAAGGACTCCACCTACAGCCTGAGCAGCACCCTGACCCT<br>GAGCAAGGCCGACTACGAGAAGCATAAGGTGTACGCCTGCGAGGTGACC<br>CACCAGGGCCTGTCCAGCCCCGTGACCAAGAGCTTCAACAGGGGCGAGT<br>GC |
| 10: VH, MAB4 | EVQLVESGGGLVQSGGSLRLSCAASGFSLSSYGVDWVRQAPGKGLEWVGVI<br>WGGGGTYYASSLMGRFTISRDNSKNTLYLQMNSLRAEDTAVYYCAKHAYG<br>HDGGFAMDYWGQGTLVTVSS |
| 7: VL, MAB4 | EIVMTQSPATLSVSPGERATLSCRASESVSSNVAWYQQRPGQAPRLLIYGAS<br>NRATGIPARFSGSGSGTDFTLTISRLEPEDFAVYYCGQSYSYPFTFGQGTKLEI<br>K |
| 73: Heavy chain, MAB4 | EVQLVESGGGLVQSGGSLRLSCAASGFSLSSYGVDWVRQAPGKGLEWVGVI<br>WGGGGTYYASSLMGRFTISRDNSKNTLYLQMNSLRAEDTAVYYCAKHAYG<br>HDGGFAMDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTYICN<br>VNHKPSNTKVDKRVEPKSCDKTHTCPPCPAPELLGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSRE<br>EMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 66: Light chain, MAB4 | EIVMTQSPATLSVSPGERATLSCRASESVSSNVAWYQQRPGQAPRLLIYGAS<br>NRATGIPARFSGSGSGTDFTLTISRLEPEDFAVYYCGQSYSYPFTFGQGTKLEI<br>KRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSF<br>NRGEC |
| 55: PN of VH, MAB4 encoding SEQ ID NO: 10 | GAGGTGCAGCTGGTGGAGTCCGGGGGAGGCTTAGTTCAGTCTGGGGGGT<br>CCCTGAGACTCTCCTGTGCAGCCTCTGGATTCTCCCTCAGCAGCTATGGT<br>GTGGACTGGGTTCGCCAGGCTCCAGGGAAAGGGTCTGGAGTGGGTGGGAG<br>TTATATGGGGTGGTGGAGGCACATATTATGCTTCTTCTCTCATGGGCAGA<br>TTCACCATCTCCAGAGACAATTCCAAGAACACGCTGTATCTGCAAATGAA<br>CAGCCTGAGAGCTGAGGACACGGCCGTGTATTACTGCGCCAAACATGCC<br>TATGGCCATGATGGCGGCTTTGCTATGGATTATTGGGGCCAGGGTACCCT<br>TGTGACCGTGAGCTCA |
| 52: PN of VL, MAB4 encoding SEQ ID NO: 7 | GAAATAGTGATGACGCAGTCTCCAGCCACCCTGTCTGTTTCTCCAGGAGA<br>AAGAGCCACCCTCTCCTGCAGGGCCAGTGAGAGTGTTAGCAGTAATGTA<br>GCCTGGTACCAGCAGAGACCTGGCCAGGCACCCAGGCTCCTCATCTACG<br>GGGCATCCAACCGGGCCACTGGCATCCCAGCCAGGTTCAGTGGCAGTGG<br>GTCTGGGACAGACTTCACTCTCACCATCAGCAGACTGGAGCCTGAAGATT<br>TTGCAGTGTACTACTGCGGCCAGAGCTATAGCTATCCATTTACCTTTGGC<br>CAGGGCACCAAGCTTGAAATTAAG |
| 74:PN of HC, MAB4 encoding SEQ ID NO: 73 | GAGGTGCAGCTGGTGGAGTCCGGGGGAGGCTTAGTTCAGTCTGGGGGGT<br>CCCTGAGACTCTCCTGTGCAGCCTCTGGATTCTCCCTCAGCAGCTATGGT<br>GTGGACTGGGTTCGCCAGGCTCCAGGGAAAGGGTCTGGAGTGGGTGGGAG<br>TTATATGGGGTGGTGGAGGCACATATTATGCTTCTTCTCTCATGGGCAGA<br>TTCACCATCTCCAGAGACAATTCCAAGAACACGCTGTATCTGCAAATGAA<br>CAGCCTGAGAGCTGAGGACACGGCCGTGTATTACTGCGCCAAACATGCC<br>TATGGCCATGATGGCGGCTTTGCTATGGATTATTGGGGCCAGGGTACCCT<br>TGTGACCGTGAGCTCAGCTAGCACCAAGGGCCCCAGCGTGTTCCCCCTGG<br>CCCCCAGCAGCAAGAGCACCAGCGGCGGCACAGCCGCCCTGGGCTGCCT<br>GGTGAAGGACTACTTCCCCGAGCCCGTGACCGTGTCCTGGAACAGCGGA<br>GCCCTGACCTCCGGCGTGCACACCTTCCCCGCCGTGCTGCAGAGCAGCGG<br>CCTGTACAGCCTGTCCAGCGTGGTGACAGTGCCCAGCAGCAGCCTGGGC |

TABLE 1-continued

Examples of anti-GITR agonist antibodies of the present invention.

| SEQ ID NO: Amino acid or polynucleotide (PN) description | Sequence |
| --- | --- |
| | ACCCAGACCTACATCTGCAACGTGAACCACAAGCCCAGCAACACCAAGG<br>TGGACAAGAGAGTGGAGCCCAAGAGCTGCGACAAGACCCACACCTGCCC<br>CCCCTGCCCAGCCCCAGAGCTGCTGGGCGGACCCTCCGTGTTCCTGTTCC<br>CCCCCAAGCCCAAGGACACCCTGATGATCAGCAGGACCCCCGAGGTGAC<br>CTGCGTGGTGGTGGACGTGAGCCACGAGGACCCAGAGGTGAAGTTCAAC<br>TGGTACGTGGACGGCGTGGAGGTGCACAACGCCAAGACCAAGCCCAGAG<br>AGGAGCAGTACAACAGCACCTACAGGGTGGTGTCCGTGCTGACCGTGCT<br>GCACCAGGACTGGCTGAACGGCAAGGAATACAAGTGCAAGGTCTCCAAC<br>AAGGCCCTGCCAGCCCCCATCGAAAAGACCATCAGCAAGGCCAAGGGCC<br>AGCCACGGGAGCCCCAGGTGTACACCCTGCCCCCCTCCCGGGAGGAGAT<br>GACCAAGAACCAGGTGTCCCTGACCTGTCTGGTGAAGGGCTTCTACCCCA<br>GCGACATCGCCGTGGAGTGGGAGAGCAACGGCCAGCCCGAGAACAACTA<br>CAAGACCACCCCCCCAGTGCTGGACAGCGACGGCAGCTTCTTCCTGTACA<br>GCAAGCTGACCGTGGACAAGTCCAGGTGGCAGCAGGGCAACGTGTTCAG<br>CTGCAGCGTGATGCACGAGGCCCTGCACAACCACTACACCCAGAAGAGC<br>CTGAGCCTGTCCCCCGGCAAG |
| 68: PN of LC, MAB4 encoding SEQ ID NO: 66 | GAAATAGTGATGACGCAGTCTCCAGCCACCCTGTCTGTTTCTCCAGGAGA<br>AAGAGCCACCCTCTCCTGCAGGGCCAGTGAGAGTGTTAGCAGTAATGTA<br>GCCTGGTACCAGCAGAGACCTGGCCAGGCACCCAGGCTCCTCATCTACG<br>GGGCATCCAACCGGGCCACTGGCATCCCAGCCAGGTTCAGTGGCAGTGG<br>GTCTGGGACAGACTTCACTCTCACCATCAGCAGACTGGAGCCTGAAGATT<br>TTGCAGTGTACTACTGCGGCCAGAGCTATAGCTATCCATTTACCTTTGGC<br>CAGGGCACCAAGCTTGAAATTAAGCGTACGGTGGCCGCTCCCAGCGTGT<br>TCATCTTCCCCCCCAGCGACGAGCAGCTGAAGAGCGGCACCGCCAGCGT<br>GGTGTGCCTGCTGAACAACTTCTACCCCCGGGAGGCCAAGGTGCAGTGG<br>AAGGTGGACAACGCCCTGCAGAGCGGCAACAGCCAGGAGAGCGTCACC<br>GAGCAGGACAGCAAGGACTCCACCTACAGCCTGAGCAGCACCCTGACCC<br>TGAGCAAGGCCGACTACGAGAAGCATAAGGTGTACGCCTGCGAGGTGAC<br>CCACCAGGGCCTGTCCAGCCCCGTGACCAAGAGCTTCAACAGGGGCGAG<br>TGC |
| 12: VH, MAB5 | EVQLVESGGGLVQSGGSLRLSCAASGFSLSSYGVDWVRQAPGKGLEWLGVI<br>WGGGGTYYTSSLMGRFTISRDNSKNTLYLQMNSLRAEDTAVYYCAKHAYG<br>HDGGFAMDYWGQGTLVTVSS |
| 7: VL, MAB5 | EIVMTQSPATLSVSPGERATLSCRASESVSSNVAWYQQRPGQAPRLLIYGAS<br>NRATGIPARFSGSGSGTDFTLTISRLEPEDFAVYYCGQSYSYPFTFGQGTKLEI<br>K |
| 75: Heavy chain, MAB5 | EVQLVESGGGLVQSGGSLRLSCAASGFSLSSYGVDWVRQAPGKGLEWLGVI<br>WGGGGTYYTSSLMGRFTISRDNSKNTLYLQMNSLRAEDTAVYYCAKHAYG<br>HDGGFAMDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTYICN<br>VNHKPSNTKVDKRVEPKSCDKTHTCPPCPAPELLGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSRE<br>EMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 66: Light chain, MAB5 | EIVMTQSPATLSVSPGERATLSCRASESVSSNVAWYQQRPGQAPRLLIYGAS<br>NRATGIPARFSGSGSGTDFTLTISRLEPEDFAVYYCGQSYSYPFTFGQGTKLEI<br>KRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSF<br>NRGEC |
| 56: PN of VH, MAB5 encoding SEQ ID NO: 12 | GAGGTGCAGCTGGTGGAGTCCGGGGGAGGCTTAGTTCAGTCTGGGGGGT<br>CCCTGAGACTCTCCTGTGCAGCCTCTGGATTCTCCCTCAGCAGCTATGGT<br>GTGGACTGGGTTCGCCAGGCTCCAGGAAAGGGTCTGGAGTGGCTGGGAG<br>TTATATGGGGTGGTGGAGGCACATATTATACTTCTTCTCTCATGGGCAGA<br>TTCACCATCTCCAGAGACAATTCCAAGAACACGCTGTATCTGCAAATGAA<br>CAGCCTGAGAGCTGAGGACACGGCCGTGTATTACTGCGCCAAACATGCC<br>TATGCCCATGATGGCGGCTTTGCTATGGATTATTGGGGCCAGGGTACCCT<br>TGTGACCGTGAGCTCA |
| 52: PN of VL, MAB5 encoding SEQ ID NO: 7 | GAAATAGTGATGACGCAGTCTCCAGCCACCCTGTCTGTTTCTCCAGGAGA<br>AAGAGCCACCCTCTCCTGCAGGGCCAGTGAGAGTGTTAGCAGTAATGTA<br>GCCTGGTACCAGCAGAGACCTGGCCAGGCACCCAGGCTCCTCATCTACG<br>GGGCATCCAACCGGGCCACTGGCATCCCAGCCAGGTTCAGTGGCAGTGG<br>GTCTGGGACAGACTTCACTCTCACCATCAGCAGACTGGAGCCTGAAGATT<br>TTGCAGTGTACTACTGCGGCCAGAGCTATAGCTATCCATTTACCTTTGGC<br>CAGGGCACCAAGCTTGAAATTAAG |

TABLE 1-continued

Examples of anti-GITR agonist antibodies of the present invention.

| SEQ ID NO: Amino acid or polynucleotide (PN) description | Sequence |
| --- | --- |
| 76: PN of HC, MAB5 encoding SEQ ID NO: 75 | GAGGTGCAGCTGGTGGAGTCCGGGGGAGGCTTAGTTCAGTCTGGGGGGT CCCTGAGACTCTCCTGTGCAGCCTCTGGATTCTCCCTCAGCAGCTATGTT GTGGACTGGGTTCGCCAGGCTCCAGGAAAGGGTCTGGAGTGGCTGGGAG TTATATGGGGTGGTGGAGGCACATATTATACTTCTTCTCTCATGGGCAGA TTCACCATCTCCAGAGACAATTCCAAGAACACGCTGTATCTGCAAATGAA CAGCCTGAGAGCTGAGGACACGGCCGTGTATTACTGCGCCAAACATGCC TATGGCCATGATGGCGGCTTTGCTATGGATTATTGGGGCCAGGGTACCCT TGTGACCGTGAGCTCAGCTAGCACCAAGGGCCCCAGCGTGTTCCCCCTGG CCCCCAGCAGCAAGAGCACCAGCGGCGGCACAGCCGCCCTGGGCTGCCT GGTGAAGGACTACTTCCCCGAGCCCGTGACCGTGTCCTGGAACAGCGGA GCCCTGACCTCCGGCGTGCACACCTTCCCCGCCGTGCTGCAGAGCAGCGG CCTGTACAGCCTGTCCAGCGTGGTGACAGTGCCCAGCAGCAGCCTGGGC ACCCAGACCTACATCTGCAACGTGAACCACAAGCCCAGCAACACCAAGG TGGACAAGAGAGTGGAGCCCAAGAGCTGCGACAAGACCCACACCTGCCC CCCCTGCCCAGCCCCAGAGCTGCTGGGCGGACCCTCCGTGTTCCTGTTCC CCCCCAAGCCCAAGGACACCCTGATGATCAGCAGGACCCCCGAGGTGAC CTGCGTGGTGGTGGACGTGAGCCACGAGGACCCAGAGGTGAAGTTCAAC TGGTACGTGGACGGCGTGGAGGTGCACAACGCCAAGACCAAGCCCAGAG AGGAGCAGTACAACAGCACCTACAGGGTGGTGTCCGTGCTGACCGTGCT GCACCAGGACTGGCTGAACGGCAAGGAATACAAGTGCAAGGTCTCCAAC AAGGCCCTGCCAGCCCCCATCGAAAAGACCATCAGCAAGGCCAAGGGCC AGCCACGGGAGCCCCAGGTGTACACCCTGCCCCCCTCCCGGGAGGAGAT GACCAAGAACCAGGTGTCCCTGACCTGTCTGGTGAAGGGCTTCTACCCCA GCGACATCGCCGTGGAGTGGGAGAGCAACGGCCAGCCCGAGAACAACTA CAAGACCACCCCCCCAGTGCTGGACAGCGACGGCAGCTTCTTCCTGTACA GCAAGCTGACCGTGGACAAGTCCAGGTGGCAGCAGGGCAACGTGTTCAG CTGCAGCGTGATGCACGAGGCCCTGCACAACCACTACACCCAGAAGAGC CTGAGCCTGTCCCCCGGCAAG |
| 68: PN of LC, MAB5 encoding SEQ ID NO: 66 | GAAATAGTGATGACGCAGTCTCCAGCCACCCTGTCTGTTTCTCCAGGAGA AAGAGCCACCCTCTCCTGCAGGGCCAGTGAGAGTGTTAGCAGTAATGTA GCCTGGTACCAGCAGAGACCTGGCCAGGCACCCAGGCTCCTCATCTACG GGGCATCCAACCGGGCCACTGGCATCCCAGCCAGGTTCAGTGGCAGTGG GTCTGGGACAGACTTCACTCTCACCATCAGCAGACTGGAGCCTGAAGATT TTGCAGTGTACTACTGCGGCCAGAGCTATAGCTATCCATTTACCTTTGGC CAGGGCACCAAGCTTGAAATTAAGCGTACGGTGGCCGCTCCCAGCGTGT TCATCTTCCCCCCCAGCGACGAGCAGCTGAAGAGCGGCACCGCCAGCGT GGTGTGCCTGCTGAACAACTTCTACCCCCGGGAGGCCAAGGTGCAGTGG AAGGTGGACAACGCCCTGCAGAGCGGCAACAGCCAGGAGAGCGTCACC GAGCAGGACAGCAAGGACTCCACCTACAGCCTGAGCAGCACCCTGACCC TGAGCAAGGCCGACTACGAGAAGCATAAGGTGTACGCCTGCGAGGTGAC CCACCAGGGCCTGTCCAGCCCCGTGACCAAGAGCTTCAACAGGGGCGAG TGC |
| 14: VH, MAB6 | EVQLVESGGGLVQSGGSLRLSCAASGFSLSSYGVDWVRQAPGKGLEWLGVI WGGGGTYYTSSLMARFTISRDNSKNTLYLQMNSLRAEDTAVYYCAKHAYG HDGGFAMDYWGQGTLVTVSS |
| 7: VL, MAB6 | EIVMTQSPATLSVSPGERATLSCRASESVSSNVAWYQQRPGQAPRLLIYGAS NRATGIPARFSGSGSGTDFTLTISRLEPEDFAVYYCGQSYSYPPTFGQGTKLEI K |
| 77: Heavy chain, MAB6 | EVQLVESGGGLVQSGGSLRLSCAASGFSLSSYGVDWVRQAPGKGLEWLGVI WGGGGTYYTSSLMARFTISRDNSKNTLYLQMNSLRAEDTAVYYCAKHAYG HDGGFAMDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTYIC VNHKPSNTKVDKRVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRE EMTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 66: Light chain, MAB6 | EIVMTQSPATLSVSPGERATLSCRASESVSSNVAWYQQRPGQAPRLLIYGAS NRATGIPARFSGSGSGTDFTLTISRLEPEDFAVYYCGQSYSYPPTFGQGTKLEI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGEC |

TABLE 1-continued

Examples of anti-GITR agonist antibodies of the present invention.

| SEQ ID NO: Amino acid or polynucleotide (PN) description | Sequence |
| --- | --- |
| 57: PN of VH, MAB6 encoding SEQ ID NO: 14 | GAGGTGCAGCTGGTGGAGTCCGGGGGAGGCTTAGTTCAGTCTGGGGGGT<br>CCCTGAGACTCTCCTGTGCAGCCTCTGGATTCTCCCTCAGCAGCTATGGT<br>GTGGACTGGGTTCGCCAGGCTCCAGGAAAGGGTCTGGAGTGGCTGGGAG<br>TTATATGGGGTTGGTGGAGGCACATATTATACTTCTTCTCTCATGGCCAGA<br>TTCACCATCTCCAGAGACAATTCCAAGAACACGCTGTATCTGCAAATGAA<br>CAGCCTGAGAGCTGAGGACACGGCCGTGTATTACTGCGCCAAACATGCC<br>TATGGCCATGATGGCGGCTTTGCTATGGATTATTGGGGCCAGGGTACCCT<br>TGTGACCGTGAGCTCA |
| 52: PN of VL, MAB6 encoding SEQ ID NO: 7 | GAAATAGTGATGACGCAGTCTCCAGCCACCCTGTCTGTTTCTCCAGGAGA<br>AAGAGCCACCCTCTCCTGCAGGGCCAGTGAGAGTGTTAGCAGTAATGTA<br>GCCTGGTACCAGCAGAGACCTGGCCAGGCACCCAGGCTCCTCATCTACG<br>GGGCATCCAACCGGGCCACTGGCATCCCAGCCAGGTTCAGTGGCAGTGG<br>GTCTGGGACAGACTTCACTCTCACCATCAGCAGACTGGAGCCTGAAGATT<br>TTGCAGTGTACTACTGCGGCCAGAGCTATAGCTATCCATTTACCTTTGGC<br>CAGGGCACCAAGCTTGAAATTAAG |
| 78: PN of HC, MAB6 encoding SEQ ID NO: 77 | GAGGTGCAGCTGGTGGAGTCCGGGGGAGGCTTAGTTCAGTCTGGGGGGT<br>CCCTGAGACTCTCCTGTGCAGCCTCTGGATTCTCCCTCAGCAGCTATGGT<br>GTGGACTGGGTTCGCCAGGCTCCAGGAAAGGGTCTGGAGTGGCTGGGAG<br>TTATATGGGGTTGGTGGAGGCACATATTATACTTCTTCTCTCATGGCCAGA<br>TTCACCATCTCCAGAGACAATTCCAAGAACACGCTGTATCTGCAAATGAA<br>CAGCCTGAGAGCTGAGGACACGGCCGTGTATTACTGCGCCAAACATGCC<br>TATGGCCATGATGGCGGCTTTGCTATGGATTATTGGGGCCAGGGTACCCT<br>TGTGACCGTGAGCTCAGCTAGCACCAAGGGCCCCAGCGTGTTCCCCCTGG<br>CCCCCAGCAGCAAGAGCACCAGCGGCGGCACAGCCGCCCTGGGCTGCCT<br>GGTGAAGGACTACTTCCCCGAGCCCGTGACCGTGTCCTGGAACAGCGGA<br>GCCCTGACCTCCGGCGTGCACACCTTCCCCGCCGTGCTGCAGAGCAGCGG<br>CCTGTACAGCCTGTCCAGCGTGGTGACAGTGCCCAGCAGCAGCCTGGGC<br>ACCCAGACCTACATCTGCAACGTGAACCACAAGCCCAGCAACACCAAGG<br>TGGACAAGAGAGTGGAGCCCAAGAGCTGCGACAAGACCCACACCTGCCC<br>CCCCTGCCCAGCCCCAGAGCTGCTGGGCGGACCCTCCGTGTTCCTGTTCC<br>CCCCCAAGCCCAAGGACACCCTGATGATCAGCAGGACCCCCGAGGTGAC<br>CTGCGTGGTGGTGGACGTGAGCCACGAGGACCCAGAGGTGAAGTTCAAC<br>TGGTACGTGGACGGCGTGGAGGTGCACAACGCCAAGACCAAGCCCAGAG<br>AGGAGCAGTACAACAGCACCTACAGGGTGGTGTCCGTGCTGACCGTGCT<br>GCACCAGGACTGGCTGAACGGCAAGGAATACAAGTGCAAGGTCTCCAAC<br>AAGGCCCTGCCAGCCCCCATCGAAAAGACCATCAGCAAGGCCAAGGGCC<br>AGCCACGGGAGCCCCAGGTGTACACCCTGCCCCCCTCCCGGGAGGAGAT<br>GACCAAGAACCAGGTGTCCCTGACCTGTCTGGTGAAGGGCTTCTACCCCA<br>GCGACATCGCCGTGGAGTGGGAGAGCAACGGCCAGCCCGAGAACAACTA<br>CAAGACCACCCCCCCAGTGCTGGACAGCGACGGCAGCTTCTTCCTGTACA<br>GCAAGCTGACCGTGGACAAGTCCAGGTGGCAGCAGGGCAACGTGTTCAG<br>CTGCAGCGTGATGCACGAGGCCCTGCACAACCACTACACCCAGAAGAGC<br>CTGAGCCTGTCCCCCGGCAAG |
| 68: PN of LC, MAB6 encoding SEQ ID NO: 66 | GAAATAGTGATGACGCAGTCTCCAGCCACCCTGTCTGTTTCTCCAGGAGA<br>AAGAGCCACCCTCTCCTGCAGGGCCAGTGAGAGTGTTAGCAGTAATGTA<br>GCCTGGTACCAGCAGAGACCTGGCCAGGCACCCAGGCTCCTCATCTACG<br>GGGCATCCAACCGGGCCACTGGCATCCCAGCCAGGTTCAGTGGCAGTGG<br>GTCTGGGACAGACTTCACTCTCACCATCAGCAGACTGGAGCCTGAAGATT<br>TTGCAGTGTACTACTGCGGCCAGAGCTATAGCTATCCATTTACCTTTGGC<br>CAGGGCACCAAGCTTGAAATTAAGCGTACGGTGGCCGCTCCCAGCGTGT<br>TCATCTTCCCCCCCAGCGACGAGCAGCTGAAGAGCGGCACCGCCAGCGT<br>GGTGTGCCTGCTGAACAACTTCTACCCCGGGAGGCCAAGGTGCAGTGG<br>AAGGTGGACAACGCCCTGCAGAGCGGCAACAGCCAGGAGAGCGTCACC<br>GAGCAGGACAGCAAGGACTCCACCTACAGCCTGAGCAGCACCCTGACCC<br>TGAGCAAGGCCGACTACGAGAAGCATAAGGTGTACGCCTGCGAGGTGAC<br>CCACCAGGGCCTGTCCAGCCCCGTGACCAAGAGCTTCAACAGGGGCGAG<br>TGC |
| 99: VH, MAB7 | EVQLVESGGGLVQSGGSLRLSCAASGFSLSSYGVDWVRQAPGKGLEWVGVI<br>WGGGGTYYASSLMGRFTISRDNSKNTLYLQMNSLRAEDTAVYYCARHAYG<br>HDGGFAMDYWGQGTLVTVSS |
| 7: VL, MAB7 | EIVMTQSPATLSVSPGERATLSCRASESVSSNVAWYQQRPGQAPRLLIYGAS<br>NRATGIPARFSGSGSGTDFTLTISRLEPEDFAVYYCGQSYSYPFTFGQGTKLEI<br>K |

TABLE 1-continued

Examples of anti-GITR agonist antibodies of the present invention.

| SEQ ID NO: Amino acid or polynucleotide (PN) description | Sequence |
| --- | --- |
| 100: Heavy chain, MAB7 | EVQLVESGGGLVQSGGSLRLSCAASGFSLSSYGVDWVRQAPGKGLEWVGVI WGGGGTYYASSLMGRFTISRDNSKNTLYLQMNSLRAEDTAVYYCARHAYG HDGGFAMDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTYICN VNHKPSNTKVDKRVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRE EMTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 66: Light chain, MAB7 | EIVMTQSPATLSVSPGERATLSCRASESVSSNVAWYQQRPGQAPRLLIYGAS NRATGIPARFSGSGSGTDFTLTISRLEPEDFAVYYCGQSYSYPPTFGQGTKLEI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSF NRGEC |
| 101: PN of VH, MAB7 encoding SEQ ID NO: 99 | GAGGTGCAGCTGGTGGAATCTGGCGGCGGACTGGTGCAGTCCGGCGGCT CTCTGAGACTGTCTTGCGCTGCCTCCGGCTTCTCCCTGTCCTCTTACGGCG TGGACTGGGTGCGACAGGCCCCTGGCAAGGGCCTGGAATGGGTGGGAGT GATCTGGGGCGGAGGCGGCACCTACTACGCCTCTTCCCTGATGGGCCGGT TCACCATCTCCCGGGACAACTCCAAGAACACCCTGTACCTGCAGATGAAC TCCCTGCGGGCCGAGGACACCGCCGTGTACTACTGCGCCAGACACGCCT ACGGCCACGACGGCGGCTTCGCCATGGATTATTGGGGCCAGGGCACCCT GGTGACAGTGTCCTCC |
| 102: PN of VL, MAB7 encoding SEQ ID NO: 7 | GAGATCGTGATGACCCAGTCCCCCGCCACCCTGTCTGTGTCTCCCGGCGA GAGAGCCACCCTGAGCTGCAGAGCCTCCGAGTCCGTGTCCTCCAACGTG GCCTGGTATCAGCAGAGACCTGGTCAGGCCCCTCGGCTGCTGATCTACGG CGCCTCTAACCGGGCCACCGGCATCCCTGCCAGATTCTCCGGCTCCGGCA GCGGCACCGACTTCACCCTGACCATCTCCCGGCTGGAACCCGAGGACTTC GCCGTGTACTACTGCGGCCAGTCCTACTCATACCCCTTCACCTTCGGCCA GGGCACCAAGCTGGAAATCAAG |
| 103: PN of HC, MAB7 encoding SEQ ID NO: 100 | GAGGTGCAGCTGGTGGAATCTGGCGGCGGACTGGTGCAGTCCGGCGGCT CTCTGAGACTGTCTTGCGCTGCCTCCGGCTTCTCCCTGTCCTCTTACGGCG TGGACTGGGTGCGACAGGCCCCTGGCAAGGGCCTGGAATGGGTGGGAGT GATCTGGGGCGGAGGCGGCACCTACTACGCCTCTTCCCTGATGGGCCGGT TCACCATCTCCCGGGACAACTCCAAGAACACCCTGTACCTGCAGATGAAC TCCCTGCGGGCCGAGGACACCGCCGTGTACTACTGCGCCAGACACGCCT ACGGCCACGACGGCGGCTTCGCCATGGATTATTGGGGCCAGGGCACCCT GGTGACAGTGTCCTCCGCTAGCACCAAGGGCCCAAGTGTGTTTCCCCTGG CCCCCAGCAGCAAGTCTACTTCCGGCGGAACTGCTGCCCTGGGTTGCCTG GTGAAGGACTACTTCCCCGAGCCCGTGACAGTGTCCTGGAACTCTGGGGC TCTGACTTCCGGCGTGCACACCTTCCCCGCCGTGCTGCAGAGCAGCGGCC TGTACAGCCTGAGCAGCGTGGTGACAGTGCCCTCCAGCTCTCTGGGAACC CAGACCTATATCTGCAACGTGAACCACAAGCCCAGCAACACCAAGGTGG ACAAGAGAGTGGAGCCCAAGAGCTGCGACAAGACCCACACCTGCCCCCC CTGCCCAGCTCCAGAACTGCTGGGAGGGCCTTCCGTGTTCCTGTTCCCCC CAAGCCCAAGGACACCCTGATGATCAGCAGGACCCCCGAGGTGACCTG CGTGGTGGTGGACGTGTCCCACGAGGACCCAGAGGTGAAGTTCAACTGG TACGTGGACGGCGTGGAGGTGCACAACGCCAAGACCAAGCCCAGAGAG GAGCAGTACAACAGCACCTACAGGGTGGTGTCCGTGCTGACCGTGCTGC ACCAGGACTGGCTGAACGGCAAAGAATACAAGTGCAAAGTCTCCAACAA GGCCCTGCCAGCCCCAATCGAAAAGACAATCAGCAAGGCCAAGGGCCAG CCACGGGAGCCCCAGGTGTACACCCTGCCCCCCAGCCGGGAGGAGATGA CCAAGAACCAGGTGTCCCTGACCTGTCTGGTGAAGGGCTTCTACCCCAGC GATATCGCCGTGGAGTGGGAGAGCAACGGCCAGCCCGAGAACAACTACA AGACCACCCCCCCAGTGCTGGACAGCGACGGCAGCTTCTTCCTGTACAGC AAGCTGACCGTGGACAAGTCCAGGTGGCAGCAGGGCAACGTGTTCAGCT GCAGCGTGATGCACGAGGCCCTGCACAACCACTACACCCAGAAGTCCCT GAGCCTGAGCCCCGGCAAG |
| 104: PN of LC, MAB7 encoding SEQ ID NO: 66 | GAGATCGTGATGACCCAGTCCCCCGCCACCCTGTCTGTGTCTCCCGGCGA GAGAGCCACCCTGAGCTGCAGAGCCTCCGAGTCCGTGTCCTCCAACGTG GCCTGGTATCAGCAGAGACCTGGTCAGGCCCCTCGGCTGCTGATCTACGG CGCCTCTAACCGGGCCACCGGCATCCCTGCCAGATTCTCCGGCTCCGGCA GCGGCACCGACTTCACCCTGACCATCTCCCGGCTGGAACCCGAGGACTTC GCCGTGTACTACTGCGGCCAGTCCTACTCATACCCCTTCACCTTCGGCCA GGGCACCAAGCTGGAAATCAAGCGTACGGTGGCCGCTCCCAGCGTGTTC ATCTTCCCCCCCAGCGACGAGCAGCTGAAGAGCGGCACCGCCAGCGTGG TGTGCCTGCTGAACAACTTCTACCCCCGGGAGGCCAAGGTGCAGTGGAA |

TABLE 1-continued

Examples of anti-GITR agonist antibodies of the present invention.

| SEQ ID NO: Amino acid or polynucleotide (PN) description | Sequence |
| --- | --- |
| | GGTGGACAACGCCCTGCAGAGCGGCAACAGCCAGGAGAGCGTCACCGA<br>GCAGGACAGCAAGGACTCCACCTACAGCCTGAGCAGCACCCTGACCCTG<br>AGCAAGGCCGACTACGAGAAGCATAAGGTGTACGCCTGCGAGGTGACCC<br>ACCAGGGCCTGTCCAGCCCCGTGACCAAGAGCTTCAACAGGGGCGAGTG<br>C |
| 105: VH, MAB8 | EVQLVESGGGLVQSGGSLRLSCAASGFSLSSYGVDWVRQAPGKGLEWVGVI<br>WGGGGTYYASSLMGRFTISRDNSKNTLYLQMNSLRAEDTAVYYCARNAYG<br>HDGGFAMDYWGQGTLVTVSS |
| 7: VL, MAB8 | EIVMTQSPATLSVSPGERATLSCRASESVSSNVAWYQQRPGQAPRLLIYGAS<br>NRATGIPARFSGSGSGTDFTLTISRLEPEDFAVYYCGQSYSYPFTFGQGTKLEI<br>K |
| 106: Heavy chain, MAB8 | EVQLVESGGGLVQSGGSLRLSCAASGFSLSSYGVDWVRQAPGKGLEWVGVI<br>WGGGGTYYASSLMGRFTISRDNSKNTLYLQMNSLRAEDTAVYYCARNAYG<br>HDGGFAMDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTYICN<br>VNHKPSNTKVDKRVEPKSCDKTHTCPPCPAPELLGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSRE<br>EMTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 66: Light chain, MAB8 | EIVMTQSPATLSVSPGERATLSCRASESVSSNVAWYQQRPGQAPRLLIYGAS<br>NRATGIPARFSGSGSGTDFTLTISRLEPEDFAVYYCGQSYSYPFTFGQGTKLEI<br>KRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSF<br>NRGEC |
| 107: PN of VH, MAB8 encoding SEQ ID NO: 105 | GAGGTGCAGCTGGTGGAATCAGGCGGCGGACTGGTGCAGTCAGGCGGTA<br>GCCTGAGACTGAGCTGCGCCGCCTCCGGCTTTAGCCTGTCTAGCTACGGC<br>GTGGACTGGGTCCGACAGGCCCCTGGCAAAGGCCTGGAGTGGGTCGGAG<br>TGATCTGGGGCGGAGGCGGAACCTACTACGCCTCTAGCCTGATGGGCCG<br>GTTCACTATCTCTAGGGACAACTCTAAGAACACCCTGTACCTGCAGATGA<br>ACTCACTGAGAGCCGAGGACACCGCCGTCTACTACTGCGCTAGAAACGC<br>CTACGGTCACGACGGCGGCTTCGCTATGGACTACTGGGGTCAGGGCACC<br>CTGGTCACCGTGAGTTCA |
| 102: PN of VL, MAB8 encoding SEQ ID NO: 7 | GAGATCGTGATGACCCAGTCCCCCGCCACCCTGTCTGTGTCTCCCGGCGA<br>GAGAGCCACCCTGAGCTGCAGAGCCTCCGAGTCCGTGTCCTCCAACGTG<br>GCCTGGTATCAGCAGAGACCTGGTCAGGCCCCTCGGCTGCTGATCTACGG<br>CGCCTCTAACCGGGCCACCGGCATCCCTGCCAGATTCTCCGGCTCCGGCA<br>GCGGCACCGACTTCACCCTGACCATCTCCCGGCTGGAACCCGAGGACTTC<br>GCCGTGTACTACTGCGGCCAGTCCTACTCATACCCCTTCACCTTCGGCCA<br>GGGCACCAAGCTGGAAATCAAG |
| 108: PN of HC, MAB8 encoding SEQ ID NO: 106 | GAGGTGCAGCTGGTGGAATCAGGCGGCGGACTGGTGCAGTCAGGCGGTA<br>GCCTGAGACTGAGCTGCGCCGCCTCCGGCTTTAGCCTGTCTAGCTACGGC<br>GTGGACTGGGTCCGACAGGCCCCTGGCAAAGGCCTGGAGTGGGTCGGAG<br>TGATCTGGGGCGGAGGCGGAACCTACTACGCCTCTAGCCTGATGGGCCG<br>GTTCACTATCTCTAGGGACAACTCTAAGAACACCCTGTACCTGCAGATGA<br>ACTCACTGAGAGCCGAGGACACCGCCGTCTACTACTGCGCTAGAAACGC<br>CTACGGTCACGACGGCGGCTTCGCTATGGACTACTGGGGTCAGGGCACC<br>CTGGTCACCGTGAGTTCAGCTAGCACTAAGGGCCCAAGTGTGTTTCCCCT<br>GGCCCCCAGCAGCAAGTCTACTTCCGGCGGAACTGCTGCCCTGGGTTGCC<br>TGGTGAAGGACTACTTCCCCGAGCCCGTGACAGTGTCCTGGAACTCTGGG<br>GCTCTGACTTCCGGCGTGCACACCTTCCCCGCCGTGCTGCAGAGCAGCGG<br>CCTGTACAGCCTGAGCAGCGTGGTGACAGTGCCCTCCAGCTCTCTGGGAA<br>CCCAGACCTATATCTGCAACGTGAACCACAAGCCCAGCAACACCAAGGT<br>GGACAAGAGAGTGGAGCCCAAGAGCTGCGACAAGACCCACACCTGCCCC<br>CCCTGCCCAGCTCCAGAACTGCTGGGAGGGCCTTCCGTGTTCCTGTTCCC<br>CCCCAAGCCCAAGGACACCCTGATGATCAGCAGGACCCCCGAGGTGACC<br>TGCGTGGTGGTGGACGTGTCCCACGAGGACCCAGAGGTGAAGTTCAACT<br>GGTACGTGGACGGCGTGGAGGTGCACAACGCCAAGACCAAGCCCAGAG<br>AGGAGCAGTACAACAGCACCTACAGGGTGGTGTCCGTGCTGACCGTGCT<br>GCACCAGGACTGGCTGAACGGCAAGAATACAAGTGCAAAGTCTCCAAC<br>AAGGCCCTGCCAGCCCCAATCGAAAAGACAATCAGCAAGGCCAAGGGCC<br>AGCCACGGGAGCCCCAGGTGTACACCCTGCCCCCCAGCCGGGAGGAGAT<br>GACCAAGAACCAGGTGTCCCTGACCTGTCTGGTGAAGGGCTTCTACCCCA<br>GCGATATCGCCGTGGAGTGGGAGAGCAACGGCCAGCCCGAGAACAACTA<br>CAAGACCACCCCCCCAGTGCTGGACAGCGACGGCAGCTTCTTCCTGTACA |

TABLE 1-continued

Examples of anti-GITR agonist antibodies of the present invention.

| SEQ ID NO: Amino acid or polynucleotide (PN) description | Sequence |
|---|---|
| | GCAAGCTGACCGTGGACAAGTCCAGGTGGCAGCAGGGCAACGTGTTCAG<br>CTGCAGCGTGATGCACGAGGCCCTGCACAACCACTACACCCAGAAGTCC<br>CTGAGCCTGAGCCCCGGCAAG |
| 104: PN of LC, MAB8 encoding SEQ ID NO: 66 | GAGATCGTGATGACCCAGTCCCCCGCCACCCTGTCTGTGTCTCCCGGCGA<br>GAGAGCCACCCTGAGCTGCAGAGCCTCCGAGTCCGTGTCCTCCAACGTG<br>GCCTGGTATCAGCAGAGACCTGGTCAGGCCCCTCGGCTGCTGATCTACGG<br>CGCCTCTAACCGGGCCACCGGCATCCCTGCCAGATTCTCCGGCTCCGGCA<br>GCGGCACCGACTTCACCCTGACCATCTCCCGGCTGGAACCCGAGGACTTC<br>GCCGTGTACTACTGCGGCCAGTCCTACTCATACCCCTTCACCTTCGGCCA<br>GGGCACCAAGCTGGAAATCAAGCGTACGGTGGCCGCTCCCAGCGTGTTC<br>ATCTTCCCCCCCAGCGACGAGCAGCTGAAGAGCGGCACCGCCAGCGTGG<br>TGTGCCTGCTGAACAACTTCTACCCCCGGGAGGCCAAGGTGCAGTGGAA<br>GGTGGACAACGCCCTGCAGAGCGGCAACAGCCAGGAGAGCGTCACCGA<br>GCAGGACAGCAAGGACTCCACCTACAGCCTGAGCAGCACCCTGACCCTG<br>AGCAAGGCCGACTACGAGAAGCATAAGGTGTACGCCTGCGAGGTGACCC<br>ACCAGGGCCTGTCCAGCCCCGTGACCAAGAGCTTCAACAGGGGCGAGTG<br>C |

The CDRs of the antibodies listed in Table 1 can be determined by well known numbering systems known in the art, including those described herein. Table 2 listed the CDRs that are defined by (1) using the numbering system described in Kabat et al. (1991), "Sequences of Proteins of Immunological Interest," 5th Ed. Public Health Service, National Institutes of Health, Bethesda, Md. ("Kabat" numbering scheme), NIH publication No. 91-3242; and (2) Chothia, see Al-Lazikani et al., (1997) "Standard conformations for the canonical structures of immunoglobulins," J. Mol. Biol. 273:927-948.

TABLE 2

Kabat and Chothia CDR Comparison

| CDR | | SEQ ID NO: Kabat CDR (Kabat et al., 1991) | SEQ ID NO: Chothia CDR (Al-Laikani et al., 1997) |
|---|---|---|---|
| MAB1 | CDRH1 | 22: SYGVD | 79: GFSLRSY |
| MAB1 | CDRH2 | 62: VIWGGGTNYNSALMA | 80: WGGGG |
| MAB1 | CDRH3 | 29: HAYGHDGGFAMDY | 29: HAYGHDGGFAMDY |
| MAB1 | CDRL1 | 63: KASENVDTFVS | 81: SENVDTF |
| MAB1 | CDRL2 | 64: GASNRYT | 82: GAS |
| MAB1 | CDRL3 | 34: GQSYSYPFT | 83: SYSYPF |
| MAB2 | CDRH1 | 22: SYGVD | 84: GFSLSSY |
| MAB2 | CDRH2 | 23: VIWGGGTYYASSVMA | 80: WGGGG |
| MAB2 | CDRH3 | 29: HAYGHDGGFAMDY | 29: HAYGHDGGFAMDY |
| MAB2 | CDRL1 | 30: RASESVSSNVA | 85: SESVSSN |
| MAB2 | CDRL2 | 33: GASNRAT | 82: GAS |
| MAB2 | CDRL3 | 34: GQSYSYPFT | 83: SYSYPF |
| MAB3 | CDRH1 | 22: SYGVD | 84: GFSLSSY |
| MAB3 | CDRH2 | 24: VIWGGGTYYTASLMG | 80: WGGGG |
| MAB3 | CDRH3 | 29: HAYGHDGGFAMDY | 29: HAYGHDGGFAMDY |
| MAB3 | CDRL1 | 31: RASQSVSSNLA | 86: SQSVSSN |
| MAB3 | CDRL2 | 33: GASNRAT | 82: GAS |
| MAB3 | CDRL3 | 34: GQSYSYPFT | 83: SYSYPF |
| MAB4 | CDRH1 | 22: SYGVD | 84: GFSLSSY |
| MAB4 | CDRH2 | 25: VIWGGGTYYASSLMG | 80: WGGGG |
| MAB4 | CDRH3 | 29: HAYGHDGGFAMDY | 29: HAYGHDGGFAMDY |
| MAB4 | CDRL1 | 30: RASESVSSNVA | 85: SESVSSN |
| MAB4 | CDRL2 | 33: GASNRAT | 82: GAS |
| MAB4 | CDRL3 | 34: GQSYSYPFT | 83: SYSYPF |
| MAB5 | CDRH1 | 22: SYGVD | 84: GFSLSSY |
| MAB5 | CDRH2 | 26: VIWGGGTYYTSSLMG | 80: WGGGG |
| MAB5 | CDRH3 | 29: HAYGHDGGFAMDY | 29: HAYGHDGGFAMDY |
| MAB5 | CDRL1 | 30: RASESVSSNVA | 85: SESVSSN |
| MAB5 | CDRL2 | 33: GASNRAT | 82: GAS |
| MAB5 | CDRL3 | 34: GQSYSYPFT | 83: SYSYPF |
| MAB6 | CDRH1 | 22: SYGVD | 84: GFSLSSY |
| MAB6 | CDRH2 | 27: VIWGGGTYYTSSLMA | 80: WGGGG |
| MAB6 | CDRH3 | 29: HAYGHDGGFAMDY | 29: HAYGHDGGFAMDY |
| MAB6 | CDRL1 | 30: RASESVSSNVA | 85: SESVSSN |

TABLE 2-continued

Kabat and Chothia CDR Comparison

| CDR | SEQ ID NO: Kabat CDR (Kabat et al., 1991) | SEQ ID NO: Chothia CDR (AI-Laikani et al., 1997) |
|---|---|---|
| MAB6 CDRL2 | 33: GASNRAT | 82: GAS |
| MAB6 CDRL3 | 34: GQSYSYPFT | 83: SYSYPF |
| MAB7 CDRH1 | 22: SYGVD | 84: GFSLSSY |
| MAB7 CDRH2 | 25: VIWGGGGTYYASSLMG | 80: WGGGG |
| MAB7 CDRH3 | 29: HAYGHDGGFAMDY | 29: HAYGHDGGFAMDY |
| MAB7 CDRL1 | 30: RASESVSSNVA | 85: SESVSSN |
| MAB7 CDRL2 | 33: GASNRAT | 82: GAS |
| MAB7 CDRL3 | 34: GQSYSYPFT | 83: SYSYPF |
| MAB8 CDRH1 | 22: SYGVD | 84: GFSLSSY |
| MAB8 CDRH2 | 25: VIWGGGGTYYASSLMG | 80: WGGGG |
| MAB8 CDRH3 | 109: NAYGHDGGFAMDY | 109: NAYGHDGGFAMDY |
| MAB8 CDRL1 | 30: RASESVSSNVA | 85: SESVSSN |
| MAB8 CDRL2 | 33: GASNRAT | 82: GAS |
| MAB8 CDRL3 | 34: GQSYSYPFT | 83: SYSYPF |

In some embodiments, the anti-GITR antibodies or antibody fragments of the invention that binds to GITR (e.g., SEQ ID NO:1, cellular processed SEQ ID NO:1), is selected from any one of: i) an antibody, antibody fragment, or antigen binding molecule wherein: the heavy chain CDR1 comprises SEQ ID NO:22, the heavy chain CDR2 comprises SEQ ID NO:23, the heavy chain CDR3 comprises SEQ ID NO:29, the light chain CDR1 comprises SEQ ID NO:30, the light chain CDR2 comprises SEQ ID NO:33, and the light chain CDR3 comprises SEQ ID NO:34; ii) an antibody, antibody fragment, or antigen binding molecule wherein: the heavy chain CDR1 comprises SEQ ID NO:22, the heavy chain CDR2 comprises SEQ ID NO:24, the heavy chain CDR3 comprises SEQ ID NO:29, the light chain CDR1 comprises SEQ ID NO:31, the light chain CDR2 comprises SEQ ID NO:33, and the light chain CDR3 comprises SEQ ID NO:34; iii) an antibody, antibody fragment, or antigen binding molecule wherein: the heavy chain CDR1 comprises SEQ ID NO:22, the heavy chain CDR2 comprises SEQ ID NO:25, the heavy chain CDR3 comprises SEQ ID NO:29, the light chain CDR1 comprises SEQ ID NO:30, the light chain CDR2 comprises SEQ ID NO:33, and the light chain CDR3 comprises SEQ ID NO:34; iv) an antibody, antibody fragment, or antigen binding molecule wherein: the heavy chain CDR1 comprises SEQ ID NO:22, the heavy chain CDR2 comprises SEQ ID NO:26, the heavy chain CDR3 comprises SEQ ID NO:29, the light chain CDR1 comprises SEQ ID NO:30, the light chain CDR2 comprises SEQ ID NO:33, and the light chain CDR3 comprises SEQ ID NO:34; v) an antibody, antibody fragment, or antigen binding molecule wherein: the heavy chain CDR1 comprises SEQ ID NO:22, the heavy chain CDR2 comprises SEQ ID NO:27, the heavy chain CDR3 comprises SEQ ID NO:29, the light chain CDR1 comprises SEQ ID NO:30, the light chain CDR2 comprises SEQ ID NO:33, and the light chain CDR3 comprises SEQ ID NO:34; and vi) an antibody, antibody fragment, or antigen binding molecule wherein: the heavy chain CDR1 comprises SEQ ID NO:22, the heavy chain CDR2 comprises SEQ ID NO:25, the heavy chain CDR3 comprises SEQ ID NO:25, the heavy chain CDR3 comprises SEQ ID NO:109, the light chain CDR1 comprises SEQ ID NO:30, the light chain CDR2 comprises SEQ ID NO:33, and the light chain CDR3 comprises SEQ ID NO:34. In some embodiments, the antibodies or antibody fragments are humanized. In particular embodiments the antibodies or antibody fragments comprise a human constant region. In some embodiments the antibodies or antibody fragments comprise an IgG Fc region. In certain embodiments the antibody or antigen binding fragment is glycosylated. In some embodiments the antibodies or antibody fragments are modified or expressed in a modified cell, wherein such modification results in increased FcR effector function of the antibody or antibody fragment. In certain embodiments the antibody or antigen fragment induces an elevated Teff: Treg ratio in vivo. In some embodiments the antibody or antibody fragment induces a potentiated immune response in vivo. In some embodiments when the antibody or antibody fragment is cross linked to a second antibody or antibody fragment it is an agonist of SEQ ID NO:1, SEQ ID NO:2 or SEQ ID NO3.

In some embodiments, the anti-GITR antibodies or antibody fragments of the invention comprise a heavy chain variable region having at least 95%, 96%, 97%, 98%, 99%, or 100% amino acid sequence identity to a heavy chain variable region of SEQ ID NO:16 and comprise a light chain variable region having at least 95%, 96%, 97%, 98%, 99%, or 100% amino acid sequence identity to a light chain variable region of SEQ ID NO:17.

In some embodiments, the anti-GITR antibodies or antibody fragments of the invention comprise a heavy chain variable region having at least 90%, 91%, 92%, 93%, 94%, 95%, 96%, 97%, 98%, 99%, or 100% amino acid sequence identity to a heavy chain variable region of SEQ ID NO:6 and comprise a light chain variable region having at least 90%, 91%, 92%, 93%, 94%, 95%, 96%, 97%, 98%, 99%, or 100% amino acid sequence identity to a light chain variable region of SEQ ID NO:7.

In some embodiments, the anti-GITR antibodies or antibody fragments of the invention comprise a heavy chain variable region having at least 90%, 91%, 92%, 93%, 94%, 95%, 96%, 97%, 98%, 99%, or 100% amino acid sequence identity to a heavy chain variable region of SEQ ID NO:8 and comprise a light chain variable region having at least 90%, 91%, 92%, 93%, 94%, 95%, 96%, 97%, 98%, 99%, or 100% amino acid sequence identity to a light chain variable region of SEQ ID NO:9.

In some embodiments, the anti-GITR antibodies or antibody fragments of the invention comprise a heavy chain variable region having at least 90%, 91%, 92%, 93%, 94%, 95%, 96%, 97%, 98%, 99% or 100% amino acid sequence identity to a heavy chain variable region of SEQ ID NO:10 and comprise a light chain variable region having at least 90%, 91%, 92%, 93%, 94%, 95%, 96%, 97%, 98%, 99% or 100% amino acid sequence identity to a light chain variable region of SEQ ID NO:7.

In some embodiments, the anti-GITR antibodies or antibody fragments of the invention comprise a heavy chain variable region having at least 90%, 91%, 92%, 93%, 94%, 95%, 96%, 97%, 98%, 99%, or 100% amino acid sequence identity to a heavy chain variable region of SEQ ID NO:12 and comprise a light chain variable region having at least 90%, 91%, 92%, 93%, 94%, 95%, 96%, 97%, 98%, 99%, or 100% amino acid sequence identity to a light chain variable region of SEQ ID NO:7.

In some embodiments, the anti-GITR antibodies or antibody fragments of the invention comprise a heavy chain polypeptide having at least 90%, 91%, 92%, 93%, 94%, 95%, 96%, 97%, 98%, 99%, or 100% amino acid sequence identity to a heavy chain variable region of SEQ ID NO:14 and comprise a light chain polypeptide having at least 90%, 91%, 92%, 93%, 94%, 95%, 96%, 97%, 98%, 99%, or 100% amino acid sequence identity to a light chain variable region of SEQ ID NO:7.

In some embodiments, the anti-GITR antibodies or antibody fragments of the invention comprise a heavy chain variable region having at least 90%, 91%, 92%, 93%, 94%, 95%, 96%, 97%, 98%, 99% or 100% amino acid sequence identity to a heavy chain variable region of SEQ ID NO:99 and comprise a light chain variable region having at least 90%, 91%, 92%, 93%, 94%, 95%, 96%, 97%, 98%, 99% or 100% amino acid sequence identity to a light chain variable region of SEQ ID NO:7.

In some embodiments, the anti-GITR antibodies or antibody fragments of the invention comprise a heavy chain variable region having at least 90%, 91%, 92%, 93%, 94%, 95%, 96%, 97%, 98%, 99% or 100% amino acid sequence identity to a heavy chain variable region of SEQ ID NO:105 and comprise a light chain variable region having at least 90%, 91%, 92%, 93%, 94%, 95%, 96%, 97%, 98%, 99% or 100% amino acid sequence identity to a light chain variable region of SEQ ID NO:7.

In some embodiments, the anti-GITR antibodies or antibody fragments of the invention comprise a heavy chain polypeptide having at least 90%, 91%, 92%, 93%, 94%, 95%, 96%, 97%, 98%, 99%, or 100% amino acid sequence identity to a heavy chain variable region of SEQ ID NO:61 and comprise a light chain polypeptide having at least 90%, 91%, 92%, 93%, 94%, 95%, 96%, 97%, 98%, 99%, or 100% amino acid sequence identity to a light chain variable region of SEQ ID NO:59.

Over their full length, the anti-GITR antibodies of the present invention generally will have an overall constant region (e.g., IgG1) amino acid sequence identity of at least about 85%, for example, at least about 85%, 89%, 90%, 91%, 92%, 93%, 94%, 95%, 96%, 97%, 98%, 99%, or 100% to human IgG1/kappa constant region amino acid sequences. For example, the heavy chain of the anti-GITR antibodies can have at least about 85%, 89%, 90%, 91%, 92%, 93%, 94%, 95%, 96%, 97%, 98%, 99%, or 100% amino acid sequence identity to the human IgG1 constant region ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPE<u>LL</u>GGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:20). In one embodiment, the bold Leucine/Leucine residues are substituted with Alanine/Alanine. In one embodiment, the last amino acid, lysine (K), is substituted with arginine (R). The light chain of the anti-GITR antibodies can have at least about 85%, 89%, 90%, 91%, 92%, 93%, 94%, 95%, 96%, 97%, 98%, 99%, or 100% amino acid sequence identity to the human kappa light chain constant region RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:21). In some embodiments, amino acids within the constant regions are added, deleted, or substituted.

In some embodiments, such antibody is a human or humanized antibody. The VH, VL, full length light chain, and full length heavy chain sequences (amino acid sequences and the nucleotide sequences encoding the amino acid sequences) can be "mixed and matched" to create other GITR-binding antibodies of the invention. Such "mixed and matched" GITR-binding antibodies can be tested using the binding assays known in the art (e.g., ELISAs, and other assays described in the Example section) to confirm activity. When chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or antibody fragment having: a heavy chain variable region comprising an amino acid sequence selected from the group consisting of SEQ ID NOS:6, 8, 10, 12, 14, 99 and 105; and a light chain variable region comprising an amino acid sequence selected from the group consisting of SEQ ID NOS:7 and 9; wherein the antibody specifically binds to GITR.

In some embodiments, the anti-GITR antibodies or antibody fragments of the invention comprise a heavy chain polypeptide having at least 90%, 91%, 92%, 93%, 94%, 95%, 96%, 97%, 98%, 99%, or 100% amino acid sequence identity to a heavy chain sequence selected from any of SEQ ID NO:65, SEQ ID NO:69, SEQ ID NO:73, SEQ ID NO:75, SEQ ID NO:77, SEQ ID NO:100 and SEQ ID NO:106; and comprise a light chain polypeptide having at least 90%, 91%, 92%, 93%, 94%, 95%, 96%, 97%, 98%, 99%, or 100% amino acid sequence identity to a light chain of SEQ ID NO:66 or SEQ ID NO:70. In certain embodiments, the anti-GITR antibodies or antibody fragments of the invention comprise a heavy chain polypeptide selected from any of SEQ ID NO:65, SEQ ID NO:69, SEQ ID NO:73, SEQ ID NO:75, SEQ ID NO:77, SEQ ID NO:100 and SEQ ID NO:106; and comprise a light chain polypeptide of SEQ ID NO:66 or SEQ ID NO:70.

For identified amino acid sequences less than 20 amino acids in length, one or two conservative amino acid residue substitutions can be tolerated while still retaining the desired specific binding and/or agonist activity.

Anti-GITR antibodies and antibody fragments of the present invention generally will bind GITR, including 1(SEQ ID NO:1), isoform 2(SEQ ID NO:2) and isoform 3(SEQ ID NO:3), with an equilibrium dissociation constant ($K_D$) of less than about $10^{-8}$ M or $10^{-9}$ M, for example, or less than about $10^{-10}$ M or $10^{-11}$ M, and in some embodiments, less than about $10^{-12}$ M or $10^{-13}$ M.

Antibodies That Bind to the Same Epitope

The present invention provides antibodies and antibody fragments that bind to an epitope comprising the cysteine-rich domain 1 ("CRD1", SEQ ID NO:4: CGPGRLLLGTGTDARCCRVHTTRCCRDYPGEECCSEWDC) and the cysteine-rich domain 2 ("CRD2", SEQ ID NO:5: MCVQPEFHCGDPCCTTCRHHPCPPGQGVQSQGKFSFGFQC) of human GITR, and wherein the antibody, antibody fragment, or the antigen binding molecule is an agonist of hGITR, and wherein the antibody, antibody fragment, or the antigen binding molecule optionally has an intact or increased FcR effector function. In some embodiments, an antibody, antibody fragment, or the antigen binding molecule binds to an epitope comprising SEQ ID NO:88) of human GITR. In some embodiments an epitope comprises residues within SEQ ID NO:88. In some embodiments an epitope comprises amino acid residues within residues 34-72 and 78 of human GITR, where such antibodies and antibody fragments are agonists of hGITR.

The present invention also provides antibodies and antibody fragments that bind to the same epitope as do the GITR-binding antibodies described in Table 1. Additional antibodies and antibody fragments can therefore be identified based on their ability to cross-compete (e.g., to competitively inhibit the binding of, in a statistically significant manner) with other antibodies of the invention in GITR binding assays. The ability of a test antibody to inhibit the binding of antibodies and antibody fragments of the present invention to a GITR protein (e.g., human GITR) demonstrates that the test antibody can compete with that antibody or antibody fragment for binding to hGITR; such an antibody may, according to non-limiting theory, bind to the same or a related (e.g., a structurally similar or spatially proximal) epitope on the GITR protein as the antibody or antibody fragment with which it competes. In a certain embodiment, the antibody that binds to the same epitope on hGITR as the antibodies or antibody fragments of the present invention is a human or humanized monoclonal antibody. Such human or humanized monoclonal antibodies can be prepared and isolated as described herein.

Engineered and Modified Antibodies

An antibody or antibody fragment of the invention further can be prepared using an antibody having one or more of the CDRs and/or VH and/or VL sequences shown herein (e.g., Table 1) as starting material to engineer a modified antibody or antibody fragment, which modified antibody may have altered properties from the starting antibody. An antibody or antibody fragment can be engineered by modifying one or more residues within one or both variable regions (i.e., VH and/or VL), for example within one or more CDR regions and/or within one or more framework regions. Additionally or alternatively, an antibody or antibody fragment can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of a specific antibody by constructing expression vectors that include CDR sequences from the specific antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the invention pertains to an isolated monoclonal antibody, or an antigen binding fragment thereof, comprising a heavy chain variable region comprising CDR1 sequence having an amino acid sequence selected from the group consisting of SEQ ID NOS:22, 79, and 84; CDR2 sequences having an amino acid sequence selected from the group consisting of SEQ ID NOS:23, 24, 25, 26, 27, 62, and 80; CDR3 sequences having an amino acid sequence selected from the group consisting of SEQ ID NOS:29, 34 and 109, respectively; and a light chain variable region having CDR1 sequences having an amino acid sequence selected from the group consisting of SEQ ID NOS:30, 31, 63, 81, 85, and 86; CDR2 sequences having an amino acid sequence selected from the group consisting of SEQ ID NOS:33, 64, and 82; and CDR3 sequences consisting of an amino acid sequence selected from the group consisting of SEQ ID NOS:34 and 83; respectively. Thus, such antibodies contain the VH and VL CDR sequences of monoclonal antibodies, yet may contain different framework sequences from these antibodies. In certain embodiments, the isolated antibodies or antibody fragments comprise sequences that have amino acid sequence identity of at least about 85%, 89%, 90%, 91%, 92%, 93%, 94%, 95%, 96%, 97%, 98%, 99%, or 100% to the corresponding sequences in this paragraph.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the VH and/or VL CDR1, CDR2, and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples and/or alternative or additional assays known in the art. Conservative modifications can be introduced. The mutations may be amino acid substitutions, additions or deletions. Moreover, typically no more than one, two, three, four or five residues within a CDR region are altered.

Engineered antibodies or antibody fragments of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

When present, the constant regions of the anti-GITR antibodies or antibody fragments can be any type or subtype, as appropriate, and can be selected to be from the species of the subject to be treated by the present methods (e.g., human, non-human primate or other mammal, for example, agricultural mammal (e.g., equine, ovine, bovine, porcine, camelid), domestic mammal (e.g., canine, feline) or rodent (e.g., rat, mouse, hamster, rabbit). In some embodiments the anti-GITR antibodies are engineered to generate humanized or Humaneered®antibodies. In some embodiments, the constant region isotype is IgG, for example, IgG1, IgG2, IgG3, IgG4. In certain embodiments the constant region isotype is $IgG_1$.

In addition or alternative to modifications made within the framework or CDR regions, antibodies or antibody fragments of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody or antibody fragment of the invention may be chemically modified (e.g., one or more chemical moieties can be attached to the antibody) or be modified to alter its glycosylation, again to alter one or more functional properties of the antibody or antibody fragment.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody or antibody fragment.

In another embodiment, the Fc hinge region of an antibody is mutated to alter the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor (FcR) or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

Antibodies containing such mutations mediate reduced or no antibody-dependent cellular cytotoxicity (ADCC) or complement-dependent cytotoxicity (CDC). In some embodiments, amino acid residues L234 and L235 of the IgG1 constant region are substituted to Ala234 and Ala235. In some embodiments, amino acid residue N267 of the IgG1 constant region is substituted to Ala267.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies.

Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta (1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Grafting Antigen-binding Domains into Alternative Frameworks or Scaffolds

A wide variety of antibody/ immunoglobulin frameworks or scaffolds can be employed so long as the resulting polypeptide includes at least one binding region which specifically binds to GITR. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non- immunoglobulin scaffolds onto which CDRs of the invention can be grafted. Known or future non-immunoglobulin frameworks and scaffolds may be employed, as long as they comprise a binding region specific for the target GITR protein (e.g., human and/or cynomolgus GITR). Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel a-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium Staphylococcus aureus. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris Bras sicae has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

Human or Humanized Antibodies

The present invention provides engineered human antibodies that specifically bind to GITR protein (e.g., human GITR). Compared to the chimeric, primatized, or humanized antibodies, the human GITR-binding antibodies of the invention have further reduced antigenicity when administered to human subjects.

The human GITR-binding antibodies can be generated using methods that are known in the art. For example, the Humaneered® technology platform (KaloBios, S out San Francisco, Calif.) was used to convert non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody.

The anti-GITR antibodies of the invention are based on engineered human antibodies with V-region sequences having substantial amino acid sequence identity to human germline V region sequences while retaining the specificity and affinity of a reference antibody. See, U.S. Patent Publication No. 2005/0255552 and U.S. Patent Publication No. 2006/0134098, both of which are hereby incorporated herein by reference. The process of improvement identifies minimal sequence information required to determine antigen-binding specificity from the variable region of a reference antibody, and transfers that information to a library of human partial V-region gene sequences to generate an epitope-focused library of human antibody V regions. A microbial-based secretion system can be used to express members of the library as antibody Fab fragments and the library is screened for antigen-binding Fabs, for example, using a colony-lift binding assay. See, e.g., U.S. Patent Publication No. 2007/0020685. Positive clones can be further characterized to identify those with the highest affinity. The resultant engineered human Fabs retain the binding specificity of the parent, reference anti-GITR antibody, typically have equivalent or higher affinity for antigen in comparison to the parent antibody, and have V-regions with a high degree of sequence identity compared with human germ-line antibody V-regions.

The minimum binding specificity determinant (BSD) required to generate the epitope-focused library is typically represented by a sequence within the heavy chain CDR3 ("CDRH3") and a sequence within the light chain of CDR3 ("CDRL3"). The BSD can comprise a portion or the entire length of a CDR3. The BSD can be comprised of contiguous or non-contiguous amino acid residues. In some cases, the epitope-focused library is constructed from human V-segment sequences linked to the unique CDR3-FR4 region from the reference antibody containing the BSD and human germ-line J segment sequences (see, U.S. Patent Publication No. 2005/0255552). Alternatively, the human V segment libraries can be generated by sequential cassette replacement in which only part of the reference antibody V segment is initially replaced by a library of human sequences. The identified human "cassettes" supporting binding in the context of residual reference antibody amino acid sequences are then recombined in a second library screen to generate completely human V segments (see, U.S. Patent Publication No. 2006/0134098).

In each case, paired heavy and light chain CDR3 segments, CDR3-FR4 segments, or J segments, containing specificity determinants from the reference antibody, are used to constrain the binding specificity so that antigen-binders obtained from the library retain the epitope-specificity of the reference antibody. Additional maturational changes can be introduced in the CDR3 regions of each chain during the library construction in order to identify antibodies with optimal binding kinetics. The resulting engineered human antibodies have V-segment sequences derived from the human germ-line libraries, retain the short BSD sequence from within the CDR3 regions and have human germ-line framework 4 (FR4) regions.

Camelid Antibodies

Antibody proteins obtained from members of the camel and dromedary (*Camelus bactrianus* and *Calelus dromaderius*) family including new world members such as llama species (e.g., *Lama paccos, Lama glama*, and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be expressed in prokaryotic cells such as E. coli and are expressed as fusion proteins with bacteriophage and are functional.

Accordingly, a feature of the present invention is a camelid antibody or nanobody having high affinity for GITR. In certain embodiments herein, the camelid antibody or nanobody is naturally produced in the camelid animal, i.e., is produced by the camelid following immunization with GITR or a peptide fragment thereof, using techniques described herein for other antibodies. Alternatively, the GITR-binding camelid nanobody is engineered, i.e., produced by selection for example from a library of phage displaying appropriately mutagenized camelid nanobody proteins using panning procedures with GITR as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214. In some embodiments, the present invention provides multivalent camelid antibody or nanobody, according the methods described below.

Multivalent Antibodies

In another aspect, provided are multivalent molecules (monospecific, bispecific, or multispecific) comprising a GITR-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a multivalent molecule that binds to at least two different binding sites (which may be the same or different target sites or molecules). In some embodiments the antibody of the invention is derivatized or functionally linked (e.g., by chemical coupling, genetic fusion, noncovalent association or otherwise) to more than one other functional molecule to generate multivalent molecules that bind to two or more different binding sites which are the same or different binding sites on the same target molecule. In certain embodiments, the multivalent binding sites are the same. In some embodiments the antibody of the invention is derivatized or linked to more than one other functional molecule to generate multi-specific molecules that bind two or more different binding sites on at least two target molecules; such multi-specific molecules are also intended to be encompassed by the term "bispecific molecule" or "multispecific" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a multivalent molecule results. The present invention includes bispecific molecules comprising at least one first binding specificity for GITR and a second binding specificity for a second target epitope. For example, the second target epitope is another epitope of GITR different from the first target epitope. Additionally, for the invention in which the molecule is multi-specific, in some embodiments the molecule further includes a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the invention are murine, chimeric and humanized monoclonal antibodies.

The bispecific and/or multivalent molecules of the present invention can be prepared by conjugating the constituent binding specificities, using methods known in the art. For example, each binding specificity of the bispecific and/or multivalent molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt.

No. 78,118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When binding specificities are antibodies, they can be conjugated by sulfhydryl bonding of the constant domain hinge regions of the two heavy chains. In a particular embodiment, the hinge region is modified to contain an odd number of sulfhydryl residues, for example one, prior to conjugation.

Alternatively, binding specificities can be encoded in the same vector and expressed and assembled in the same host cell. This method is particularly useful where the bispecific and/or multivalent molecule is a mAb x mAb, mAb x Fab, Fab x F(ab')2 or ligand x Fab fusion protein. A bispecific and/or multivalent molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of bispecific and/or multivalent molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Antibodies with Extended Half Life

The present invention provides for antibodies and antibody fragments that specifically bind to GITR protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanoboies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E.coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defence system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622.

The strategies for increasing half life is especially useful in nanobodies, fibronectin-based binders, and other antibodies or proteins for which increased in vivo half life is desired.

Antibody Conjugates

The present invention provides antibodies or fragments thereof that specifically bind to a GITR protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90, or at least 100 amino acids) to generate fusion proteins. In particular, the invention provides fusion proteins comprising an antigen-binding fragment of an antibody described herein (e.g., a Fab fragment, Fd fragment, Fv fragment, F(ab)2 fragment, a VH domain, a VH CDR, a VL domain, or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308- 313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a GITR protein may be recombined with one or more components, motifs, sections, parts, domains, fragments, etc. of one or more heterologous molecules.

Moreover, the antibodies or fragments thereof can be fused to marker sequences, such as a peptide to facilitate purification. In preferred embodiments, the marker amino acid sequence is a hexa-histidine (HHHHHH SEQ ID NO:11) peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO:11) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re,142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

The present invention further encompasses an antibody or fragment thereof conjugated to a therapeutic moiety or drug moiety that modifies a given biological effect or response and uses of antibodies or fragments thereof conjugated to a therapeutic moiety. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

For example, an antibody can be conjugated to therapeutic moieties such as a radioactive metal ion, such as alphemiters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules include for example, glycine linkers e.g., GGGGS (SEQ ID NO:15), which may optionally be repeated, e.g., GGGGSGGGGSGGGGS (SEQ ID NO:18), or other linkers are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Polynucleotides Encoding Agonist Anti-GITR Antibodies

Anti-GITR antibodies, antigen binding molecules, and fragments thereof, can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementary determining regions as described herein. In some embodiments, the polynucleotide encoding the heavy chain variable regions comprises a sequence having at least 85%, 89%, 90%, 91%, 92%, 93%, 94%, 95%, 96%, 97%, 98%, 99%, or 100% nucleic acid sequence identity with a polynucleotide selected from the group consisting of SEQ ID NO:51, SEQ ID NO:53, SEQ ID NO:55, SEQ ID NO:56, SEQ ID NO:57, SEQ ID NO:101, and SEQ ID NO:107. In some embodiments, the polynucleotide encoding the light chain variable regions comprises a sequence having at least 85%, 89%, 90%, 91%, 92%, 93%, 94%, 95%, 96%, 97%, 98%, 99%, or 100% nucleic acid sequence identity with a polynucleotide selected from the group consisting of SEQ ID NO:52, SEQ ID NO:54, and SEQ ID NO:102.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:67. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:68.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:72. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide selected of SEQ ID NO:73.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:74. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:68.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:76. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:68.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:78. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:68.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NO:103. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:104.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:108. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:104.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO:60. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO:58.

The polynucleotides of the invention can encode only the variable region sequence of an anti-GITR antibody. They can also encode both a variable region and a constant region of the antibody. Some of the polynucleotide sequences encode a polypeptide that comprises variable regions of both the heavy chain and the light chain of one of the exemplified mouse anti-GITR antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described herein) encoding an anti-GITR antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the anti-GITR antibodies described above. Various expression vectors can be employed to express polynucleotides encoding the anti-GITR antibody chains, fragments, or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-GITR polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-GITR antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-GITR antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

Expression vectors may also provide a secretion signal sequence position to form a fusion protein with polypeptides encoded by inserted anti-GITR antibody sequences. More often, the inserted anti-GITR antibody sequences are linked to a signal sequences before inclusion in the vector. Vectors to be used to receive sequences encoding anti-GITR antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

Host cells for harboring and expressing the anti-GITR antibody chains can be either prokaryotic or eukaryotic. *E. coli* is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-GITR polypeptides of the invention. Insect cells in combination with baculovirus vectors can also be used.

In some preferred embodiments, mammalian host cells are used to express and produce the anti-GITR polypeptides of the present invention. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-GITR antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Assays for Identifying Agonist Anti-GITR Antibodies

Assays for identifying agonist anti-GITR antibodies are known in the art and described herein. Agonist anti-GITR antibodies bind to GITR and promote, induce, stimulate intracellular signaling through GITR.

Binding of the anti-GITR antibodies to GITR can be determined using any method known in the art. For example, binding to GITR can be determined using known techniques, including without limitation ELISA, Western blots, surface plasmon resonance (e.g., BIAcore), and flow cytometry.

Intracellular signaling through GITR can be measured using any method known in the art. For example, activation through GITR promotes NFκB and MAPK signaling. Methods for measuring NFκB and MAPK activation are standard in the art (e.g., use of reporter gene assays, nuclear translocation of NFκB proteins, phosphorylation status of MAPK proteins). Activation through GITR is a co-stimulatory signal that promotes proliferation of activated $CD4^+$ and $CD8^+$ T cells in the presence of activation through the T-cell receptor (e.g., in the presence of primary or target antigen). Methods for measuring proliferation of cells are standard in the art (e.g., $^3$H-thymidine incorporation assays, CFSE labeling). Signaling through GITR also co-stimulates activated $CD4^+$ and $CD8^+$ T cells in the presence of activation through the T-cell receptor to produce cytokines. Signaling through GITR also co-stimulates activated NK cells to produce cytokines. The cytokines can be either or both Th1-type cytokines (e.g., interferon-γ, IL-2 and TNF) and Th2-type cytokines (e.g., IL-4, IL-5, IL-10 and IL-13). Methods for measuring cytokine production are well known in the art (e.g., ELISA assays, ELISpot assays). Activation through GITR may also induce apoptosis. Methods for measuring apoptosis of cells are standard in the art (e.g., Annexin V staining). In performing in vitro assays, test cells or culture supernatant from test cells contacted with the agonist anti-GITR antibodies can be compared to control cells or culture supernatants from control cells that have not been contacted with the agonist anti-GITR antibodies.

The GITR agonist functionalities of the present antibodies can also be measured in vivo. Preferred agonist anti-GITR antibodies have the ability to activate and expand $CD4^+$ and $CD8^+$ T-cells. The in vivo activation and expansion of $CD4^+$ and $CD8^+$ T-cells can be measured using any method known in the art, e.g., by flow cytometry. Preferred agonist anti-GITR antibodies can be therapeutically useful in inhibiting tumor growth or promoting tumor retraction. Tumor growth, or inhibition thereof, can be measured using any method known in the art (e.g., visual inspection, calipers, weight, imaging techniques, including MRI). Preferred agonist anti-GITR antibodies can be therapeutically useful in preventing, reducing, inhibiting or eliminating the causative factor of an infectious disease, e.g., a bacterial, fungal, viral or parasitic infection. The efficacy of the agonist anti-GITR antibodies in augmenting a T-cell response or reducing the severity of a disease can be determined by administering a therapeutically effective amount of the antibody to a subject and comparing the subject before and after administration of the antibody. Efficacy of the agonist anti-GITR antibodies in augmenting a T-cell response or reducing the severity of a disease also can be determined by administering a therapeutically effective amount of the antibody to a test subject and comparing the test subject to a control subject who has not been administered the antibody.

Compositions Comprising Agonist Anti-GITR Antibodies

The invention provides pharmaceutical compositions comprising the present anti-GITR antibodies or antigen-binding molecules formulated together with a pharmaceutically acceptable carrier. Optionally, pharmaceutical compositions additionally contain one or more other therapeutic agent(s) that are suitable for treating or preventing a given disorder. Pharmaceutically acceptable carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. Route and/or mode of administration vary depending upon the desired results. It is preferred that administration be intravenous, intramuscular, intraperitoneal, or subcutaneous, or administered proximal to the site of the target. A pharmaceutically acceptable carrier should be suitable for intravenous, intramuscular, subcutaneous, parenteral, intranasal, inhalational, spinal or epidermal administration (e.g., by injection or infusion). Depending on the route of administration, active compound, e.g., antibody or antigen binding fragment or multivalent molecule of the invention (e.g., monospecific, bispecific or multispecific molecule), may be coated in a material to protect the compound from the action of acids and other natural conditions that may inactivate the compound.

An antibody or fragment thereof, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin. In certain embodiments compositions can be prepared for storage in a lyophilized form using appropriate excipients (e.g., sucrose)

Pharmaceutical compositions of the invention can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions of the present invention. Applicable methods for formulating the antibodies and determining appropriate dosing and scheduling can be found, for example, in *Remington: The Science and Practice of Pharmacy*, 21$^{st}$ Ed., University of the Sciences in Philadelphia, Eds., Lippincott Williams & Wilkins (2005); and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, and Sustained and Controlled Release Drug Delivery Systems, J. R. Robinson, ed., Marcel Dekker, Inc., New York, 1978, each of which are hereby incorporated herein by reference. Pharmaceutical compositions are preferably manufactured under GMP conditions. Typically, a therapeutically effective dose or efficacious dose of the anti-GITR antibody is employed in the pharmaceutical compositions of the invention. The anti-GITR antibodies are formulated into pharmaceutically acceptable dosage forms by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

Co-Formulation with Second Agent

In some embodiments, the pharmacological compositions comprise a mixture of the anti-GITR antibody or antigen binding molecule and a second pharmacological agent. Exemplary second agents for inclusion in mixtures with the present anti-GITR agonist antibody or antigen binding molecule include without limitation primary or target antigens, agents that increase the immunogenicity of a tumor cell, agents that inhibit or suppress co-inhibitory signals.

The anti-GITR antibodies or antigen binding molecules of the invention can be co-formulated (i.e., provided as a mixture or prepared in a mixture) with a primary or target antigen. The target antigen, or vaccine, will depend on the disease condition to be treated. For example, the target antigen may be from a tumor cell, a bacterial cell, a fungus, a virus or a parasite. The target antigen can be in the form of a peptide, a polypeptide, a cell or a polynucleotide, as appropriate.

In one embodiment, the target antigen is from a virus, e.g., selected from the group consisting of: hepatitis type A, hepatitis type B, hepatitis type C, influenza, varicella, adenovirus, herpes simplex type I (HSV I), herpes simplex type II (HSV II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, human immunodeficiency virus type I (HIV I), and human immunodeficiency virus type II (HIV II), any picornaviridae, enteroviruses, caliciviridae, any of the Norwalk group of viruses, togaviruses, such as alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein Barr virus, human herpesvirus 6, cercopithecine herpes virus 1 (B virus), and poxviruses.

In one embodiment, the target antigen is from a bacterium, e.g., selected from the group consisting of: *Neisseria* spp, *Streptococcus* spp, *S. mutans*, *Haemophilus* spp., *Moraxella* spp, *Bordetella* spp, *Mycobacterium* spp, *Legionella* spp, *Escherichia* spp, *Vibrio* spp, *Yersinia* spp, *Campylobacter* spp, *Salmonella* spp, *Listeria* spp., *Helicobacter* spp, *Pseudomonas* spp, *Staphylococcus* spp., *Enterococcus* spp, *Clostridium* spp., *Bacillus* spp, *Corynebacterium* spp., *Borrelia* spp., *Ehrlichia* spp, *Rickettsia* spp, *Chlamydia* spp., *Leptospira* spp., *Treponema* spp.

In some embodiments, the anti-GITR antibodies or antigen binding molecules are co-formulated in a mixture with a tumor-associated antigen (TAA). The TAA can be an isolated polypeptide or peptide, can be part of an intact cell or part of a tumor cell lysate. The TAAs can be a polynucleotide, for example a naked plasmid or a viral vector comprising a polynucleotide encoding one or more TAAs. Examples of known TAAs include without limitation, melanoma associated antigens (MAGE-1, MAGE-3, TRP-2, melanosomal membrane glycoprotein gp100, gp75 and MUC-1 (mucin-1) associated with melanoma); CEA (carcinoembryonic antigen) which can be associated, e.g., with ovarian, melanoma or colon cancers; folate receptor alpha expressed by ovarian carcinoma; free human chorionic gonadotropin beta (hCGβ) subunit expressed by many different tumors, including but not limited to myeloma; HER-2/neu associated with breast cancer; encephalomyelitis antigen HuD associated with small-cell lung cancer; tyrosine hydroxylase associated with neuroblastoma; prostate-specific antigen (PSA) associated with prostate cancer; CA125 associated with ovarian cancer; and the idiotypic determinants of a B cell lymphoma can generate tumor-specific immunity (attributed to idiotype-specific humoral immune response). Moreover, antigens of human T cell leukemia virus type 1 have been shown to induce specific CTL responses and antitumor immunity against the virus-induced human adult T cell leukemia (ATL). See, e.g., Haupt, et al., *Experimental Biology and Medicine* (2002) 227:227-237; Ohashi, et al., *Journal of Virology* (2000) 74(20):9610-9616. Other TAAs are known and find use for co-formulation with the anti-GITR antibodies.

In some embodiments, the anti-GITR antibodies or antigen binding molecules are co-formulated with autologous tumor cells from the patient, or allogeneic tumor cells of the same tissue type from another patient. The tumor cells can be in the form of intact cells, tumor cell lysate, apoptotic tumor cells or total tumor mRNA. The tumor cells can be transfected to express a polypeptide that enhances or augments the immunogenity of the tumor cell in the patient, e.g., transfected to express granulocyte colony stimulating factor (GM-CSF). The tumor cells can be from any cancerous tissue, including without limitation, epithelial cancers or carcinomas, as well as sarcomas and lymphomas. In some embodiments, the cancer is melanoma, ovarian cancer, renal cancer, colorectal cancer, prostate, lung cancer including non-small cell lung cancer (NSCLC), breast cancer, glioma, fibrosarcoma, hematologic cancer ,or a head and neck squamous cell carcinoma (HNSCC). See, e.g., Pardee, et al, *Immunotherapy* (2009) 1(2):249-264, and references discussed therein. In some embodiments, the tumor cell is from, e.g., pancreatic cancer, melanomas, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

In some embodiments, the anti-GITR antibodies or antigen binding molecules are co-formulated with a cytotoxic agent. For example, the anti-GITR antibodies or antigen binding molecules are co-formulated with an agonist antibody or antigen binding molecule that binds to and reduces or depletes CD4+ CD25+ regulatory T cells (Treg). Exemplary Treg cell-depleting antibodies or antigen binding molecules bind to CD25 or CCR4. See, *Expert Opin Ther Patents* (2007) 17(5):567-575, and the references discussed therein.

In some embodiments, the anti-GITR antibodies or antigen binding molecules are co-formulated with an inhibitor of a co-inhibitory signal. Exemplary inhibitors include inhibitors of CTLA-4 and inhibitors of the PD-1/PD-L1 (e.g., B7-H1) interaction. In some embodiments, the anti-GITR antibodies are co-formulated with an antibody that binds to and inhibits CTLA-4. In some embodiments, the anti-GITR antibodies are co-formulated with an antibody that binds to and inhibits TIM3. In some embodiments, the anti-GITR antibodies are co-formulated with an antibody that binds to and inhibits LAG3. In some embodiments, the anti-GITR antibodies are co-formulated with an antibody that binds to and inhibits PD-1. In some embodiments, the anti-GITR antibodies are co-formulated with an antibody that binds to and inhibits B7-H1. See, e.g., *Expert Opin Ther Patents* (2007) 17(5):567-575; and Melero, et al., *Clin Cancer Res* (2009) 15(5):1507-1509, and the references discussed therein. In certain embodiments, formulations comprising a bispecific molecule including an anti-GITR antibody or antigen binding molecule and inhibitor of a co-inhibitory signal. In some embodiments, formulations comprise a bispecific molecule including an anti-GITR antibody or antigen binding molecule and an inhibitor of CTLA4. In some embodiments, formulations comprise a bispecific molecule including an anti-GITR antibody or antigen binding molecule and an inhibitor of TIM3. In some embodiments, formulations comprise a bispecific molecule including an anti-GITR antibody or antigen binding molecule and an inhibitor of LAG3. In some embodiments, formulations comprise a bispecific molecule including an anti-GITR antibody or antigen binding molecule and an inhibitor of PD-1/PD-L1. In some embodiments, formulations comprise a bispecific molecule including an anti-GITR antibody or antigen binding molecule and an inhibitor B7H1.

PD-1 Inhibitors

In one embodiment, the GITR agonist is used in combination with a PD-1 inhibitor, e.g., as described in WO2015/026684. In some embodiments, the PD-1 inhibitor is an anti-PD-1 antibody chosen from Nivolumab, Pembrolizumab or Pidilizumab.

In some embodiments, the anti-PD-1 antibody is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168. In one embodiment, the inhibitor of PD-1 is Nivolumab, and having a sequence disclosed therein (or a sequence substantially identical or similar thereto, e.g., a sequence at least 85%, 90%, 95% identical or higher to the sequence specified).

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335.

In one embodiment, the inhibitor of PD-1 is Pembrolizumab disclosed in, e.g., U.S. Pat. No. 8,354,509 and WO 2009/114335, and having a sequence disclosed therein (or a sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611. Other anti-PD1 antibodies include AMP 514 (Amplimmune), among others, e.g., anti-PD1 antibodies disclosed in U.S. Pat. No. 8,609,089, US 2010028330, and/or US 20120114649.

In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 inhibitor is AMP-224 (B7-DCIg; AmpImmune; e.g., disclosed in WO2010/027827 and WO2011/066342), is a PD-L2 Fc fusion soluble receptor that blocks the interaction between PD-1 and B7-H1.

In one embodiment, a combination includes an anti-GITR antibody molecule, e.g., as described herein, and an anti-PD-1 antibody disclosed in, e.g., WO 2015/112900, and having a sequence disclosed therein (or a sequence substantially identical or similar thereto, e.g., a sequence at least 85%, 90%, 95% identical or higher to the sequence specified).

PD-L1 or PD-L2 Inhibitors

In some embodiments, the PD-L1 inhibitor is an antibody molecule. In some embodiments, the anti-PD-L1 inhibitor is chosen from YW243.55.570, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. Pembrolizumab and other humanized anti-PD-L1 antibodies are disclosed in WO2013/079174, and having a sequence disclosed therein (or a sequence substantially identical or similar thereto, e.g., a sequence at least 85%, 90%, 95% identical or higher to the sequence specified).

In one embodiment, the PD-L1 inhibitor is YW243.55.570. The YW243.55.570 antibody is an anti-PD-L1 described in WO 2010/077634 (heavy and light chain variable region sequences shown in SEQ ID Nos. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In other embodiments, the PD-L2 inhibitor is AMP-224. AMP-224 is a PD-L2 Fc fusion soluble receptor that blocks the interaction between PD1 and B7-H1 (B7-DCIg; AmpImmune; e.g., disclosed in WO2010/027827 and WO2011/066342).

LAG-3 Inhibitors

In one embodiment, a combination described herein includes a LAG-3 inhibitor. In some embodiments, the combination is used to treat a cancer, e.g., a cancer described herein, e.g., a solid tumor or a hematologic malignancy. In some embodiments, the anti-LAG-3 antibody is BMS-986016. BMS-986016 (also referred to as BMS986016; Bristol-Myers Squibb) is a monoclonal antibody that binds to LAG-3. BMS-986016 and other humanized anti-LAG-3 antibodies are disclosed in US 2011/0150892, WO2010/019570, and WO2014/008218. In some embodiments, the anti-LAG-3 antibody is a humanized anti-LAG3 antibody disclosed in WO2015/138920.

TIM-3 Inhibitors

In one embodiment, a combination described herein includes a TIM-3 inhibitor. In some embodiments, the combination is used to treat a cancer, e.g., a cancer described herein, e.g., a solid tumor or a hematologic malignancy. Exemplary anti-TIM-3 antibodies are disclosed in U.S. Pat. No.: 8,552,156, WO 2011/155607, EP 2581113 and U.S Publication No.: 2014/044728. In some embodiments the anti-TIM3 is a humanized ABTIM3 mAb disclosed in WO2015/117002.

CTLA-4 Inhibitors

In one embodiment, a combination described herein includes a CTLA-4 inhibitor. In some embodiments, the combination is used to treat a cancer, e.g., a cancer described herein, e.g., a solid tumor or a hematologic malignancy.

Exemplary anti-CTLA4 antibodies include Tremelimumab (IgG2 monoclonal antibody available from Pfizer, formerly known as ticilimumab, CP-675,206); and Ipilimumab (CTLA-4 antibody, also known as MDX-010, CAS No. 477202-00-9). Other exemplary anti-CTLA-4 antibodies are disclosed, e.g., in U.S. Pat. No. 5,811,097.

The anti-GITR antibodies or antigen binding molecules can also be co-formulated with one or more immunostimulatory agents. For example, in some embodiments, the anti-GITR antibodies are co-formulated with an immunostimulatory cytokine, for example, IL-7, IL-12 or IL-15. Alternatively, the anti-GITR antibodies or antigen binding molecules can be co-formulated with a second immunostimulatory antibody. For example, the anti-GITR antibodies or antigen binding molecules can also be co-formulated with an agonist antibody or antigen binding molecule of another member of the tumor necrosis factor receptor superfamily. Exemplary secondary immunostimulatory targets include without limitation TNFRSF4 tumor necrosis factor receptor superfamily, member 4 (also known as OX40) or tumor necrosis factor receptor superfamily, member 9 (also known as TNFRSF9, 4-1BB or CD137). See, e.g., *Expert Opin Ther Patents* (2007) 17(5):567-575; Pardee, et al, *Immunotherapy* (2009) 1(2):249-264; and Melero, et al., *Clin Cancer Res* (2009) 15(5):1507-1509, and the references discussed therein.

The anti-GITR antibodies or antigen binding molecules can also be co-formulated with a chemotherapeutic agent. The selected agent will depend on the condition to be treated, e.g., a cancer or an infectious disease, such as a bacterial infection, a fungal infection, a viral infection or a parasitic infection. The anti-GITR antibodies or antigen binding molecules can be co-formulated with a chemotherapeutic known by those of skill to treat the disease condition being treated. Chemotherapeutic agents, e.g., for the treatment of cancers and infectious diseases are known in the art, and are described, e.g., in *Goodman and Gilman's The Pharmacological Basis of Therapeutics,* 11th Ed., Brunton, Lazo and Parker, Eds., McGraw-Hill (2006); 2010 *Physicians' Desk Reference* (PDR), 64th Edition, Thomson PDR.

In some embodiments, the anti-GITR antibodies or antigen binding molecules can be co-formulated with an antineoplastic agent. Exemplary antineoplastic agents that find use for mixing in compositions with the anti-GITR antibodies include alkylating agents (e.g., nitrogen mustards, ethyleneimines and methylmelamines, methylhydrazine derivative, alkyl sulfonate, nitrosoureas, triazenes and platinum coordination complexes); antimetabolites (e.g., folic acid analogs, pyrimidine analogs, purine analogs; natural products (e.g., vinca alkaloids, taxanes, epipodophyllotoxins, camptothecins, antibiotics, and anthracenedione). In some embodiments, the anti-GITR antibodies or antigen binding molecules are co-formulated with an antimetabolite antineoplastic agent, e.g., a folic acid analog (e.g., methotrexate, pemetrexed, trimetrexate), a pyrimidine analog (e.g., 5-fluorouracil, capecitabine, cytarabine, gemcitabine), a purine analog (e.g., mercaptopurine, pentostatin, cladribine fludarabine), or mixtures thereof. In some embodiments, the anti-GITR antibodies or antigen binding molecules are co-formulated with an alkylating agent antineoplastic agent, e.g., nitrogen mustards (e.g., mechlorethamine, cyclophosphamide, ifosfamide, melphalan, chlorambucil), ethyleneimines (e.g., altretamine) and methylmelamines (e.g., thiotepa), methylhydrazine derivatives (e.g., procarbazine), alkyl sulfonate (e.g., busulfan), nitrosoureas (e.g., carmustine, streptozocin), triazenes (e.g., dacarbazine, temozolomide) and platinum coordination complexes (e.g., cisplatin, carboplatin, oxaliplatin).

In some embodiments, the anti-GITR antibodies or antigen binding molecules can be co-formulated with an antiviral agent. Exemplary antiviral agents include without limitation anti-herpesvirus agents (e.g., acyclovir, cidofovir, famciclovir, foscarnet, thiovir, fomivirsen, ganciclovir, idoxuridine, penciclovir, trifluridine, valacyclovir, valgenciclovir, resiquimod); anti-influenza agents (e.g., amantadine, oseltamivir, rimantadine, zanamivir, peramivir, E-118958); anti-hepatitis agents (e.g., adefovir dipivoxil, interferon-alpha, lamivudine, entecavir, clevudine, emtricitabine, telbivudine, tenofovir, viramidine, BILN 2061, NM283) and other antiviral agents (e.g., ribavirin, imiquimod, maribavir, sICAM-1, pleconaril). The antiviral agent can be an antiretroviral agent. Exemplary antiretroviral agents include without limitation zidovudine, didanosine, stavudine, zalcitabine, lamivudine, abacavir, tenofovir, emtricitabine, nevirapine, efavirenz, delavirdine, saquinavir, indinavir, ritonavir, nelfinavir, amprenavir, lopinavir, atazanavir, fosamprenavir and enfuvirtide.

In some embodiments, the anti-GITR antibodies or antigen binding molecules can be co-formulated with an antibacterial agent. Exemplary antibacterial agents include without limitation sulfonamides (e.g., sulfanilamide, sulfadiazine, sulfamethoxazole, sulfisoxazole, sulfacetamide), trimethoprim, quinolones (e.g., nalidixic acid, cinoxacin, norfloxacin, ciprofloxacin, ofloxacin, sparfloxacin, fleroxacin, perloxacin, levofloxacin, garenoxacin and gemifloxacin), methenamine, nitrofurantoin, penicillins (e.g., penicillin G, penicillin V, methicilin oxacillin, cloxacillin, dicloxacillin, nafcilin, ampicillin, amoxicillin, carbenicillin, ticarcillin, mezlocillin, and piperacillin), cephalosporins (e.g., cefazolin, cephalexin, cefadroxil, cefoxitin, cefaclor, cefprozil, cefuroxime, cefuroxime acetil, loracarbef, cefotetan, ceforanide, cefotaxime, cefpodoxime proxetil, cefibuten, cefdinir, cefditoren pivorxil, ceftizoxime, ceftriaxone, cefoperazone, ceftazidime, and cefepine), carbapenems (e.g., imipenem, aztreonam), and aminoglycosides (e.g., neomycin, kanamycin, streptomycin, gentamicin, toramycin, netilmicin, and amikacin).

In some embodiments, the anti-GITR antibodies or antigen binding molecules can be co-formulated with an anti-parasitic agent. Exemplary anti-parasitic agents include without limitation anti-malarial agents (e.g., quinolines including chloroquine, mefloquine, quinine, quinidine, and primaquine; diaminopyrimidines including pyrimethamine, sulfadoxine, tetracyclines, atovaquone, and proguanil); anti-protozoal agents including amphotericin, chloroquine, eflornithine, emetine, fumagillin, 8-hydroxyquinolines, melarsoprol, metronidazole, miltefosine, nifurtimox, nitazoxanide, paromomycin, pentamidine, sodium stibogluconate, and suramin.

In some embodiments, the anti-GITR antibodies or antigen binding molecules can be co-formulated with an anti-fungal agent. Exemplary anti-fungal agents include without limitation polyenes (e.g., natamycin, rimocidin, filipin, nystatin, amphotericin B, candicin, and hamycin), imidazoles (e.g., miconazole, ketoconazole, clotrimazole, econazole, bifonazole, butoconazole, fenticonazole, isoconazole, oxiconazole, sertaconazole, sulconazole, tioconazole), triazoles (e.g., fluconazole, itraconazole, isavuconazole, ravuconazole, posaconazole, voriconazole, terconazole), thiazoles (e.g., abafungin), allylamines (e.g., terbinafine, amorolfine, naftifine, butenafine), echinocandins (e.g., anidulafungin, caspofungin, micafungin), benzoic acid, ciclopirox, tolnaftate, undecylenic acid, flucytosine or 5-fluorocytosine, griseofulvin, and haloprogin.

Kits

The anti-GITR compositions of the present invention can be provided in a kit. The anti-GITR antibody, antibody fragment, or antigen binding molecule is generally in a vial or a container. As appropriate, the antibody can be in liquid or dried (e.g., lyophilized) form. The kits can comprise an anti-GITR antibody, antibody fragment, or antigen binding molecule of the invention, as described herein, and optionally also contain a second or third agent. In some embodiments, the kits contain anti-GITR antibody, antibody fragment, or antigen binding molecule of the invention and a pharmaceutically acceptable diluent. The anti-GITR antibodies, antibody fragments, or antigen binding molecules can be provided in the kit with the second or third agents in the same or separate formulations (e.g., as mixtures or in separate containers). The kits can contain aliquots of the anti-GITR antibodies, antibody fragments, or antigen binding molecules that provide for one or more doses. If aliquots for multiple administrations are provided, the doses can be uniform or varied. Varied dosing regimens can be escalating or decreasing, as appropriate. The dosages of the anti-GITR antibody, antibody fragment, or antigen binding molecule and the second agent can be independently uniform or varying.

In some embodiments, the kits further contain a target antigen. The target antigen, or vaccine, will depend on the disease condition to be treated. For example, the target antigen may be from a tumor cell, a bacterial cell, a fungus, a parasite or a virus. The target antigen can be in the form of a peptide, a polypeptide, a cell, a polynucleotide (e.g., naked plasmid or viral vector) as appropriate. In some embodiments, the target antigen is a tumor associated antigen. Exemplary target antigens are discussed herein; others known in the art also find use.

In some embodiments, the kits further contain a cytotoxic agent. For example, the kits can contain an agonist antibody or antigen binding molecule that binds to and reduces or depletes CD4+ CD25+ regulatory T cells (Treg). Exemplary Treg cell-depleting antibodies or antigen binding molecules bind to CD25 or CCR4. See, *Expert Opin Ther Patents* (2007) 17(5):567-575, and the references discussed therein.

In some embodiments, the kits further contain an inhibitor of a co-inhibitory signal. Exemplary inhibitors include inhibitors of CTLA-4, LAG3, TIM3, and/or inhibitors of the PD-1/PD-L1 (e.g., B7-H1) interaction. In some embodiments, the kits further contain an antibody that binds to and inhibits CTLA-4. In some embodiments, the kits further contain an antibody that binds to and inhibits LAG3. In some embodiments, the kits further contain an antibody that binds to and inhibits TIM3. In some embodiments, the kits further contain an antibody that binds to and inhibits PD-1. In some embodiments, the kits further contain an antibody that binds to and inhibits B7-H1. See, e.g., *Expert Opin Ther Patents* (2007) 17(5):567-575; and Melero, et al., *Clin Cancer Res* (2009) 15(5):1507-1509, and the references discussed therein.

In some embodiments, the kits further contain one or more immunostimulatory agents. For example, in some embodiments, the kits contain an immunostimulatory cytokine, for example, IL-7, IL-12 or IL-15. Alternatively, the kits can contain a second immunostimulatory antibody. For example, the kits can contain an agonist antibody or antigen binding molecule of another member of the tumor necrosis factor receptor superfamily. Exemplary secondary immunostimulatory targets include without limitation TNFRSF4 tumor necrosis factor receptor superfamily, member 4 (also known as OX40) or tumor necrosis factor receptor superfamily, member 9 (also known as TNFRSF9, 4-1BB or CD137). See, e.g., *Expert Opin Ther Patents* (2007) 17(5):567-575; Pardee, et al, *Immunotherapy* (2009) 1(2):249-264; and Melero, et al., *Clin Cancer Res* (2009) 15(5):1507-1509, and the references discussed therein.

In some embodiments, the kits further contain a chemotherapeutic agent. The selected agent will depend on the condition to be treated, e.g., a cancer or an infectious disease, such as a bacterial infection, a fungal infection, a viral infection or a parasitic infection. Exemplary chemotherapy agents include any antineoplastic, antiviral, antibacterial, antiparasitic, and antifungal agents known in the art and described herein.

Methods of Enhancing T Cell Responses
Conditions Subject to Treatment or Prevention The anti-GITR agonist antibodies and antibody fragments of the invention find use in augmenting $CD4^+$ T helper and $CD8^+$ cytolytic T cell responses in a patient in need thereof. Therefore, the antibodies find use in enhancing or augmenting a T cell response in a patient, e.g., to effect the reduction, reversal, inhibition or prevention of a disease that can be counteracted with an enhanced or augmented immune response. In one aspect, the invention provides methods of enhancing a T cell response in an individual in need thereof, comprising administering to the individual a therapeutically effective amount of an anti-GITR agonist antibody or antibody fragment of the invention, as described herein. The invention also provides in one aspect an anti-GITR agonist antibody or antibody fragment for use in enhancing a T cell response in an individual. In a further aspect, the invention provides a composition comprising such an antibody or antibody fragment for use in enhancing a T cell response in an individual.

Conditions subject to treatment include cancers and infectious disease. For therapeutic purposes, the patient may have a cancer or tumor or an infectious disease, e.g., a bacterial, viral, fungal or parasitic infection. For preventative purposes, the patient may be in remission from a cancer or may anticipate being exposed to a bacterial, viral, fungal or parasitic infection. The antibodies can also serve as an adjuvant to enhance or promote or boost an immune response against a primary antigen or a target antigen, e.g., a vaccine.

In some embodiments, the patient has a cancer, is suspected of having a cancer, or is in remission from a cancer. Cancers subject to treatment with the anti-GITR antibodies usually express a tumor-associated antigen (TAA), as described herein. Cancers subject to treatment include without limitation epithelial cancers or carcinomas, as well as sarcomas and lymphomas. In some embodiments, the cancer is melanoma, ovarian cancer, renal cancer, colorectal cancer, prostate, lung cancer including non-small cell lung cancer (NSCLC), breast cancer, glioma, or fibrosarcoma. See, e.g., Pardee, et al, *Immunotherapy* (2009) 1(2):249-264, and references discussed therein. In some embodiments, the type of cancer is selected from the group consisting of: pancreatic cancer, melanomas, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues and head and neck squamous cell carcinoma (HNSCC).

In one aspect, the invention provides methods of treating tumor growth of a cancer that expresses a tumor associated antigen in an individual in need thereof, comprising administering to the individual a therapeutically effective amount of an anti-GITR agonist antibody or antibody fragment of the invention, as described herein. The invention also provides an anti-GITR agonist antibody or antibody fragment of the invention for use in treating tumor growth of a cancer that expresses a tumor associated antigen in an individual. The invention further provides a composition comprising an antibody or antibody fragment of the invention for use in reducing, inhibiting or preventing tumor growth of a cancer that expresses a tumor associated antigen in an individual.

In some embodiments, methods for facilitating the diagnosis or prognosis of cancer in an individual, comprising using an anti-GITR agonist antibody or antibody fragment of the invention for the detection of expression of GITR in or around a tumor in the individual.

In some embodiments, the patient has an infectious disease, for example, a bacterial, viral, fungal or parasitic infection. The anti-GITR agonist antibodies find use in reducing, inhibiting and/or preventing parasites in, e.g., filariasis and leishmaniasis.

In some embodiments, anti-GITR agonist antibodies find use in treatment of viral infections, including without limitation hepatitis virus infection, for example, chronic hepatitis C (HCV) infection, herpes simplex virus (HSV) infection or human immunodeficiency virus (HIV) infection. In some embodiments, anti-GITR agonist antibodies find use in treating a viral infection selected from the group consisting of: hepatitis type A, hepatitis type B, hepatitis type C, influenza, varicella, adenovirus, herpes simplex type I (HSV I), herpes simplex type II (HSV II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, human immunodeficiency virus type I (HIV I), and human immunodeficiency virus type II (HIV II), any picornaviridae, enteroviruses, caliciviridae, any of the Norwalk group of viruses, togaviruses, such as alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein Barr virus, human herpesvirus 6, cercopithecine herpes virus 1 (B virus), and poxviruses.

In some embodiments, anti-GITR agonist antibodies find use in treating bacterial infections, including without limitation an infection of *Neisseria* spp, *Streptococcus* spp, *S. mutans*, *Haemophilus* spp., *Moraxella* spp, *Bordetella* spp, *Mycobacterium* spp, *Legionella* spp, *Escherichia* spp, *Vibrio* spp, *Yersinia* spp, *Campylobacter* spp, *Salmonella* spp, *Listeria* spp., *Helicobacter* spp, *Pseudomonas* spp, *Staphylococcus* spp., *Enterococcus* spp, *Clostridium* spp., *Bacillus* spp, *Corynebacterium* spp., *Borrelia* spp., *Ehrlichia* spp, *Rickettsia* spp, *Chlamydia* spp., *Leptospira* spp., *Treponema* spp.

Administration of Anti-GITR Antibodies

A physician or veterinarian can start doses of the antibodies or antibody fragments of the invention employed in the pharmaceutical composition at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. Dosing can be daily, weekly, bi-weekly, monthly, or more or less often, as needed or desired. An exemplary treatment regime entails administration once weekly, once per every two weeks or once a month or once every 3 to 6 months.

In some embodiments, an polynucleotide encoding an anti-GITR antibody, antibody fragment, or antigen binding molecule of the invention is administered. In embodiments where the agent is a nucleic acid, typical dosages can range from about 0.1 mg/kg body weight up to and including about 100 mg/kg body weight, e.g., between about 1 mg/kg body weight to about 50 mg/kg body weight. In some embodiments, about 1, 2, 3, 4, 5, 10, 15, 20, 30, 40 or 50 mg/kg body weight.

The antibody or antibody fragment can be administered in single or divided doses. Antibody or antibody fragment is usually administered on multiple occasions. Intervals between single dosages can be weekly, bi-weekly, monthly or yearly, as needed or desired. Intervals can also be irregular as indicated by measuring blood levels of anti-GITR antibody or antibody fragment in the patient. In some methods, dosage is adjusted to achieve a plasma antibody or antibody fragment concentration of 1-1000 µg/ml and in some methods 25-300 µg/ml. Alternatively, antibody or antibody fragment can be administered as a sustained release formulation, in which case less frequent administration is required. Dosage and frequency vary depending on the half-life of the antibody or antibody fragment in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Co-Administration with a Second Agent

In some embodiments, the anti-GITR antibody, antibody fragment, or antigen binding molecule is co-administered with a second or third pharmacological agent. The anti-GITR antibody, antibody fragment, or antigen binding molecule and the second or agent can be administered as a mixture or in separate formulations. The anti-GITR antibody, antibody fragment, or antigen binding molecule and the second or agent can be administered concurrently or sequentially. The anti-GITR antibody, antibody fragment, or antigen binding molecule and the second or agent can be administered via the same route of administration or via different routes of administration, as appropriate. Exemplary second agents and third agents for co-administration with the present anti-GITR agonist antibodies, antibody fragments, or antigen binding molecules include without limitation, primary or target antigens, agents that increase the immunogenicity of a tumor cell, agents that inhibit or suppress co-inhibitory signals. The anti-GITR agonist antibodies, antibody fragments, or antigen binding molecules can also be co-administered with chemotherapeutic used to treat the disease condition being treated, e.g., to enhance the efficacy of the chemotherapeutic agent or to further enhance an immune response against a target antigen. The anti-GITR agonist antibodies, antibody fragments, or antigen binding molecules also find use in combination therapies with established procedures for treating the designated disease condition, e.g., radiation or surgery.

The anti-GITR antibodies, antibody fragments, or antigen binding molecules of the invention can be co-administered with a primary or target antigen. The target antigen, or vaccine, will depend on the disease condition to be treated. For example, the target antigen may be from a tumor cell, a bacterial cell, a fungus, a virus or a parasite. The target antigen can be in the form of a peptide, a polypeptide, a cell or a polynucleotide, as appropriate.

In some embodiments, the anti-GITR antibodies, antibody fragments, or antigen binding molecules are co-administered with a target antigen from a virus, e.g., selected from the group consisting of: hepatitis type A, hepatitis type B, hepatitis type C, influenza, varicella, adenovirus, herpes simplex type I (HSV I), herpes simplex type II (HSV II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, human immunodeficiency virus type I (HIV I), and human immunodeficiency virus type II (HIV II), any picornaviridae, enteroviruses, caliciviridae, any of the Norwalk group of viruses, togaviruses, such as alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein Ban virus, human herpesvirus 6, cercopithecine herpes virus 1 (B virus), and poxviruses.

In some embodiments, the anti-GITR antibodies, antibody fragments, or antigen binding molecules are co-administered with target antigen from a bacterium, e.g., selected from the group consisting of: *Neisseria* spp, *Streptococcus* spp, *S. mutans*, *Haemophilus* spp., *Moraxella* spp, *Bordetella* spp, *Mycobacterium* spp, *Legionella* spp, *Escherichia* spp, *Vibrio* spp, *Yersinia* spp, *Campylobacter* spp, *Salmonella* spp, *Listeria* spp., *Helicobacter* spp, *Pseudomonas* spp, *Staphylococcus* spp., *Enterococcus* spp, *Clostridium* spp., *Bacillus* spp, *Corynebacterium* spp., *Borrelia* spp., *Ehrlichia* spp, *Rickettsia* spp, *Chlamydia* spp., *Leptospira* spp., *Treponema* spp.

In some embodiments, the anti-GITR antibodies, antibody fragments, or antigen binding molecules are co-administered with a tumor-associated antigen (TAA). The TAA can be an isolated polypeptide or peptide, can be part of an intact cell or part of a tumor cell lysate. Exemplary TAAs are discussed above; others known in the art also find use.

In some embodiments, the anti-GITR antibodies, antibody fragments, or antigen binding molecules are co-administered with autologous tumor cells from the patient, or allogeneic tumor cells of the same tissue type from another patient. The tumor cells can be in the form of intact cells, tumor cell lysate, apoptotic tumor cells or total tumor mRNA. The tumor cells can be transfected to express a polypeptide that enhances or augments the immunogenicity of the tumor cell in the patient, e.g., transfected to express granulocyte colony stimulating factor (GM-CSF). The tumor cells can be from any cancerous tissue, including without limitation, epithelial cancers or carcinomas, as well as sarcomas and lymphomas. In some embodiments, the cancer is melanoma, ovarian cancer, renal cancer, colorectal cancer, prostate, lung cancer including non-small cell lung cancer (NSCLC), breast cancer, glioma, or fibrosarcoma. See, e.g., Pardee, et al, *Immunotherapy* (2009) 1(2):249-264, and references discussed therein. In one embodiment, the tumor cell is from, e.g., pancreatic cancer, melanomas, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues and head and neck squamous cell carcinoma (HNSCC).

In some embodiments, the anti-GITR antibodies, antibody fragments, or antigen binding molecules are co-administered with a cytotoxic agent. For example, the anti-GITR antibodies or antigen binding molecules are co-administered with a an agonist antibody or antigen binding molecule that binds to and reduces or depletes CD4+ CD25+ regulatory T cells (Treg). Exemplary Treg cell-depleting antibodies or antigen binding molecules bind to CD25 or CCR4. See, *Expert Opin Ther Patents* (2007) 17(5):567-575, and the references discussed therein.

In some embodiments, the anti-GITR antibodies, antibody fragments, or antigen binding molecules are co-administered with an inhibitor of a co-inhibitory signal. Exemplary inhibitors include inhibitors of CTLA-4, LAG3, TIM3 and/or inhibitors of the PD-1/PD-L1 (e.g., B7-H1) interaction. In some embodiments, the anti-GITR antibodies are co-administered with an antibody that binds to and inhibits CTLA-4. In some embodiments, the anti-GITR antibodies are co-administered with an antibody that binds to and inhibits TIM3. In some embodiments, the anti-GITR antibodies are co-administered with an antibody that binds to and inhibits LAG3. In some embodiments, the anti-GITR antibodies are co-administered with an antibody that binds to and inhibits PD-1. In some embodiments, the anti-GITR antibodies are co-administered with an antibody that binds to and inhibits B7-H1. See, e.g., *Expert Opin Ther Patents* (2007) 17(5):567-575; and Melero, et al., *Clin Cancer Res* (2009) 15(5):1507-1509, and the references discussed therein.

The anti-GITR antibodies, antibody fragments, or antigen binding molecules can also be co-administered with one or more immunostimulatory agents. For example, in some embodiments, the anti-GITR antibodies or antibody fragments are co-administered with an immunostimulatory cytokine, for example, IL-7, IL-12 or IL-15. Alternatively, the anti-GITR antibodies, antibody fragments, or antigen binding molecules can be co-administered with a second immunostimulatory antibody. For example, the anti-GITR antibodies, antibody fragments, or antigen binding molecules can also be co-administered with an agonist antibody, antibody fragment, or antigen binding molecule of another member of the tumor necrosis factor receptor superfamily. Exemplary secondary immunostimulatory targets include without limitation TNFRSF4 tumor necrosis factor receptor superfamily, member 4 (also known as OX40) or tumor necrosis factor receptor superfamily, member 9 (also known as TNFRSF9, 4-1BB or CD137). See, e.g., *Expert Opin Ther Patents* (2007) 17(5):567-575; Pardee, et al, *Immunotherapy* (2009) 1(2):249-264; and Melero, et al., *Clin Cancer Res* (2009) 15(5):1507-1509, and the references discussed therein.

The anti-GITR antibodies, antibody fragments, or antigen binding molecules can also be co-administered with a chemotherapeutic agent. The selected agent will depend on the condition to be treated, e.g., a cancer or an infectious disease, such as a bacterial infection, a fungal infection, a viral infection or a parasitic infection. The anti-GITR antibodies, antibody fragments, or antigen binding molecules can be co-administered with an chemotherapeutic known by those of skill to treat the disease condition being treated. Exemplary chemotherapeutic agents are discussed above; others known in the art also find use.

BRIEF DESCRIPTION OF THE DRAWINGS

FIG. 1A depicts results of hydrogen/deuterium exchange coupled to mass spectrometry (HDXMS) analyses using Fc-GITR fusion (top and middle trace) and HIS-GITR (lower trace) fusion proteins and MAB1 parental Ab. Numbering reflects removal of native GITR signal peptide (AA 1-26) sequence. FIG. 1B depicts a schematic of N-terminal deletion constructs prepared using the extracellular domain of human GITR (hGITR ECD). FIG. 1C depicts results of binding of MAB4 and MAB5 to hGITR ECD constructs. N-terminal deletion of cysteine-rich domain 1 (CRD1) from human GITR (hGITR) extracellular domain (ECD) abrogates binding of MAB4 and MAB5 to hGITR. Similar results were obtained for MAB7 (data not shown). FIG. 1D depicts results of alanine scanning mutagenesis. MAB7 bound to all mutant proteins with the exception of GITR mutant E78A. ForteBio™ binding analysis was carried out, and results also confirmed loss of MAB7 binding to hGITRE78A mutant protein (data not shown). Results implicates a region of ECD of GITR including CRD1 and including E78 (SEQ ID NO:88: RPTGGPGCG-PGRLLGTGTDARCCRVHTTRCCRDYPGEECCSEWD-CMCVQPEFHCGD) as a region and potential epitope involved in binding MAB1 and MAB7 (parental mAb).

FIG. 2A and 2B illustrates MAB4, and MAB5 specifically bind to GITR from human and cynomolgus monkeys (2A) but not from rodent (2B), as determined by ELISA assays. FIG. 2C illustrates MAB7 shares a similar profile binding human and cyno GITR but not murine GITR by ELISA assay. FIG. 2D illustrates MAB7 competes with GITR-ligand binding as determined by FACS competition analysis. FIG. 2E illustrates results of ELISA assays showing that the anti-GITR antibodies of the invention (e.g., MAB4, MAB5) do not bind to other members of the TNF receptor superfamily (TNFRSF). Protagen™ chip assays also confirmed that the antibodies do not bind to other off-target proteins (not shown).

FIG. 3A illustrates that recombinant human GITR ligand (GITR-L) activates intracellular signaling in 293 cells that have been stably transfected to overexpress human GITR. FIG. 3B illustrates that monoclonal antibodies MAB4 and MAB5 activate intracellular signaling in 293 cells that have been transfected to overexpress human GITR comparably to GITR-L when the antibodies are cross-linked ($EC_{50}$ for GITRL is about 65 nM versus $EC_{50}$ of about 2.5 nM for agonist antibodies in the presence of cross-linker). FIG. 3C illustrates that cross-linked MAB antibody activates intracellular signaling in cells, as MAB7 and MAB8 also promote NFκB activation in 293 cells stably transfected with human GITR and the NFκB-Luciferase reporter gene in a similar manner to cross-linked MAB4. FIG. 3D illustrates that Cross-linked MAB4 and MAB5 promote NFκB activation in 293 cells that have been stably transfected with cyno GITR and the NFκB-Luciferase reporter gene. Similar activation was seen with cross-linked MAB7 (data not shown).

FIG. 4A illustrates MAB7 is a co-activator of CD4+ T cells and stimulates T cell proliferation in CD4+ Tcells. FIG. 4B illustrates MAB7 is a co-activator of CD8+ T cells and stimulates T cell proliferation in CD8+ Tcells. FIG. 4C illustrates cytokine production, e.g. IFNγ production following TCR engagement is increased in conjunction with MAB7. Similar results were seen for MAB4 and 5 (data not shown).

FIG. 5A-D illustrates in vitro ADCC activity of MAB7 in GITR expressing cells at varying levels. FIG. 5A, FIG. 5B, FIG. 5C, and FIG. 5D each depict results of ADCC activity using control or MAB7 antibody with various levels of GITR expression. MAB7 is able to induce signaling through the FcgRIIIa, with increased activity upon increased levels of GITR signaling.

FIG. 6A depicts results showing expression of hGITR is upregulated on stimulated CD8+ T cells. FIG. 6B depicts results of of anti hGITR antibody binding to T cells by hFc staining, showing MAB7 can bind to hGITR expressed on mouse CD8+ T cells. FIG. 6C and 6D depict MAB7 binding to stimulated CD8+ T cells correlates with increased T cell activation, as shown by intracellular pIKK staining (6C) and T cell activation (6D). *$p<0.05$, ** $p<0.005$.

FIG. 7A-7C illustrates MAB7 is functional in vivo. hGITR-hGITRL double knock-in mice with established Colon26 tumors were treated with a single dose of vehicle (n=8/timepoint) or MAB7 (n=10/timepoint) antibody. FIG. 7A depicts results of tumor measurements twice per week and tumor volume calculated using the equation $(L \times W^2)/2$. Data shown is from the fifteen (15)-day time point group. FIGS. 7B and 7C depict results from whole blood and FIGS. 7C and 7D depict results from tumors were collected 3-days post-dose and analyzed by flow cytometry for cell surface hGITR expression on immune cells. (*$p<0.05$, ****$p<0.00005$).

FIG. 8A depicts results of Tregulatory cells 3-days post-dose. FIG. 8B-8C depict results of lymphocytes (8B) and activated CD8+ T cells (8C) present in tumor site following treatment levels in tumor 15-days post-dose. The absolute number of cells was normalized to tumor size to account for the significant difference in tumor size between Vehicle and MAB7 treated groups. FIG. 8D depicts Teff/Treg ratio resulting in treated animals as determined by total intratumoral activated CD8+ T cells compared to CD4+ FOXP3+ Tregs to generate $T_{eff}/T_{reg}$ ratios. FIG. 8E depicts results of splenocyte assays from purified CD8+ T cells incubated with Colon26 tumor cells ex-vivo, and measuring CTL response using IFNg ELISPOT assay. (*$p<0.05$, ***$p<0.0005$).

FIG. 9A depicts results of PD-1 positive cells assessed as a percentage of total CD19-CD3+CD8+ T cells. FIG. 9B depicts results of PD-1 positive cells normalized to tumor size by absolute number of PD-1+CD19-CD3+CD8+ T cells per $mm^3$ volume of tumor. FIG. 9C depicts results of PD-1 expression is upregulated on CD8+ T cells in spleens of Colon26 tumor bearing mice after treatment with DTA-1. PD-1 positive cells were assessed as a percentage of total CD19-CD3+CD8+ T cells. (*$p<0.05$ and ****$p<0.0005$).

EXEMPLIFICATION

Figure 1A:
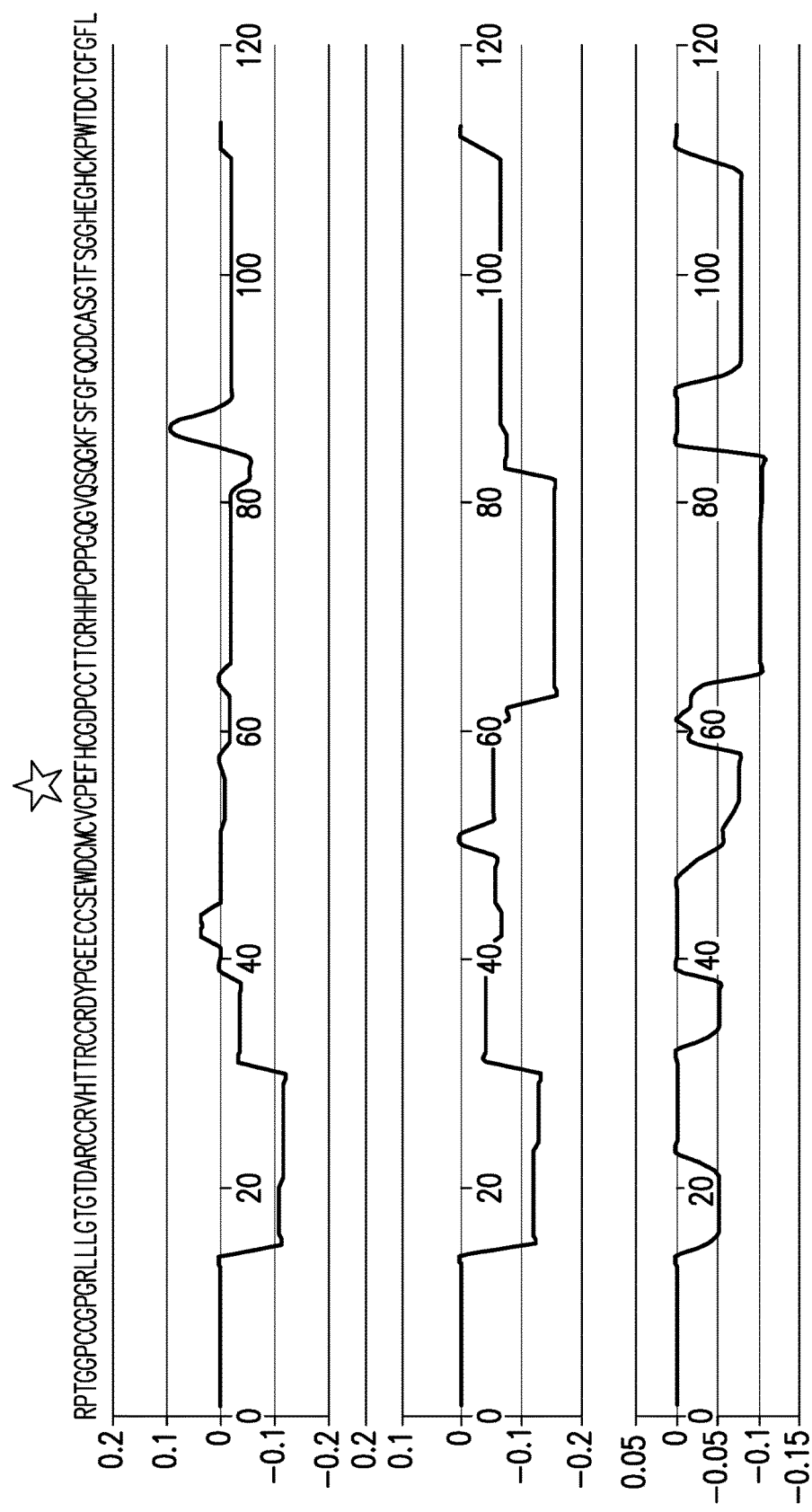
FIG. 1A-1D illustrate epitope mapping of the GITR mAbs of the invention.
Figure 1B:
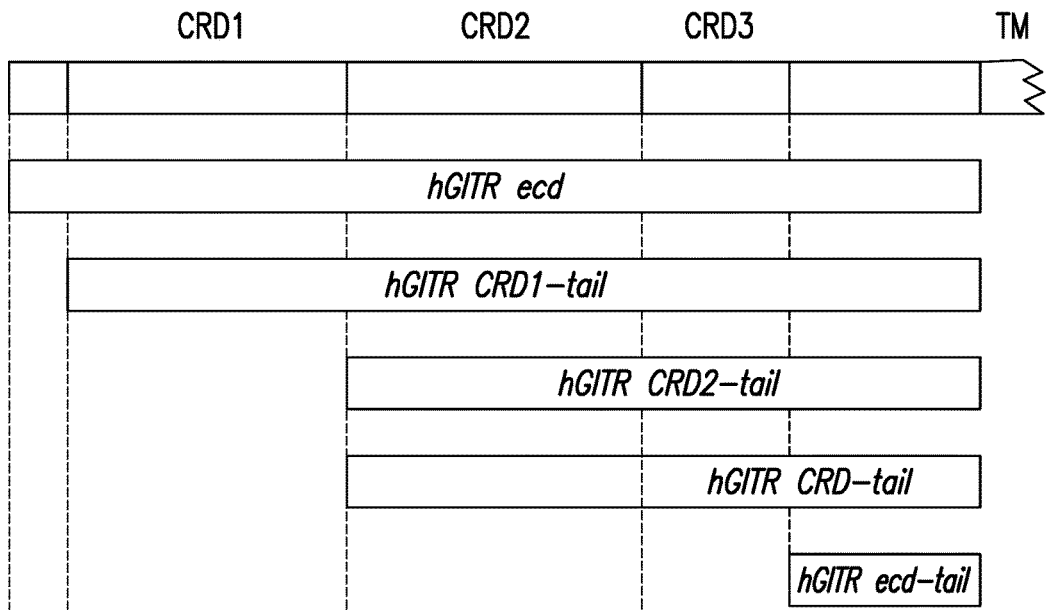
Figure 1C:
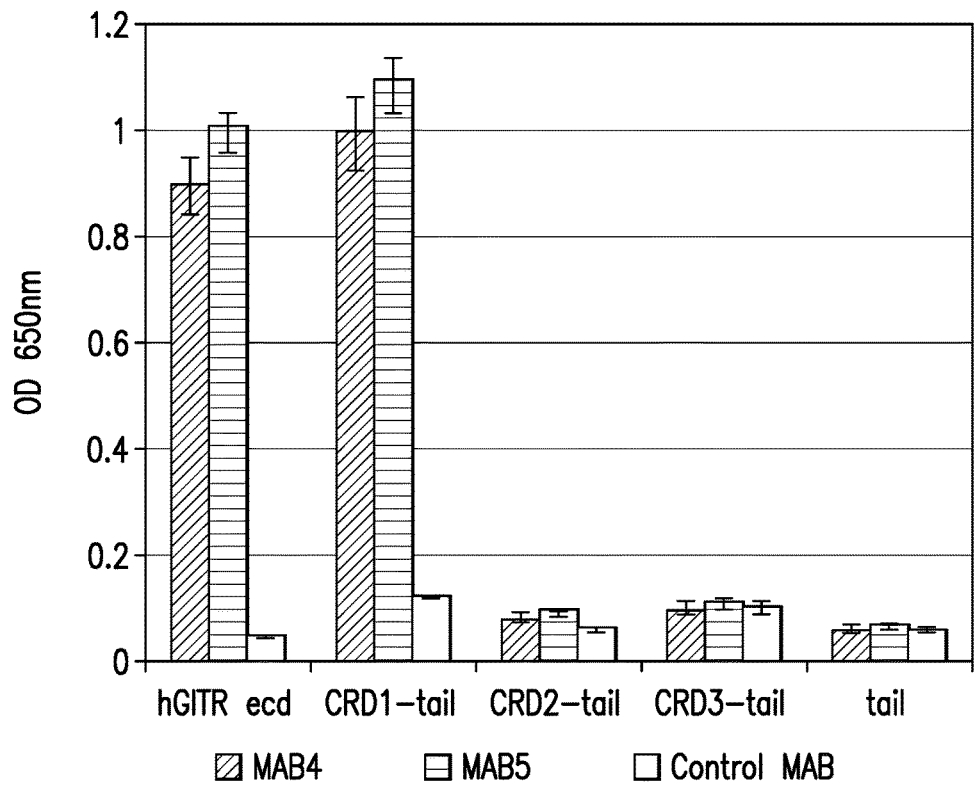
Figure 1D:
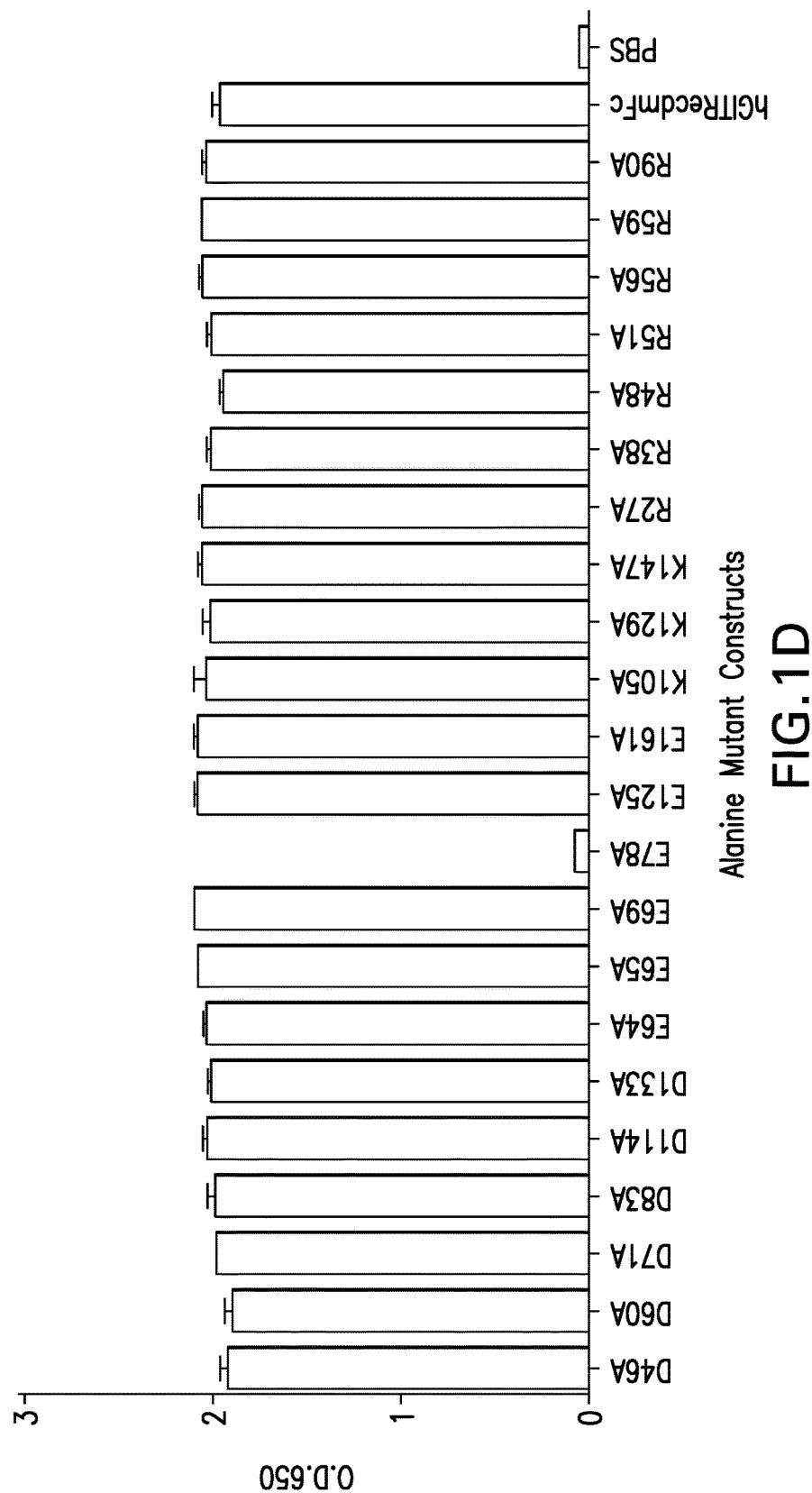

Creation of GITR Agonist Antibodies MAB2, MAB3, MAB4, MAB5, MAB6, MAB7 and MAB8

Human antibodies MAB2, MAB3, MAB4, MAB5, MAB6, MAB7 and MAB8 were generated by engineering a murine monoclonal GITR agonist antibody MAB1 to have greater sequence homology to a human germline antibody. MAB2, MAB3, MAB4, MAB5, MAB6, MAB7 and MAB8 retain the epitope specificity, affinity, and cynomolgus macaque GITR cross-reactivity of the parental murine antibody, MAB1, MAB2, MAB3, MAB4, MAB5, MAB6, MAB7 and MAB8 have much higher homology to the human germline sequence than the original murine antibody and should therefore be better tolerated by the human immune system.

Mouse monoclonal MAB1 was engineered to bring its protein sequence closer to a human germline sequence and decrease its immunogenicity using the Humaneered® technology platform available through KaloBios, (South San Francisco, Calif. (on the worldwide web at kalobios.com)). Humaneered® antibodies are very close to human antibodies with V-region sequences that have high homology to a human germline sequence while still retaining the specificity and affinity of the parent or reference antibody (U.S. Patent Publ. 2005/0255552 and 2006/0134098). The process first identifies the minimum antigen binding specificity determinants (BSDs) in heavy and light chain variable regions of a reference Fab (typically sequences within the heavy chain CDR3 and the light chain CDR3). As these heavy and light chain BSDs are maintained in all libraries constructed during the process, each library is epitope-focused, and the resulting Humaneered® antibodies retain the epitope specificity of the original mouse antibody.

Next, full chain libraries (in which an entire light or heavy chain variable region is replaced with a library of human sequences) and/or cassette libraries (in which a portion of the heavy or light chain variable region of the mouse Fab is replaced with a library of human sequences) are generated. A bacterial secretion system is used to express members of the library as antibody Fab fragments, and the library is screened for Fabs that bind antigen using a colony lift binding assay (CLBA). Positive clones are further characterized to identify those with the highest affinity. Identified human cassettes supporting binding in the context of residual murine sequences are the combined in a final library screen to generate completely human V-regions.

Resulting Humaneered® antibody Fabs have V-segment sequences derived from human libraries, retain the short BSD sequences identified within the CDR3 regions, and have human germline Framework 4 regions. These Fabs are converted to full IgGs by cloning variable regions of the heavy and light chains into IgG expression vectors. Humaneered® antibodies generated in this process retain the binding specificity of the parent, murine antibody, typically having equivalent or higher affinity for antigen that the parent antibody, and have V-regions with a high degree of sequence identity compared with human germline antibody genes at the protein level.

Methods

Generation of Murine Anti-GITR mAb MAB 1

Bcl-2 transgenic mice (C57BL/6-Tgn (bcl-2) 22 wehi strain) were immunized with the N-terminal region of human GITR (aa 26-161) using a procedure that calls for Repetitive Immunization at Multiple Sites (RIMMS) (McIntyre G D. Hybridoma 1997) followed by hybridoma generation from high titer mice. A hybridoma secreting MAB1 was identified and selected using a sandwich ELISA against hGITR and an NFκB Reporter Gene Assay to confirm hGITR binding and agonist activity.

Cloning of Murine V-regions

Variable region DNA from murine monoclonal MAB1 was amplified by RT-PCR from RNA obtained from the hybridoma cell line using standard methods. Heavy chain variable region was amplified from MAB1 cDNA with HV3 (5'-GGGTCTAGACACCATGGCTGTCTTGGGGCT-GCTCTTC-3' (SEQ ID NO:95)) and HCconstant (5'-GCGTCTAGAAYCTCCACACACAGGRRCCAGTGGA-TAGAC-3' (SEQ ID NO:96)). Light chain variable region was amplified from the same cDNA with LV3 (5'-GGGTCTAGACACCATGGAGWCACAKWCTCAG-GTCTTTRTA-3' (SEQ ID NO:97)) and LCconstant (5'-GCGTCTAGAACTGGATGGTGGGAAGATGG-3' (SEQ ID NO:19)). Variable heavy and light chain products were inserted into a pcDNA3.1 vector and sequence verified. The heavy and light vectors were used as templates for PCR incorporating restriction enzyme sites for cloning into KaloBios vectors: Vh into KB1292-His (modified version of KB1292 that encodes a C-terminal flexible linker and 6-His tag (SEQ ID NO:11) of amino acid sequence AAGASHH-HHHH (SEQ ID NO:13) on CH1) at NcoI (5') and NheI (3'); Vk into KB1296 at NcoI (5') and BsiWI (3'). These separate heavy and light chain vectors were then combined into a single dicistronic KaloBios Fab expression vector by restriction digest with BssHII and ClaI and ligation. Fab fragments were expressed in E. coli from this vector. This Fab was tested for hGITR-antigen binding and is referred to as MAB1rFab.

Fab Purification

Fab fragments were expressed by secretion from E. coli using KaloBios expression vectors. Cells were grown in 2×YT medium to an OD500 of ~0.6. Expression was induced by adding IPTG to 100 μM and shaking for 4 hours at 33° C. Assembled Fab was obtained from periplasmic fractions by osmotic lysis and purification by affinity chromatography using Ni-NTA columns HisTrap HP columns; GE Healthcare catalog #17-5247-01) according to standard methods. Fabs were eluted in buffer containing 500 mM imidazole and thoroughly dialyzed against PBS pH7.4 without calcium and magnesium.

Library Construction

To limit the complexity to identify complimentary human CDRs that support BSD-FR4 in human GITR binding, a cassette library approach, in which only part of the parent murine V-segment is replaced by a library of human sequences, was taken. The original murine MAB1 Vk is closest to human germline VkIII, so a mixture of two KaloBios libraries that contains VkIII germlines (KB1423 and KB1424) was used in making the Vk cassette libraries. KaloBios libraries that contains VH3 germlines (KB1413, KB1414) were used to construct Vh cassette libraries. Two types of cassettes were constructed by overlap PCR: front-end cassettes (8C1VK3FE-01, and MAB1VH3FE-01) containing human sequences in FR1, CDR1, and FR2, and FR3 cassettes (MAB1VK3FR3-01, and MAB1VH3FR3-01) containing human sequences in the FR3 were amplified using the above mentioned germline restricted KaloBios libraries. Each Vh cassette library was cloned into vector KB1292-His at NcoI (5') and KpnI (3'); each Vk cassette library was cloned into vector KB1296-B (modified version of KaloBios vector KB1296 which has a silent HindIII site added in FR4) at Ncol (5') and HindIII (3'). Resultant Vh or Vk plasmid libraries were then combined with the complementary chain from the optimized reference Fab (MAB1opVK or MAB1 opVH (e.g., the Vh front-end library was combined with the optimized reference Vk vector) by digestion with BssHII and ClaI and subsequent ligation to create libraries of dicistronic vectors expressing full Fabs.

No VH3 front-end clones bound the human GITR with high affinity, thus, a second VH3 front-end library (MAB1VH3FE-02) was constructed. This library contains human sequences in FR1, FR2, and a collection of CDR2s encoding either the parental murine residue or the selected human germline residue at all positions. The FR3 region sequences of this library were from six clones selected from the VH3FR3 library (MAB1VH3FR3-01).

The final Vk full-chain library (MAB1VK3FCL-01) was constructed by combining clones from VK front-end and VKFR3 cassette libraries with mutagenic VK CDR2s that encodes either the parental murine or the selected human germline residue at all positions. The resulting Vk full-chain library was cloned into KB1296b at NcoI and HindIII sites. This VK full-chain library was paired with a number of selected VH3FR3 library clones to allow functional Fab expression and screened by CLBS. The antigen specific clones were confirmed by human GITR specific ELISA and ranked by antigen affinity titration ELISA. The VH3 full-chain library (MAB1VH3FcL-01) was generated using the selected clones from the second VH3 front end library (MAB1VH3FE-02) with a collection of CDR2 sequences containing either the parental murine or human residue at each position. This VH full-chain library was cloned into KB1292-his at NcoI and KpnI sites. To yield the final full-chain human Fab expression library, selected VK full-chain clones were combined with VH full-chain library at BssHII and ClaI sites.

General ELISA

Recombinant human GITR and human Fc fusion protein (hGITR-hFc) was used for all ELISA assays. Typically, hGITR-hFc antigen diluted in PBS pH 7.4 was bound to a 96-well microtiter plate at 200 ng/well by overnight incubation at 4° C. After being rinsed three times with PBST, the plate was blocked with a solution of 1% BSA in PBS for one hour at 37° C., and then rinsed once with PBST. Fab-containing cell medium or diluted, purified Fab (50 μL) was then added to each well. After a one-hour incubation at 37° C., or overnight incubation at 4° C., the plate was rinsed three times with PBST. Anti-human-kappa chain HRP conjugate (Sigma #A7164) diluted 1:5000 in PBST (50 μL) was added to each well, and the plate was incubated for 45 min at room temperature. The plate was washed three times with PBST, then 100 μL of SureBlue TMB substrate (KPL #52-00-03) was added to each well and the plate was incubated for about 10 min at room temperature. The plate was read at 650 nm in a spectrophotometer.

Affinity Titration ELISA

In order to evaluate antigen binding of the selected Fab producing clones, an affinity titration ELISA was developed. This assay combines two consecutive ELISA steps: the first one, using goat anti-human Fab (Jackson ImmunoResearch Lab #109-005-097) capture and goat anti-human Kappa (Sigma #A7164) detection, measures Fab concentrations in cell culture medium to normalize the amount of Fab used in the second antigen titration ELISA; the second ELISA, a normal antigen specific ELISA, generates an antigen binding dilution curve with the same amount of starting Fab. By comparing the dilution curves of different clones the high affinity clones are identified.

Colony Lift Binding ELISA (CLBA)

Screening of Humaneered® antibody libraries of Fab fragments was carried out essentially as described in (U.S. Patent Publ. 2005/0255552 and 2006/0134098) using nitrocellulose filters coated with hGITR-hFC at 2.0 μg/mL in PBS pH7.4. Fabs bound to antigen-coated filter were detected using goat anti-human Kappa chain HRP conjugate (Sigma #A7164) diluted 1:5000 in PBST, and blots were developed with ECL plus Western Blotting Detection System (GE Healthcare #RPN2132).

Removal of Glycation Site in MAB4

A glycation site "KH" in the junction of FR3 and CDR3 of MAB4 heavy chain was removed by replacing the lysine with an arginine, or replacing the lysine with an arginine and the histidine with an Asparagine. The KH to RH and KH to RN conversions were accomplished by PCR based mutagenesis using the p50H plasmid as the DNA template. The reverse primer (TCTGGCGCAGTAATACACGGCC, SEQ ID NO:110) incorporated an arginine in place of the lysine; the forward primer (NNKGCCTATGGCCATGATGGCG, SEQ ID NO:111) had the degenerate NNK trinucleotide at the histidine site. PCR reactions were performed with 100 ng of template, 0.2 μM of each primer, 200 μM dNTPs, and 2.5 U of pfuUltraII DNA polymerase (Strategene) in a 500 reaction volume. The PCR conditions were 94° C. for 3 min for 1 cycle; 94° C. for 15 seconds, 52° C. for 20 seconds, and 65° C. for 5minutes for 30 cycles; and finally, 1 cycle at 72° C. for 5 minutes. DpnI (2 U) was added to the PCR reaction and incubated at 37° C. for 30 minutes to remove the template p50H. Amplified MAB4 heavy chain variants were separated by a 1% SYBR gel and purified using a Qiagen Gel Purification Kit. The gel purified PCR product was treated with T4 DNA polynucleotide kinase, ligated and transformed into DH5α chemically competent cells (Invitrogen) under ampicillin selection.

Clones hosting the MAB7 and MAB8 heavy chain were selected by colony PCR using the forward (GC-CTTTCTCTCCACAGG, SEQ ID NO: 112) and reverse (GGCAAACAACAGATGGCTGG, SEQ ID NO:113) primers following GoTaqClear protocol (Promega). The PCR conditions were 94° C. for 3 minutes for 1 cycle; 94° C. for 10 seconds, 55° C. for 30 seconds, 72° C. for 45 seconds for 25 times; and finally, one cycle at 72° C. for 5 minutes. PCR reactions were cleaned up for sequencing by incubating the samples at 37° C. for 30 minutes and 80° C. for 15 minutes with Exonuclease I and Shrimp Alkaline Phosphatase. PCR samples were sequenced and the results were analyzed using Clone Manager software.

Antibody Production and Purification

Generated antibodies MAB2, MAB3, MAB4, MABS, MAB6, MAB7 and MAB8 (IgG1 kappa) were produced by co-transfection of vectors as follows into 293 Freestyle cells using 293fectin transfection reagent (Invitrogen #51-0031) according to the manufacturer's protocol.

MAB2—p35H+p35kappa
MAB3—p38H+p38kappa
MAB4—p50H+p35kappa
MAB5—p51H+p35kappa
MAB6—p56H+p35kappa
MAB7—pMAB7H+p35kappa
MAB8—pMAB8H +p35kappa Antibody was purified from 293 Freestyle cells supernatants using a 5-mL HiTrap Protein A HP column (GE Healthcare #17-0403-03). Antibody was eluted using IgG Elution Buffer (Pierce #21004), and buffer exchanged into PBS by dialysis. Protein A affinity chromatography was performed on an AKTA-FPLC liquid chromatography system (GE Healthcare).

Specificity ELISA

For the specificity ELISA, a crude cell lysate was made from bacteria expressing members of the TNFRSF family. To prevent nonspecific binding to the plate 50 μL of 5% BSA was added per mL of bacterial lysate. A HisGrab Nickel 96-well plate (Pierce #15142) was coated with TNFRSF containing bacterial lysate at 100 μL of lysate/BSA per well and incubated for 1 hour at room temperature. The plate was then rinsed three times with PBST, then MAB was diluted to 0.5 μg/mL in 10% FBS in PBS and 100 μL was added to each well. The plate was incubated for 1 hour at room temperature and then rinsed three times with PBST. Anti-human kappa antibody (Sigma #A7164) conjugated to HRP was diluted 1:5000 in 1:1 PBST: 10% FBS in PBS and 100 μL added to each well. The plate was incubated for 1 hour at room temperature, and then washed three times with PBST. 100 μL of SureBlue TMB substrate was added to each well and the plate was incubated for about 10 min at room temperature before stopping the reaction with 100 μL /well of 2N $H_2SO_4$. The plate was read at 450 nm in a spectrophotometer.

ELISA (GITR Binind, Species Cross-reactivity, Alanine Scanning)

Binding of the MABs to GITR from various species, various alanine mutant constructs or GITR extracellular domain- was assessed using a 384-well plate was coated with rat, mouse, human or cyno GITR extracellular domain (ECD) at 50 ng per well and incubated overnight at 4° C. The plate was blocked with a solution of 1% BSA in PBS for one hour at room temperature and then rinsed three times with PBST. The MAB was then diluted to 0.5 μg/mL or 1 μg/mL in PBS and 20 μL was added to each well. The plate was incubated for 1 hour at room temperature and then washed three times with PBST. Anti-human kappa antibody (Sigma #A7164), anti-human gamma antibody (Jackson Immunoresearch 109-036-098), goat anti-mouse antibody (Jackson ImmunoResearch 115-035-071) conjugated to HRP was diluted 1:5000 in Blocking Buffer (25 μL) and added to each well, or a hrp conjugated HIS antibody (QIAGEN 1014992) diluted 1:1000 in Blocking Buffer was added. The plate was incubated for 1 hour at room temperature, and then washed six times with PBST. 25 μL of SureBlue TMB (KPL 52-00-02) substrate was added to each well and the plate was incubated for about 10 min at room temperature. Plates were read at 650 nm in a spectrophotometer.

Cell Lines, Cells
Cell Lines

To generate the 293-hGITR-NFκB reporter gene cells line, 293 cells were stably transfected with an NFκB-Luciferase reporter gene and human GITR (or cyno GITR). Activation of the GITR signaling pathway in these cells was determined by measuring the levels of luciferase induced within the cells after a 24 hour incubation with GITR-L or agonistic antibody. To assess the effects of cross-linking Abs, they were incubated with an excess of a F(ab')$_2$ goat anti-human Fcγ fragment specific antibody or protein A before using in the reporter gene assay.

Clonal Daudi cell lines were generated that express levels of GITR seen on human immune cells.

Cynomolgus monkey PBMCs were prepared and GITR binding determined using MABs. Briefly, cynomolgus blood was transferred into 50 mL conical tubes (Falcon, #352098), then diluted 1:2 in PBS (HyClone, #SH30256.01) and mixed. Diluted blood was carefully layered on top of 18 mL of 90% Ficoll Paque PLUS (GE Healthcare #17-1440-03 diluted in PBS), and tubes were spun at 2,000×g in a bench top centrifuge for 30 minutes at room temperature, with no brake. The plasma layer was carefully removed without disturbing the diffuse PBMC layer on top of the Ficoll. PBMCs were then carefully harvested and PBS was added to the isolated PBMCs until the volume in the conical tube was 45 mL, mixed, and then spun at 300×g in a bench top centrifuge for 15 minutes at room temperature. Supernatant was carefully aspirated and 4 mL of lx BD Lysing solution (BD #555899) was added and the samples were gently vortexed. After incubating at room temperature in the dark for 3 minutes, 40 mL of PBS was added to each sample and they were spun at 200×g in a bench top centrifuge for 10 minutes at room temperature. Supernatant was carefully aspirated and the pellet was washed two times in 45 mL of PBS before being spun at 200×g in a bench top centrifuge for 10 minutes at room temperature. Resulting pellet was filtered and resuspended at 1×10$^6$ cells/mL in CTL Test media (CTLT-005) supplemented with penicillin/streptomycin/glutamine (Hyclone #SV30082.01). 100 μL of purified cynomolgus PBMCs were placed in a 96 well round bottom plate (Corning, #3799). To activate the PBMCs, 100 μL of M-280 Tosylactivated dynabeads (Life Technologies #142.04) conjugated with SP34-2/CD28.2 antibodies was added to each well. A ratio of 3:1 CD3/CD28 Beads to PBMCs was used and the plates were incubated in a 37° C. tissue culture incubator for 48 hours. For day 0 staining 200 μL of PBMCs was placed in a 96-well round bottom plate (Corning, #3799). For samples that were stimulated for 48 hours 100 μL of supernatant was carefully removed and the remaining content of the well was carefully resuspended and 200 μL transferred to the FACS staining plate.

FACS

Plates were prepared with cells resuspended in 200 μL of cold PBS. LIVE/DEAD fixable stain (Life Technologies #L23105) was reconstituted in 50 μL of DMSO and 1 μL of reconstituted stain was added/mL of cold PBS, and cell pellets were immediately resuspended in 100 μL of the LIVE/DEAD PBS solution, incubated for 30 minutes on ice protected from light, then washed and resuspended in 100 μL of cold FACS Buffer containing 2 μg/mL of MAB7 or an Isotype Human IgG1 control antibody and plates incubated for 30 minutes on ice protected from light. Wash and resuspension in in 100 μL of antibody cocktail (PerCP Cy5.5 anti-human CD3 (BD #552852), Alexa Fluor 700 anti-human CD4 (BD #560836), V450 anti-human CD8 (BD #561426), PE-Cy7 anti-human CD25 (BD #561405) and PE anti-human in FACS Buffer (Jackson Immuno #109-116-098)) followed and plates were then incubated for 30 minutes on ice protected from light and then spun in a bench top centrifuge at 3,200 RPM for 1 minute at 4° C. Cells were washed in FACS Buffer then resuspended in 100 μL of BD CytoFix (BD #554655) and plates were incubated for 15 minutes at room temperature protected from light then washed twice and resuspended in 100 μL of FACS Buffer. Plates were covered with foil (Beckman Coulter, #538619) and stored at 4° C. until ready to read. On the day of FACS read the plate was spun in a bench top centrifuge at 3,200 RPM for 1 minute and 50 μl of CML latex beads (Life Technologies #C37259), 4×10$^5$/mL in FACS Buffer, was added to each well. The plates were read on a BD Fortessa flow cytometer and data analyzed using FlowJo.

Transgenic Mice hGITR knock-in mice were generated by replacing the entire coding sequence (exons and introns) of mouse GITR with the human GITR cDNA sequence. Untranslated sequences upstream of the start codon and downstream of the stop codon are from mouse genome. Gene targeting was done by standard techniques in BALB/c ES cells with targeting vectors bearing BALB/c derived homology arms. Several ES cell clones were identified by PCR and confirmed by Southern blotting to contain the exact human cDNA knockin. Following standard mouse embryology techniques, positive ES cell clones were injected into blastocysts, which were transferred into pseudopregnant recipient foster mothers to derive chimeric offspring. Male chimeric mice were crossed with BALB/c females expressing Cre recombinase in their germline to excise the loxP flanked neomycin resistance cassette. One clone resulted in white offspring indicating germline transmission of the targeted ES cells. Excision of the loxP-flanked cassette was confirmed by PCR genotyping. A subsequent breeding step with BALB/c wt mice removed the Cre recombinase.

hGITRL knock-in mice were generated by replacing mouse the coding portion of exon 1 with the human GITRL cDNA sequence followed by a bovine growth hormone poly-A signal. All ES cell work and mouse embryology were done similar to the procedures described above. hGITR-hGITRL double knock-in mice were generated by intercrossing the two founder lines for 2 generations to produce homozygous double knock-in mice.

Functional Assays

Functional activity of MABs were tested in an NFkB reporter gene assay for agonist activity. MAB was diluted to 6 μg/mL in PBS and incubated for 30 minutes at room temperature in the presence/absence of a 3 fold excess of F(ab')$_2$ fragment goat anti-human Fcγ specific crosslinker. Alternatively, MAB was diluted to 6 μg/mL in PBS and incubated for 30 minutes at room temperature in the presence/absence of a 2 fold excess of Protein A. 10 μL of incubated MAB was then added to a 384 well white clear bottomed assay plate. A HEK-293 cell line stably transfected with hGITR and a NFκB reporter gene was diluted to $5\times10^5$ cells/mL and 20 μL of the cell suspension was added to each well. The plate was incubated for 24 hours in a 37° C. tissue culture incubator. 30 μL of Cell Bright Glo was added to each well and the plate was read for luminescence on the Acquest.

The ability of MAB to block ligand binding was assessed using HEK293 NFκB reporter parental cells and hGITR stable cells were used in competition binding assays and FACS analysis. Briefly, harvested cells were plated $1\times10^6$ cells per mL, 100 μL per well to a 96 well round bottom FACS plate (Corning), then resuspended in 200 μL of cold FACS buffer (1×PBS+1% FBS-HI+0.1% sodium azide) per well. Human GITR ligand titration was prepared from 270 nM to 1.52 pM in FACS buffer at 100 μL per well. Plates were incubated for 1 hour on ice protected from light, cells washed, then prepared 4 nM isotype control or MAB solutions were prepared and added to appropriate wells at 100 μL per well and plates were incubated for 1 hour on ice protected from light, cells washed, then PE-conjugated goat-anti-human detection antibody (Jackson ImmunoResearch) prepared at 1:100 dilution in FACS buffer was added at 100 μL per well and plates were incubated for 30 minutes on ice protected from light. Cells were washed in FACS buffer then cells were fixed with 100 μL per well of BD CytoFix (BD Biosciences) and incubated for further 15 minutes on ice protected from light. Fixed cells were washed twice, resuspeded at a final volume of 150 μL per well of FACS buffer, and samples analyzed within 1 week on a BD Fortessa flow cytometer (BD Bioscience).

Agonist activity of MABs could also be seen on primary T cells that express endogenous levels of GITR via proliferation and cytokine secretion from primary T cells. MABs were conjugated on to M-280 Tosylactivated beads (Invitrogen #142.04) following the manufacturer's instructions. In some experiments agonist CD3 (OKT3) and CD28 (CD28.2) antibodies were also conjugated to beads. $1\times10^5$ freshly purified CFSE-labelled human PBMCs were plated in 10 uL of CTL Test media (CTL #CTLW-010) into a 96 well round bottomed tissue culture plate. 100 uL of MAB conjugated beads was then added at a ratio of 1 T cell: 1 beads. Plates were then incubated for 3 days in a 37° C. tissue culture incubator. Levels of secreted cytokines in the media were measured using a MSD multiplex assay according to manufacturer's instructions. Cells were stained with anti-CD4, -CD8a, -CD25, -GITR antibodies and a LIVE/DEAD stain after staining cells were fixed and read on the flow cytometer. Proliferation of each CD4 and CD8 cells was assessed by CFSE staining and counting beads were added prior to the FACS read to allow normalization of the samples.

Co-stimulatory activity of MABs on T cells was also measured using an ELISpot method for detection of IFNg. Briefly, ELISPOT plates (Millipore MSIPS4510) were prepared by coating with 70% ethanol for 2 minutes followed by PBS wash and incubation overnight with 50 ug IFNg monoclonal antibody in PBS (Mabtech 3321-3). Purified CD8+ T cells were isolated from spleens of Vehicle or MAB7-treated mice 15-days post-dose. T cells were plated into the coated ELISPOT plates at $0.25\times10^{\wedge}6$ cells per well in CTL media (CTL Test-medium (CTL CTLT-005), 1 mM Hepes (Mediatech MT25-060-C1), 2 mM L-glutamine (Mediatech MT25-005-C1), 1 mM sodium pyruvate (Mediatech MT25-000-C1), 100 uM MEM Non-essential amino acids (Mediatech MT25-025-C1), 66 uM 2-Mercaptoethanol (Gibco 21985-023), 100 U/mL Pten/Strep (Gibco 10378016). Colon26 cells were treated with 10% ConA sup (BD Biosciences 354115) at 37° C. for 48 hours to upregulate MHC Class II expression and washed with CTL media prior to addition to T-cells. Colon26 tumor cells (20,000/well) were added to CTLs and incubated at 37° C. for 24-48 hours. Plates were then washed with 0.05% Tween-20/PBS and 10 ug of biotinylated anti-IFNg Mab (Mabtech R4-6A2-biotin) was added to each well and incubated for 2 hours at 37° C. Plates were then washed with 0.05% Tween-20/PBS and Vectastain ABC solution (Vector Labs PK6100) was added to each well and incubated for 1 hour at room temperature. Cells were then washed with 0.05% Tween-20/PBS and AEC substrate, prepared according to manufacturer's protocol (Sigma A6926) was added to each well and incubated for 4 minutes at room temperature. Plates were then rinsed with tap water, dried and stored in the dark for 24 hours prior to reading.

The ability of MABs to induce ADCC was measured using a reporter assay. In a 96 well white plate (Perkin Elmer F6178) $2\times10^3$ hGITR-Daudi cells were incubated with $4\times10^4$ Jurkat-V158 cells (stably expresses the V158 variant of the human FcgRIIIa and an NFAT reporter) at a ratio of 1 Daudi cell to 20 Jurkat) cells in 50 uL of RPMI+10% FBS. An equal volume of MAB was added to the well and the plates was incubated for 3 hours in a 37° C. tissue culture incubator. After the incubation 60 uL of Bright-Glo was added to each well and the plate was read on a luminometer.

In vitro splenocyte assays were carried out using spleens isolated from mice. Briefly, spleens from mice were dissociated by automated homogenization in 5 mL AutoMACS Rinsing Solution (Miltenyi Biotech 130-091-222) containing 5% BSA (Miltenyi Biotech 130-091-376) using gentleMACS C tubes (Miltenyi Biotech 130-096-334) on a gentleMACS Octo Dissociator (Miltenyi Biotech 130-095-937). Homogenates were strained through a 0.70 uM pore size cell strainer (Fisher Scientific 22363548) and washed with 10 mL AutoMACS buffer. Splenocytes were resuspended and plated at 100,000 cells/well in RPMI (HyClone SH30027.02)+10% human serum (Cellgro 35-060.C1)+1× Pen/Strep/L-Glut (Gibco 15 140-112) in a 96-well tissue culture plate (Costar 3799). For T-cell stimulation, 0.4 ug/mL of anti-mouse CD3 (eBioscience 16-0031-86) and 0.8 ug/mL of anti-mouse CD28 (eBioscience 13-0281-86) antibodies were added to appropriate wells. After 48 hours, cells were either analyzed immediately or pulsed with control or therapeutic antibody for 30 minutes to 96 hours, stained with fluorophore-conjugated antibodies and analyzed by flow cytometry.

Flow cytometry: For surface markers, cells were stained with anti-CD19 (BD Biosciences 562291), anti-CD8 (Biolegend 100725), anti-CD4 (eBioscience 25-0041), anti-CD69 (BD Biosciences 561238), anti-hGITR (Miltenyi Biotech 130-092-895) and anti-hIgG (Life Sciences A-10631) antibodies for 30 minutes at 4 C. For intracellular staining, following incubation with cell surface antibodies, cells were washed, fixed and permeabliized with FOXP3 Fix/Perm buffer (Biolegend 421403) according to manufacture's protocol and incubated with anti-phospho-IKKa/b antibody (Cell Signaling 2697) or anti-FOXP3 antibody (eBioscience 50-4774-42) for 30 minutes at 4 C. Cells were read on a BD LSRFortessa cytometer using BD FACSDiva software (BD Biosciences) and flow data was analyzed using FlowJo software (TreeStar Inc.).

Single cell suspensions were generated from tumors and spleens and stained for analysis by flow cytometry. For example, cell markers were assessed using the following antibodies: a-CD8-BUV395 (clone 53-6.7, BD Biosciences 563786), a-CD19-APC-Cy7 (clone 6D5, BioLegend 115530), a-CD3-PerCp (clone 145-2C11, BD Bioscience 553067), a-PD-1-PE-Cy7 (clone RMP1-30, Biolegend 109110). Flow cytometry was run on BD LSRFortessa cytometers using BD FACSDiva software (BD Biosciences). Cytometry data was analyzed using FlowJo Software (FlowJo LLC). Graphs were generated and statistics run using Prism software (GraphPad Software). All data were shown as mean±standard deviation (SD). Group comparisons were carried out using student's T-test with two-tailed 95% confidence interval. For all statistical evaluations the level of significance was set at p<0.05. Significance compared to the vehicle control group is reported unless otherwise stated.

In vivo tumor models. The Colon26 murine colon carcinoma cell line was obtained from the Division of Cancer Treatment and Diagnosis at the National Cancer Institute (vial: 0507238). Murine Colon26 carcinoma cells were cultured in RPMI 1640 medium (HyClone SH30027.02) supplemented with 10% FBS (Gibco 10099-141), 10 mM HEPES (Gibco 15630-080) and 1 mM sodium pyruvate (Gibco 11360-070). 8-10 week old female hGITR-hGITRL knock-in mice were injected subcutaneously with $0.5 \times 10^{\wedge}6$ Colon26 cells in 100 uL of RPMI in the flank. Tumors were measured using digital calipers and tumor volume calculated using the equation $(L \times W^2)/2$. When tumors reached an average size of 180 mm$^3$, mice were randomized and dosed with a single intraperitoneal injection of vehicle (PBS) or therapeutic antibody (15 mg/kg) in 200 uL PBS. Mice were sacrificed and tumors collected for analysis by flow cytometry 7 days after dosing with therapeutic antibodies. All animal experiments were performed in an AAALAC accredited facility using IACUC approved protocols. Statistical analysis was performed in Prism software using student's t-test with two-tailed 95% confidence interval or One-way ANOVA with Tukey correction.

Surrogate murine GITR Colon26 model testing. Charles River Labs female 6-8 week old BALB/c mice were used as the experimental animal. For implantation, cells were resuspended in Hank's 1× Balanced Salt Solution (Hyclone Cat# SH30030.02) and implanted with a subcutaneous injection into the right lower flank using a 28 g needle (100 ml injection volume). After implantation, mice were randomized according to tumor volume. Mice were dosed with 5 mg/kg of IgG2a-DTA-1 or mouse IgG2a isotype control by subcutaneous injection. Clone DTA-1, a rat anti-mouse GITR antibody (S. Sakaguchi, Kyoto University, Kyoto Japan) was modified to create a murine chimeric IgG2a by fusing the DTA-1 variable region sequences to murine IgG2a Fc regions to create IgG2a-DTA-1.

Combination Therapy. To assess in vivo activity of surrogate anti-GITR antibody (mouse IgG2a-DTA-1),in combination with surrogate anti-PD-1 antibody (rat, IgG2a RMP1-14, Biolegend), female 6-8 weeks old BALB/cJ mice from Jackson Laboratories (Bar Harbor, Me.) were implanted subcutaneously in the right supra-axillary region with $5 \times 10^5$ Colon26 cells in a volume of 100 uL. For implantation, Colon26 cells were suspended in Dulbecco's PBS, calcium and magnesium free from Lonza (17-512 F). Mice were enrolled in the study ten days post implantation with a mean±SEM tumor volume of 115 mm$^3$±7. After being randomly assigned to one of 4 groups (n=10-16/group), mice were dosed concurrently once weekly for 2 weeks with isotype (group1), RMP1-14 (10 mg/kg, group2), IgG2a-DTA-1 (5 mg/kg, group3) or the combination of RMP1-14 and IgG2a-DTA (10 mg/kg and 5 mg/kg, respectively, group 4) as described in Table 6. Day 0 is defined as the day of randomization. The isotype control group contained mIgG2a (Biolegend) at 5 mg/kg and rat IgG2a (Biolegend) at 10 mg/kg. IgG2a-DTA and its isotype control (mIgG2a) were dosed via subcutaneous injection at 5 mg/kg. RMP1-14 and its isotype control (rIgG2a) were dosed via intraperitoneal injection. Dosing volume was 10 mg/mL for all treatments. Body weights and tumor volumes were collected two-three times per week. Individual animals were scored as achieving end point when tumor volumes equaled or exceed 1200 mm$^3$. Anti-tumor activity was reported based on changes in the median time to endpoint (TTE), assessed by Kaplan-Meier survival analysis.

Combination Therapy. To assess expression of costimulatory molecules following administration of anti-GITR or anti-GITR in combination with anti-PD-1, single cell suspensions of whole tumors and spleens were profiled by flow cytometry following 1 dose of a GITR (clone IgG2a-DTA-1) or anti-PD1 (clone RMP1-14) or anti-GITR+PD1 in combination. mIgG2a was used as control. LAG5, TIM3 and PD-1 positive cells were assessed as a percentage of total CD3+CD8+ T cells in tumors and spleens. Pvalues are calculated with t-test. *p<0.05 and **p<0.005.

Results

Murine and Reference V-region Amino Acid Sequences

RT-PCR products from hyrbidoma cells that express MAB1 were sequenced, and this sequence was largely (95% or greater) verified at the protein level using a ThermoElectron LTQ-Orbitrap Mass Spectrometer. The heavy and light chain variable regions of MAB1 were then cloned in KaloBios vectors in order to create the reference Fab MAB1rFab. The first amino acid in MAB1 has to be changed from an asparagine (N) to a glutamic acid (E) residue to enable cloning into KaloBios vectors for generation of the reference Fab; therefore, the MAB1rFab has glutamic acid at the first VK position. The Fab MAB1rFab has intact murine V-regions from MAB1 fused with human constant regions. In addition to MAB1rFab, an optimized Fab, MAB1opFab, was constructed. Several framework amino acid residues in MAB1rFab were changed to human germline residues in MAB1opFab.

Reference and Optimized Reference Fab Affinity Analysis

Human germline residues incorporated into the optimized reference MAB1opFab in FR1 and FR3 are those specified by the PCR primers used to amplify the human V-segment repertoire and thus are present in all members of the Humaneered® Antibody V-region libraries. The optimized reference Fab is constructed to assess whether or not any of the changes to human germline alter the properties of Fab binding. Affinity constants (Ka (1/Ms), Kd (1/s), and KD (M) of MAB1rFab, MAB1opFab was assayed using the ForteBio Octed QK system and Striptavidin High Binding Biosensors coated with biotinylated hGITR-hFc. Compared with MAB1rFab, MAB1opFab, had very similar Kd, but five-fold improvement on Ka indicating that the amino acid changes in MAB1rFab are tolerated.

Library Construction and Selection of Humaneered®Antibody Fabs

Heavy and light chain front-end and FR3 cassette libraries, germline-family restricted to VH3 and VKIII, were generated and screened by CLBA. For VK, clones that support binding to human GITR were identified from both VK front-end (MAB1VK3FE-01) and FR3 (MAB1VK3FR3-01) cassette libraries. For VH, clones that support binding to human GITR were identified from FR3 cassette library (MAB1VH3FR3-01), but not from the VH3 front-end library (MAB1VH3FE-01). Since the majority members in Vk front-end and FR3 cassette libraries were positive in CLBA, the whole repertoire of these two libraries was used to construct Vk full-chain library (MAB1VK3FcL-01) by overlapping PCR with mutagenic VK CDR2s that encodes either the parental murine or the selected human germline (VKIII L-16) residue at all positions. A number of hGITR positive clones were identified from VH3FR3 library (MAB1VH3FR3-01) through CLBA and confirmed by human GITR specific ELISA. Six of them were used to pair with VK full-chain library (MAB1Vk3FcL-01) to enable functional Fab expression and the screen of this library.

Since there were no clones that bind hGITR with high affinity were identified from VH front-end library (MAB1VH3FE-01), subsequently, a second VH3 front-end library (MAB1VH3FE-02) was constructed. This library has either the parental murine or human germline (VH3 3-30) residue at each position of CDRland the FR3 sequences from the six selected VHFR3 clones. Many hGITR binders were identified from both VK full-chain library (MAB1Vk3FcL-01) and the second VH front-end library (MAB1VH3FE-02). These clones were confirmed by human GITR specific ELISA assay on Fab-containing cell supernatants and rank-ordered by hGITR affinity titration ELISA.

Based on hGITR affinity titration ELISA, four VK full-chain clones were selected from VK full-chain library (MAB1VK3FcL01), and six clones were selected from MAB1VH3FE-02 library. The six VH clones were used as the backbone to construct the VH full-chain library with either MAB1 murine or the closest human germline (VH3 3-30) residue at each position in CDR2. This VH full-chain repertoire was paired with the four VK full-chain clones to form the final human full-chain Fab library. CLBA identified many hGITR binding clones, that were confirmed by ELISA using the respective culture supernatant as the Fab source. Five human full-chain Fab clones (MAB2, MAB3, MAB4, MAB5, and MAB6) were selected based on DNA sequence analysis and hGITR affinity titration ELISA results.

Testing the Affinity of Humaneered® Antibody Fabs for GITR Antigen using ForteBio Octet Analysis The five human full-chain Fabs (MAB2, MAB3, MAB4, MAB5, and MAB6) were expressed and purified. The binding kinetics of these human Fabs were then compared to the kinetics of the optimized reference Fab (MAB1opFab) using the ForteBio Octet system (numerical data summarized in Table 3).

TABLE 3

Affinity of Fabs for human GITR

| Fab | KD [M] |
|---|---|
| MAB1opFab(a)* | 1.25E-8 |
| MAB2(a) | 6.84E-9 |
| MAB3(a) | 2.98E-9 |
| MAB1opFab(b)* | 6.59E-9 |
| MAB4(b) | 2.43E-9 |
| MAB5(b) | 3.74E-9 |
| MAB1opFab(c)* | 1.47E-8 |
| MAB6(c) | 5.94E-9 |

*a, b, c indicate three separate Forte experiments. The results are global fitting of two sample duplicates.
Amino acid sequence of antibodies MAB2, MAB3, MAB4, MAB5, MAB6, and percentage identity to human germline sequence The variable region amino acid sequences of the five Fabs (MAB2, MAB3, MAB4, MAB5, MAB6,) are shown in Table 1. The percent identity to human germline sequences of the five Fabs was determined by aligning the Vh and Vk amino acid sequences against a single germline sequence (VKIII L16/A27 and VH3 3-30, respectively; Table 4). Residues in CDRH3 and CDRL3 were omitted from the calculation for each chain.

TABLE 4

Percent identity of the five Fabs to human germline sequences

| Fab | VKIII L15/A27 | VH3 3-30 | Fv |
|---|---|---|---|
| MAB2 | 95% | 86% | 90% |
| MAB3 | 98% | 85% | 91% |
| MAB4 | 95% | 85% | 89% |
| MAB5 | 95% | 83% | 89% |
| MAB6 | 95% | 82% | 88% |
| MAB7 | 95% | 85% | 89% |
| MAB8 | 95% | 85% | 89% |

Conservation of Human GITR Antigenic Epitope

Antigen epitope conservation was evaluated by an indirect Competition ELISA. All five Fabs blocked the parental mouse antibody MAB1 binding to human GITR indicating that these human Fabs retain the epitope specificity of the original murine antibody.

Analysis of Antigen Specificity of MAB4 and MAB5 by ELISA

In order to test whether antigen specificity of the parental mouse antibody MAB1 was retained in the IgGs, MAB2, MAB3, MAB4 and MAB5, binding of the antibodies to a panel of human TNFRs was tested in an ELISA assay, The results of one such assay with MAB4 and MAB5 (FIG. 2C) show that MAB4 and MAB5 retain high specificity for GITR, similar to the murine antibody MAB1. Similar results were obtained with MAB2, MAB3 and MAB6.

Figure 2A:
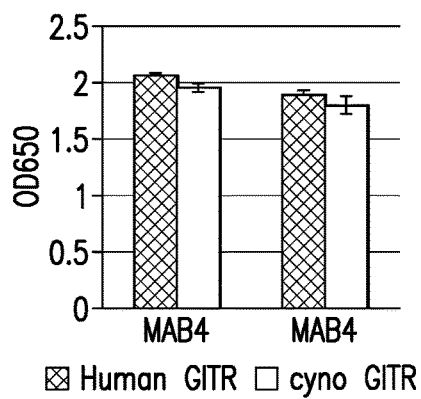
FIG. 2A-2E depicts results of binding experiments of anti-GITR MAB antibodies.
Figure 2B:
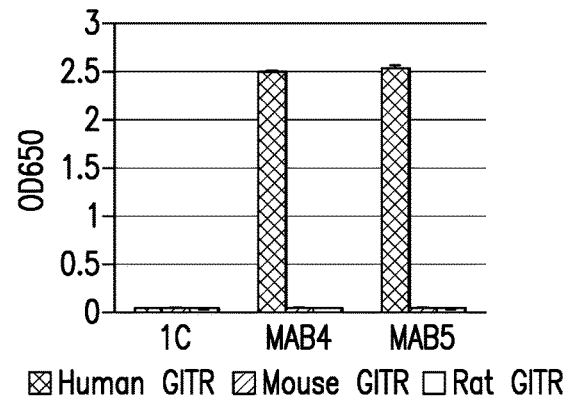
Figure 2C:
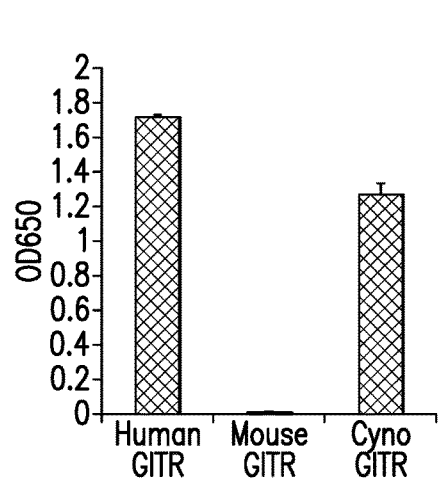

Antibody Binding to Human and Cynomolgus Macaque but not Rodent GITR Protein in ELISA The parental mouse antibody MAB1 binds to human and cynomolgus but not rodent GITR protein. FIG. 2A-B shows that, like MAB1, antibodies MAB4 and MAB5 were able to bind in a similar manner both human and cynomolgus GITR, but not rodent GITR. Similar results were found with MAB6, 7, and 8.

Binding affinities of GITR agonist antibodies MAB4 and MAB5 for human (hGITR) and cyno (cGITR) GITR, were determined by Biacore analysis. See Table 5. Monoclonal antibodies MAB4 and MAB5 bind to human GITR with subnanomolar binding affinities (KD). Antibodies MAB4 and MAB5 bind to cyno GITR with nanomolar binding affinities that are about 2-3 fold lower than the binding affinities for human GITR. The anti-GITR agonist antibodies of the invention bind selectively to human and cyno GITR in a number of biochemical assays, including flow cytometry, ELISA, Biacore, and ProtagenTM chip assays.

TABLE 5

Binding affinities of MAbs to human- and cyno-GITR

| Antigen | mAb | KD (nM) |
| --- | --- | --- |
| hGITR | MAB4 | 0.684 (±0.331) |
| hGITR | MAB5 | 0.973 (±0.167) |
| hGITR | MAB7 | 4.29 (±0.14) |
| cGITR | MAB4 | 1.78 (±0.543) |
| cGITR | MAB5 | 1.87 (±0.520) |
| cGITR | MAB7 | 3.67 (±0.09) |

Monoclonal antibody MAB7 binds to human as well as cyno CD4+ Tcells. FACS analysis of isolated cyno or human PBMCs demonstrated MAB7 binds isolated CD4++Tcells. Additionally, FACS experiments demonstrated GITR (by binding of MAB7) and CD25 upregulation following CD3/CD28 activation of PBMCs (CD4+ Tcells). (data not shown)

Functional Activity of Antibodies and in Reporter Gene Assays and Cell Assays

Antibodies were assayed in a reporter gene assay for functional activity (FIG. 3). Each of MAB4, MAB5, MAB7 and MAB8 IgGs induce NFκB activity when crosslinked, at levels similar to GITR ligand (GITR-L). See FIG. 3A-D. Similar results were obtained with MAB2, MAB3, and MAB6 (data not shown).

Figure 2D:
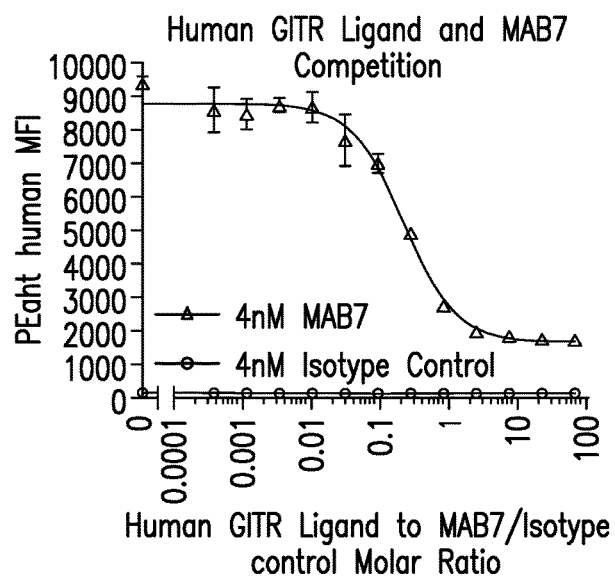
Figure 2E:
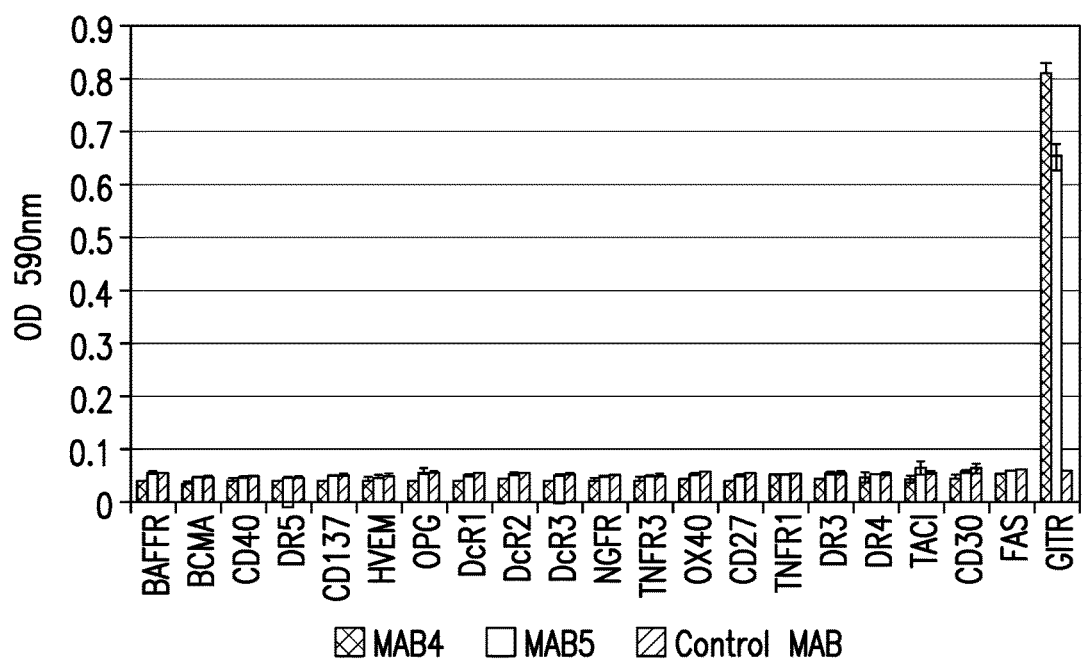
Figure 3B:
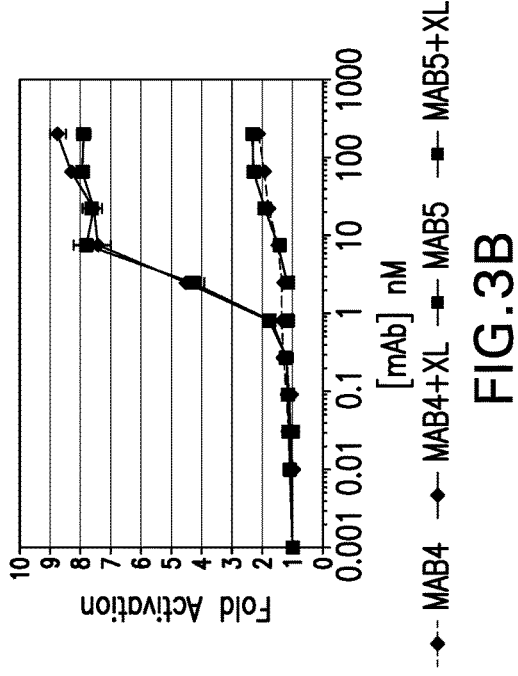
FIG. 3A-3D depict intracellular signaling in 293 cells that have been engineered to express GITR.
Figure 3D:
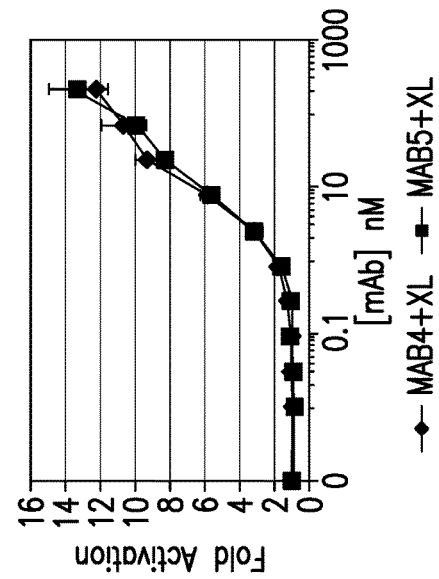
Figure 3A:
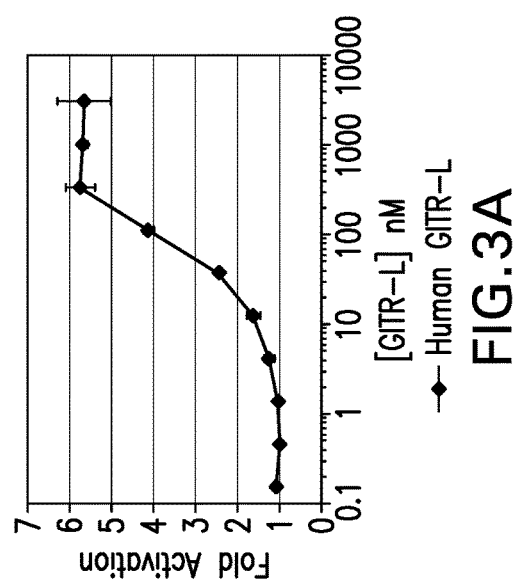
Figure 3C:
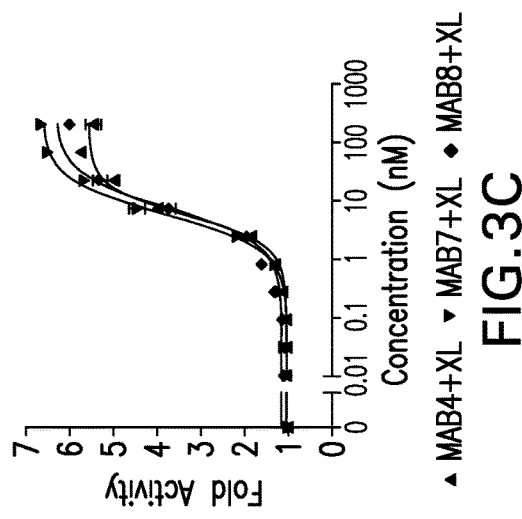

MAB7 competes with human GITR ligand for binding human GITR expressing stable cell line. Competition assays were performed in triplicate sets of values, FACS competition analysis demonstrates inhibition of ligand binding. See FIG. 2D.

Figure 4A:
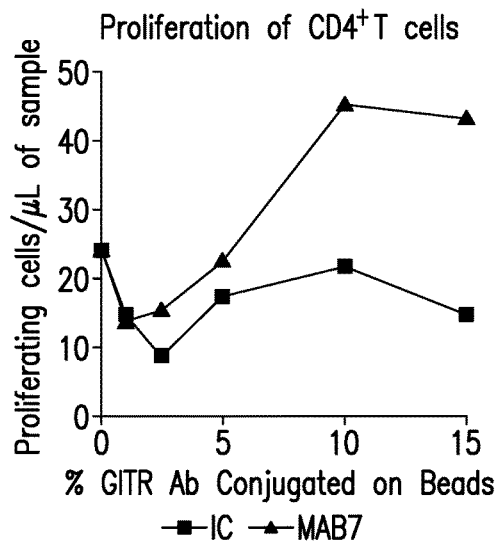
FIG. 4A-4C depicts in vitro co-stimulatory activity of MAB7 on T cells is dependent upon T cell activation. Anti-CD3 (OKT3), anti-CD28 (CD28.2) and anti-GITR mAbs were cross-linked (at a ratio of 1:1:3) on beads and then incubated with PBMCs.
Figure 4B:
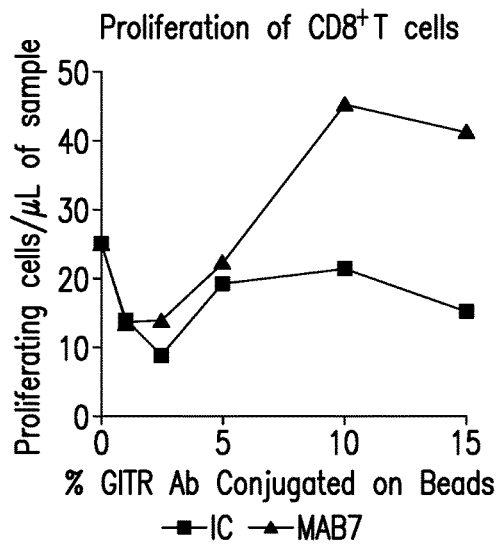
Figure 4C:
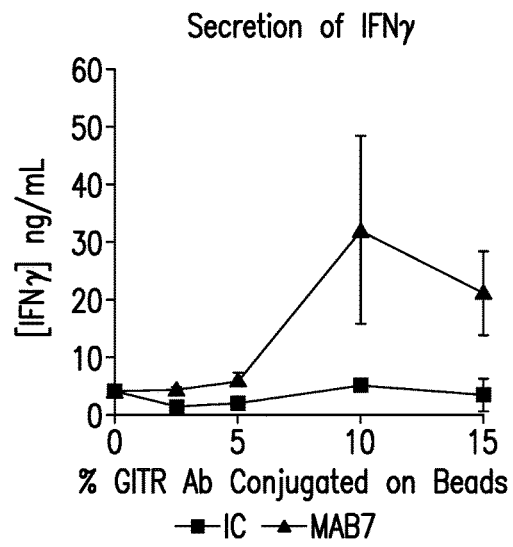

To confirm functional activity on endogenous GITR, antibodies were conjugated to beads and incubated with purified CFSE labelled human PBMCs. MAB7 induces an increase in proliferation of both CD4+ T cells (FIG. 4A) and CD8+ T cells (FIG. 4B) compared to an isotype control antibody. This increase in proliferation was also accompanied by an increase in the secretion of several cytokines, including IFNγ (FIG. 4C), TNFα, IL-10 and IL-13 (not shown). Similar results were found with MAB4, MAB5 (not shown). We were able to show that the increase in proliferation and IFNγ production induced by MAB7 was dependent upon the presence of anti-CD3 and anti-CD28 agonistic antibodies on the beads. If these co-stimulatory antibodies were omitted MAB had no agonist effects on either CD4+ or CD8+ T cells. Similar results were obtained with MAB2, MAB3, MAB4; MAB5 and MAB6.

Figure 6A:
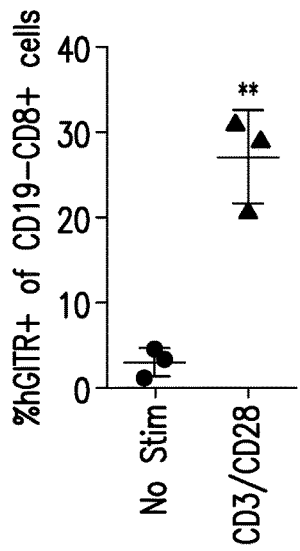
FIG. 6A-6D illustrates GITR is functional in hGITR-hGITRL knock-in mice. Splenocytes were isolated from hGITR-hGITRL knock-in mice and cultured either unstimulated or stimulated with aCD3 and aCD8 antibodies for 48 hours, then pulsed with controls or MAB7 at varying concentrations for 30 minutes, then fixed and stained with fluorophore-conjugated antibodies and analyzed by flow cytometry.
Figure 6B:
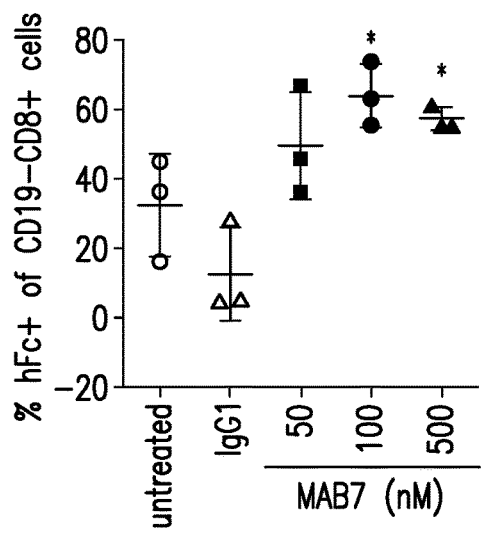
Figure 6C:
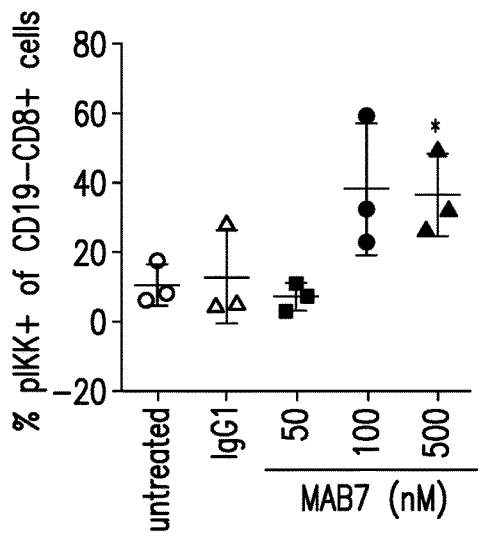
Figure 6D:
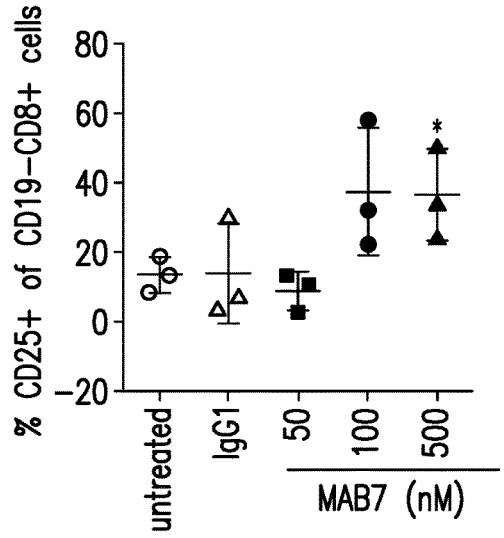

MAB7 was also found to demonstrate capability to induce FcgRIIIa signaling (shown to be correlated with ADCC activity) in an in vitro assay when high levels of GITR are present. Daudi-hGITR cells incubated with MAB7 or control Ab, and the Jurkat-V158 cell line showed MAB7 is able to induce FcgRIIIa signaling in an in vitro assay and that the ability of MAB7 to induce FcgRIIIa signaling correlates with the receptor level expressed on the surface of the Daudi cells (i.e. higher receptor levels equals greater FcgRIIIa signaling induction). See FIG. 5.

hGITR is expressed on T-cells and is functional in hGITR-hGITRL knock-in mice. Splenocytes were isolated from wild type or hGITR-hGITRL knock-in mice and cultured either without stimulation or with stimulation using a-CD3 and a-CD28 antibodies for 24, 48, 72 or 96 hours. Cells were then stained with fluorophore-conjugated antibodies and analyzed by flow cytometry, demonstrating human GITR is expressed, and costimulation results in increased GITR expression profile in wild type or transgenic mice. Splenocytes isolated from hGITR-hGITRL knock-in mice demonstrate induction of GITR expression in response to costimulation in culture (FIG. 6A). MAB7 effectively binds hGITR expressed on CD8+ cells (FIG. 6B); and MAB7 binding to stimulated Tcells correlates with increased Tcell activation as measured by pIKK staining (FIG. 6C) and T cell activation marker CD25+ (FIG. 6D).

MAB7 is functional in vivo. hGITR-hGITRL double knock-in mice with established Colon26 tumors were treated with a single dose of vehicle (n=8/timepoint) or MAB7 (n=10/timepoint) antibody as described above. Tumors were measured twice per week and tumor volume calculated using the equation $(L \times W^2)/2$. MAB treated animals demonstrated delayed growth of Colon26 tumors. At three days post treatment, whole blood (FIG. 7B-7C) and tumors (FIG. 7D-7E) were collected and analyzed by flow cytometry for cell surface hGITR expression on immune cells. Results suggest hGITR occupancy and shedding resulting in decreased hGITR from treated groups for both Tregulatory cells and Thelper cells in both blood and tumors (*p<0.05, ****p<0.00005).

Figure 8A:
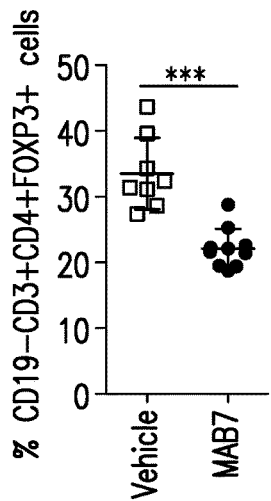
FIG. 8A-8E illustrates MAB7 elicits an anti-tumor immune response to Colon26 tumors in vivo. hGITR-hGITRL double knock-in mice with established Colon26 tumors were treated with a single dose of vehicle (n=8/timepoint) or MAB7 (n=10/timepoint).
Figure 8B:
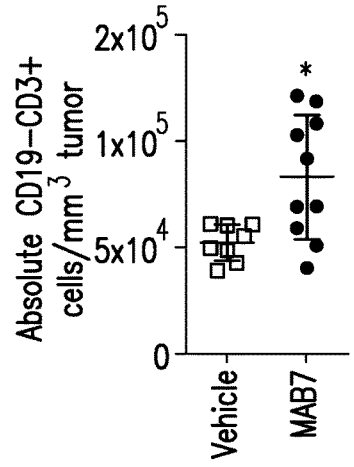
Figure 8C:
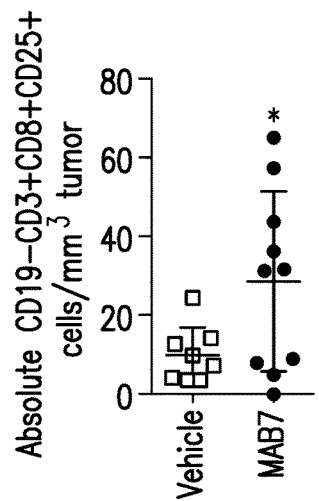
Figure 8D:
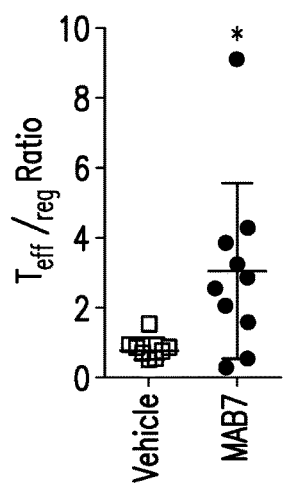
Figure 8E:
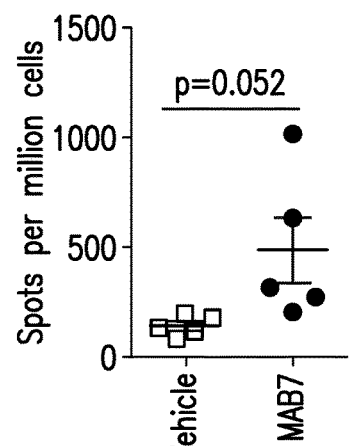

MAB7 elicits an anti-tumor immune response to Colon26 tumors in vivo. hGITR-hGITRL double knock-in mice with established Colon26 tumors were treated with a single dose of vehicle (n=8/timepoint) or MAB7 (n=10/timepoint). FIG. 8A depicts results 3-days post-dose, demonstrating Tregs are reduced in treated animals. FIG. 8B-8C depict results 15-days post-dose, demonstrating increased lymphocytes (8B) and increased activated CD8+ T cells (8C) present in tumor site following treatment. The absolute number of cells was normalized to tumor size to account for the significant difference in tumor size between Vehicle and MAB7 treated groups. MAB7 results suggest treatment results in increased Teff/Treg ratio in treated animals as determined by total intratumoral activated CD8+ T cells compared to CD4+ FOXP3+ Tregs. See FIG. 8D. Additionally, results of splenocyte assays from purified CD8+ T cells incubated with Colon26 tumor cells ex-vivo, and measuring CTL response using IFNg ELISPOT assay suggest increased tumor specific IFNg response in CD8+ T cells from MAB7 treated animals. (*p<0.05, ***p<0.0005). See FIG. 8E.

Figure 9A:
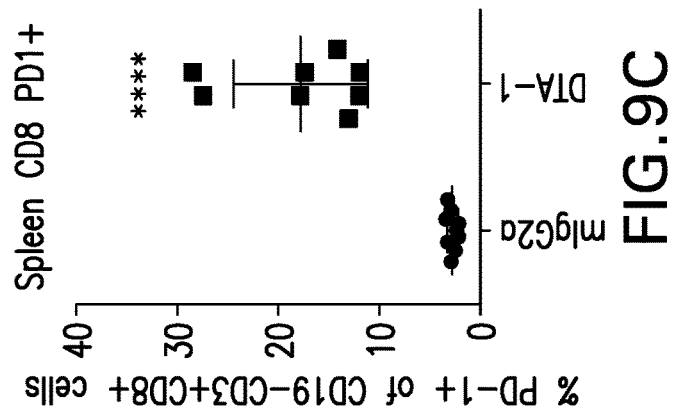
FIG. 9A-9C illustrates PD-1 expression is upregulated on CD8+ T cells in Colon26 tumors as well as spleens after treatment with a murine surrogate GITR antibody, DTA-1. Single cell suspensions of whole tumors or whole spleens were profiled by flow cytometry following 2 doses of DTA-1.
Figure 9B:
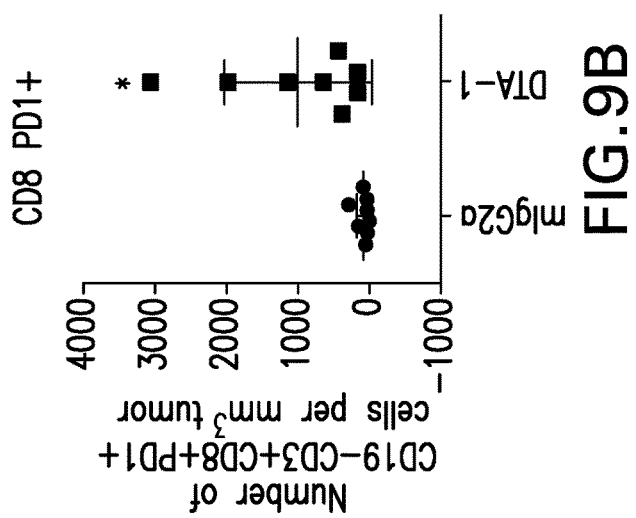
Figure 9C:
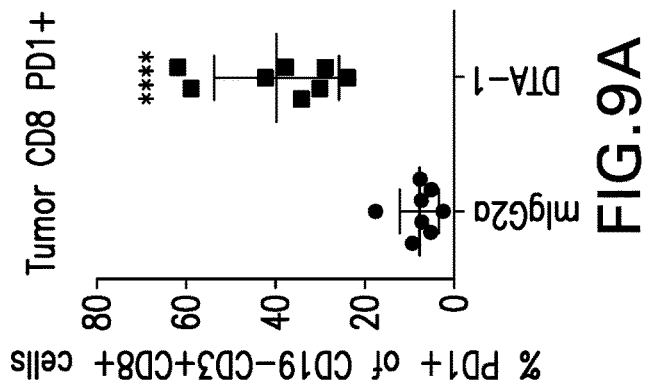

Treatment of mice with anti-mGITR Ab upregulates PD-1 expression in tumors and spleen. Mice with established Colon26 tumors were treated with two doses of control or murine anti mGITR antibody. FIG. 9A-9C depicts results demonstrating PD-1 expression is upregulated on CD8+ T cells in Colon26 tumors as well as spleens after treatment with surrogate GITR antibody, IgG2a-DTA-1.

Figure 10:
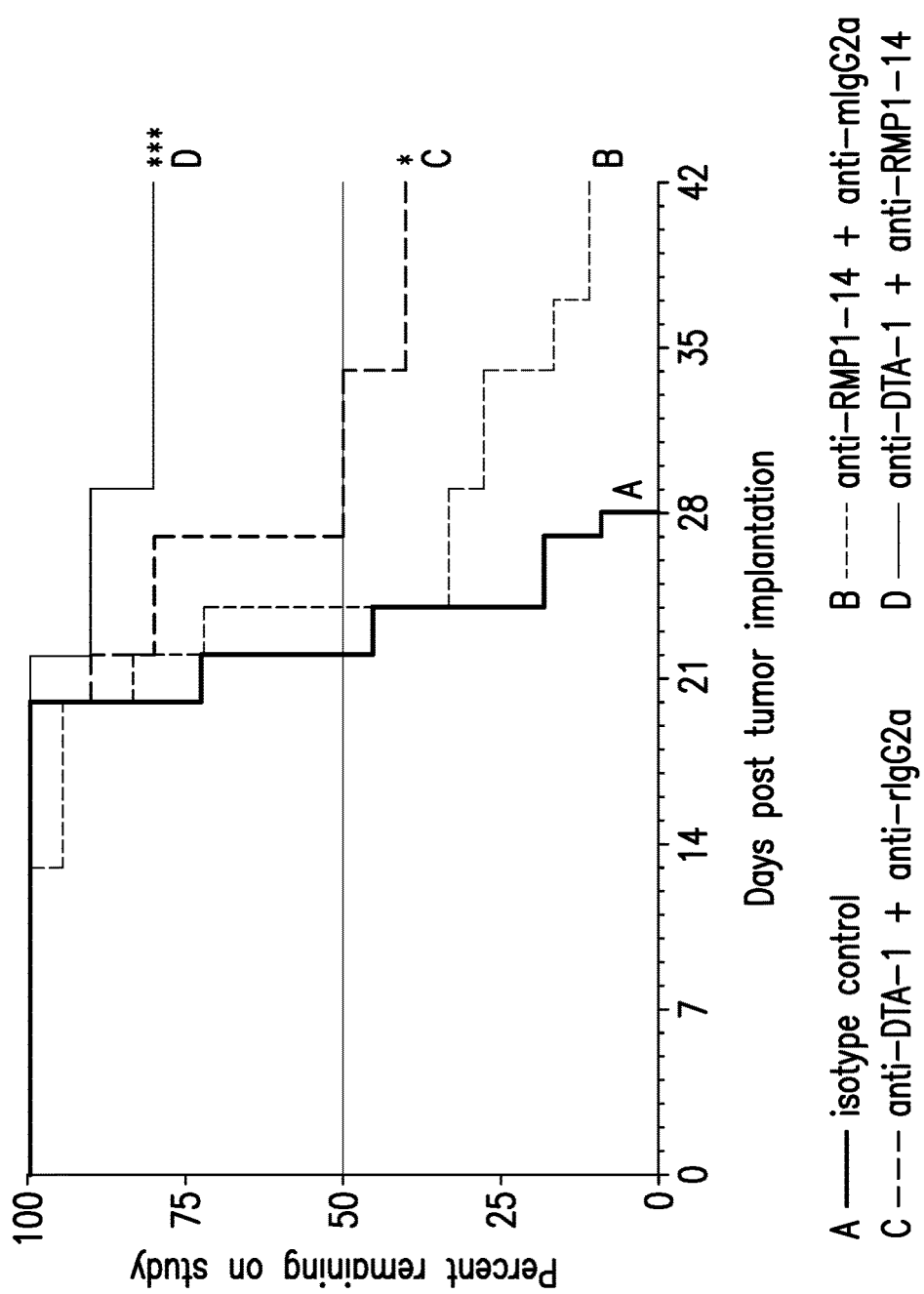
FIG. 10 illustrates anti-GITR and anti-PD-1 combinations confer survival advantage compared to isotype control. Depicted are results in Colon26 mice models treated with anti-GITR (IgG2a-DTA-1) and anti-PD-1 (RMP1-14) individually or in combination as compared to isotype control.

GITR and PD-1 combinations confer survival advantage compared to isotype control. Anti-GITR (DTA-1) and anti-PD-1 (RMP1-14) were administered alone and in combination in mice with established Colon26 tumors. See FIG. 10. Combination administration shows significant survival advantage compared to isotype control (***p<0.0005 pairwise comparison using the Gehan-Breslow-Wilcoxon test). Anti-mGITR (IgG2a-DTA-1) single agent shows significant survival advantage compared to isotype control (*p<0.05 pairwise comparison using the Gehan-Breslow-Wilcoxon test). The data indicate that the combination of IgG2a-DTA-1 and RMP1-14 confers a statistically significant survival advantage relative to isotype control treatment with a median TTE greater than 42 days (median TTE not achieved) (P<0.0005) relative to 22 days for the isotype treated group. Notably, 3/10 animals achieved a complete regression (CR), 2/10 animals achieved stable disease (SD). IgG2a-DTA-1 monotherapy resulted in a median TTE of 30.5 days (P<0.05), with 3/10 animals achieving stable disease (SD). The median survival of the RMP1-14 treated group was 24 days, which was not statistically significantly different from the isotype treated group. Kaplan Meier Graphs were generated and statistics performed using Prism software (GraphPad Software). Group comparisons were carried out as pairwise comparison using the Gehan-Breslow-Wilcoxon test. For all statistical evaluations the level of significance was set at p<0.05. Significance compared to the vehicle control group is reported. Stable disease is defined as 3 successive tumor volume measurements with 10% or less change in tumor volume.

TABLE 6

Combination Therapy

| Group | Ab1 (5 mg/kg, SC) | Ab2 | n/group |
|---|---|---|---|
| 1 | mIgG2a | rIgG2a (10 mg/kg, IP) | n = 10 |
| 2 | RMP1-14 (10 mg/kg, IP) mIgG2a | mIgG2a (5 mg/kg, SC) | n = 16 |
| 3 | DTA-1 | rIgG2a (10 mg/kg, IP) | n = 10 |
| 4 | DTA-1 | RMP1-14 (10 mg/kg, IP) | n = 10 |

IP = intraperitoneal;
SC = subcutaneous

Figure 11:
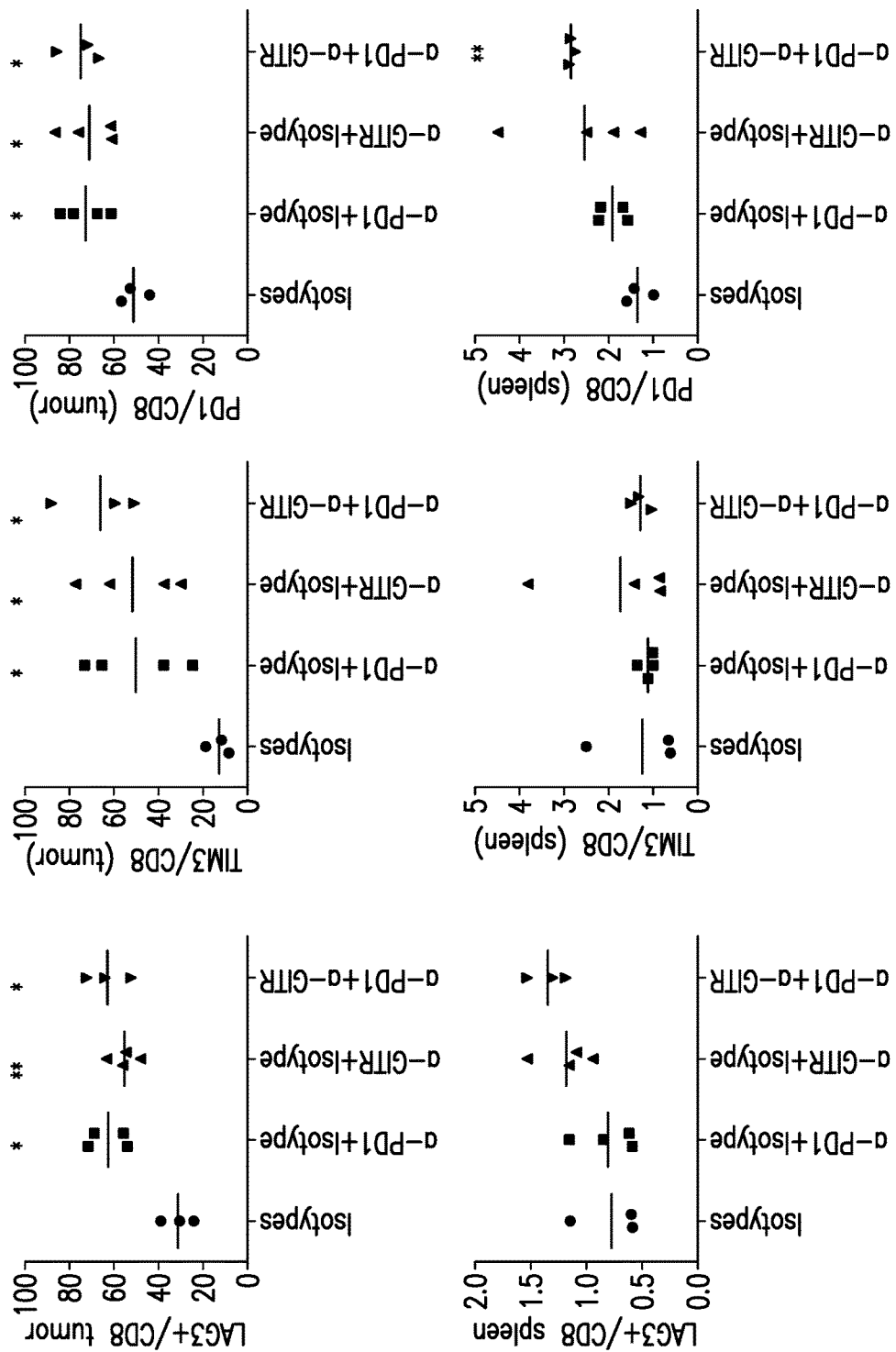
FIG. 11 illustrates expression of LAG3(first column), TIM3(middle column), and PD1(right column) after treatment with anti-GITR, anti-PD-1 and anti-GITR/anti-PD-1 in combinations in mice with established Colon26 tumors as compared to treatment with isotype control Ab. Depicted are results in Colon26 mice models treated with anti-GITR (IgG2a-DTA-1) and anti-PD-1 (RMP1-14) individually or in combination as compared to isotype control. The top row demonstrates results in tumor samples, and the lower row depicts results in spleen samples. LAG3, TIM3 and PD1 expression is upregulated on CD8+ T cells in Colon26 tumors after treatment with a-GITR, and a-PD1 PD-1 expression is upregulated on CD8+ T cells in Colon26 tumors after treatment with anti-GITR/anti-PD-1 in combination.

Expression of costimulatory molecules was assessed in tumors following administration of anti-GITR or anti-GITR in combination with anti-PD-1. See FIG. 11. Results of single cell suspensions of whole tumors and spleens profiled by flow cytometry following 1 dose of anti-GITR or anti-PD1 or anti-GITR+PD1 in combination demonstrated increased expression of LAG3, TIM3 and PD-1 on CD8+T cells in Colon26 tumors after treatment with GITR, PD-1 and in combination. A single combination dose demonstrated upregulated expression of PD-1 in spleen CD8+ cells.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. An anti-GITR agonist antibody or antibody fragment thereof comprising:
   a heavy chain variable region (VH) comprising:
   a VHCDR1 of SEQ ID NO:22,
   a VHCDR2 of SEQ ID NO:25, and
   a VHCDR3 of SEQ ID NO:29; and
   a light chain variable region (VL) comprising:
   a VLCDR1 of SEQ ID NO:30,
   a VLCDR2 of SEQ ID NO:33, and
   a VLCDR3 of SEQ ID NO:34.

2. The antibody or antibody fragment of claim 1, wherein the heavy chain framework region 4(FR4) of the antibody or antibody fragment is a human germline FR4.

3. The antibody or antibody fragment of claim 2, wherein the amino acid sequence of the heavy chain FR4 is SEQ ID NO:42.

4. The antibody or antibody fragment of claim 1, wherein the light chain FR4 of the antibody or antibody fragment is a human germline FR4.

5. The antibody or antibody fragment of claim 4, wherein the amino acid sequence of the light chain FR4 is SEQ ID NO:50.

6. The antibody or antibody fragment of claim 1, wherein the antibody or antibody fragment comprises a VH comprising an amino acid sequence that has at least 90% identity to SEQ ID NO: 99.

7. The antibody or antibody fragment of claim 1, wherein the antibody or antibody fragment comprises a VH comprising the amino acid sequence of SEQ ID NO: 99.

8. The antibody or antibody fragment of claim 1, wherein the antibody or antibody fragment comprises a VL comprising an amino acid sequence that has at least 90% identity to SEQ ID NO: 7.

9. The antibody or antibody fragment of claim 1, wherein the antibody or antibody fragment comprises a VL comprising the amino acid sequence of SEQ ID NO: 7.

10. The antibody or antibody fragment of claim 1, which comprises a VH comprising SEQ ID NO: 99, and a VL comprising SEQ ID NO:7.

11. The antibody or antibody fragment of claim 1, wherein the antibody comprises a heavy chain comprising the amino acid sequence of SEQ ID NO:100; and a light chain comprising the amino acid sequence of SEQ ID NO:66.

12. The antibody or antibody fragment of claim 1, wherein the antibody or antibody fragment is humanized.

13. The antibody or antibody fragment of claim 1, wherein the antibody fragment is a Fab, Fab', F(ab')2, Fd, Fv, or a single chain Fv fragment (scFv).

14. The antibody or antibody fragment of claim 1, wherein the antibody or antibody fragment comprises a heavy chain constant region of human IgG1, and a light chain constant region of human kappa chain.

15. The antibody or antibody fragment of claim 1, wherein the antibody or antibody fragment is cross-linked to a second anti-GITR antibody or antibody fragment.

16. The antibody or antibody fragment of claim 1, wherein the antibody or antibody fragment is glycosylated.

17. The antibody or antibody fragment of claim 1, wherein the antibody or antibody fragment induces an elevated Teff: Treg ratio in vivo.

18. The antibody or antibody fragment of claim 1, wherein the antibody or antibody fragment induces a potentiated immune response in vivo.

19. The antibody or antibody fragment of claim 1, wherein the antibody or antibody fragment binds to human and non-human primate GITR.

20. A pharmaceutical composition comprising the antibody or antibody fragment of claim 1 and a pharmaceutically acceptable carrier.

21. The pharmaceutical composition of claim 20 further comprising an antibody against CTLA4, LAG3, TIM3, PD-1, or PD-L1.

22. A kit comprising the antibody or antibody fragment of claim 1 and a second agent.

23. The antibody of claim 1, wherein the antibody comprises an IgG isotype antibody Fc region.

* * * * *

SEQUENCE LISTING

<160> NUMBER OF SEQ ID NOS: 113

<210> SEQ ID NO 1
<211> LENGTH: 241
<212> TYPE: PRT
<213> ORGANISM: Homo sapiens

<400> SEQUENCE: 1

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

```
Glu Pro Leu Gly Trp Leu Thr Val Val Leu Ala Val Ala Ala Cys
            165                 170                 175

Val Leu Leu Leu Thr Ser Ala Gln Leu Gly Leu His Ile Trp Gln Leu
        180                 185                 190

Arg Ser Gln Cys Met Trp Pro Arg Glu Thr Gln Leu Leu Leu Glu Val
            195                 200                 205

Pro Pro Ser Thr Glu Asp Ala Arg Ser Cys Gln Phe Pro Glu Glu Glu
210                 215                 220

Arg Gly Glu Arg Ser Ala Glu Glu Lys Gly Arg Leu Gly Asp Leu Trp
225                 230                 235                 240

Val

<210> SEQ ID NO 2
<211> LENGTH: 255
<212> TYPE: PRT
<213> ORGANISM: Homo sapiens

<400> SEQUENCE: 2

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Cys Trp Arg Cys Arg Arg Arg Pro Lys Thr
130                 135                 140

Pro Glu Ala Ala Ser Ser Pro Arg Lys Ser Gly Ala Ser Asp Arg Gln
145                 150                 155                 160

Arg Arg Arg Gly Gly Trp Glu Thr Cys Gly Cys Glu Pro Gly Arg Pro
                165                 170                 175

Pro Gly Pro Pro Thr Ala Ala Ser Ser Pro Gly Ala Pro Gln Ala
            180                 185                 190

Ala Gly Ala Leu Arg Ser Ala Leu Gly Arg Ala Leu Leu Pro Trp Gln
        195                 200                 205

Gln Lys Trp Val Gln Glu Gly Gly Ser Asp Gln Arg Pro Gly Pro Cys
210                 215                 220

Ser Ser Ala Ala Ala Ala Gly Pro Cys Arg Arg Glu Arg Glu Thr Gln
225                 230                 235                 240

Ser Trp Pro Pro Ser Ser Leu Ala Gly Pro Asp Gly Val Gly Ser
                245                 250                 255

<210> SEQ ID NO 3
<211> LENGTH: 234
<212> TYPE: PRT
<213> ORGANISM: Homo sapiens
```

-continued

```
<400> SEQUENCE: 3

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Lys Thr Gln Leu Leu Leu Glu Val Pro Pro Ser Thr Glu Asp Ala
        195                 200                 205

Arg Ser Cys Gln Phe Pro Glu Glu Glu Arg Gly Glu Arg Ser Ala Glu
    210                 215                 220

Glu Lys Gly Arg Leu Gly Asp Leu Trp Val
225                 230

<210> SEQ ID NO 4
<211> LENGTH: 39
<212> TYPE: PRT
<213> ORGANISM: Artificial Sequence
<220> FEATURE:
<223> OTHER INFORMATION: synthetic sequence

<400> SEQUENCE: 4

Cys Gly Pro Gly Arg Leu Leu Leu Gly Thr Gly Thr Asp Ala Arg Cys
1               5                   10                  15

Cys Arg Val His Thr Thr Arg Cys Cys Arg Asp Tyr Pro Gly Glu Glu
            20                  25                  30

Cys Cys Ser Glu Trp Asp Cys
        35

<210> SEQ ID NO 5
<211> LENGTH: 40
<212> TYPE: PRT
<213> ORGANISM: Artificial Sequence
<220> FEATURE:
<223> OTHER INFORMATION: synthetic sequence

<400> SEQUENCE: 5

Met Cys Val Gln Pro Glu Phe His Cys Gly Asp Pro Cys Cys Thr Thr
1               5                   10                  15
```

Cys Arg His His Pro Cys Pro Pro Gly Gln Gly Val Gln Ser Gly
                20                  25                  30

Lys Phe Ser Phe Gly Phe Gln Cys
            35                  40

<210> SEQ ID NO 6
<211> LENGTH: 121
<212> TYPE: PRT
<213> ORGANISM: Artificial Sequence
<220> FEATURE:
<223> OTHER INFORMATION: synthetic sequence

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
                20                  25                  30

Gly Val Asp Trp Val Arg Gln Ala Pro Gly Lys Gly Leu Glu Trp Val
            35                  40                  45

Gly Val Ile Trp Gly Gly Gly Thr Tyr Tyr Ala Ser Ser Val Met
    50                  55                  60

Ala Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Ala Tyr Gly His Asp Gly Gly Phe Ala Met Asp Tyr Trp Gly
            100                 105                 110

Gln Gly Thr Leu Val Thr Val Ser Ser
        115                 120

<210> SEQ ID NO 7
<211> LENGTH: 107
<212> TYPE: PRT
<213> ORGANISM: Artificial Sequence
<220> FEATURE:
<223> OTHER INFORMATION: synthetic sequence

<400> SEQUENCE: 7

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Val Ser Ser Asn
                20                  25                  30

Val Ala Trp Tyr Gln Gln Arg Pro Gly Gln Ala Pro Arg Leu Leu Ile
            35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Ser Tyr Ser Tyr Pro Phe
                85                  90                  95

Thr Phe Gly Gln Gly Thr Lys Leu Glu Ile Lys
            100                 105

<210> SEQ ID NO 8
<211> LENGTH: 121
<212> TYPE: PRT
<213> ORGANISM: Artificial Sequence
<220> FEATURE:
<223> OTHER INFORMATION: synthetic sequence

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Leu
        35                  40                  45

Gly Val Ile Trp Gly Gly Gly Thr Tyr Tyr Thr Ala Ser Leu Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Ala Tyr Gly His Asp Gly Phe Ala Met Asp Tyr Trp Gly
            100                 105                 110

Gln Gly Thr Leu Val Thr Val Ser Ser
            115                 120

<210> SEQ ID NO 9
<211> LENGTH: 107
<212> TYPE: PRT
<213> ORGANISM: Artificial Sequence
<220> FEATURE:
<223> OTHER INFORMATION: synthetic sequence

<400> SEQUENCE: 9

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Tyr Ser Tyr Pro Phe
                85                  90                  95

Thr Phe Gly Gln Gly Thr Lys Leu Glu Ile Lys
            100                 105

<210> SEQ ID NO 10
<211> LENGTH: 121
<212> TYPE: PRT
<213> ORGANISM: Artificial Sequence
<220> FEATURE:
<223> OTHER INFORMATION: synthetic sequence

<400> SEQUENCE: 10

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Val
        35                  40                  45

Gly Val Ile Trp Gly Gly Gly Thr Tyr Tyr Ala Ser Ser Leu Met
    50                  55                  60

```
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys His Ala Tyr Gly His Asp Gly Phe Ala Met Asp Tyr Trp Gly
            100                 105                 110

Gln Gly Thr Leu Val Thr Val Ser Ser
        115                 120

<210> SEQ ID NO 11
<211> LENGTH: 6
<212> TYPE: PRT
<213> ORGANISM: Artificial Sequence
<220> FEATURE:
<223> OTHER INFORMATION: synthetic sequence

<400> SEQUENCE: 11

His His His His His His
1               5

<210> SEQ ID NO 12
<211> LENGTH: 121
<212> TYPE: PRT
<213> ORGANISM: Artificial Sequence
<220> FEATURE:
<223> OTHER INFORMATION: synthetic sequence

<400> SEQUENCE: 12

Glu Val Gln Leu Val Glu Ser Gly Gly Leu Val Gln Ser Gly Gly
1               5                  10                  15

Ser Leu Arg Leu Ser Cys Ala Ala Ser Gly Phe Ser Leu Ser Ser Tyr
                 20                  25                  30

Gly Val Asp Trp Val Arg Gln Ala Pro Gly Lys Gly Leu Glu Trp Leu
            35                  40                  45

Gly Val Ile Trp Gly Gly Gly Thr Tyr Tyr Thr Ser Ser Leu Met
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys His Ala Tyr Gly His Asp Gly Phe Ala Met Asp Tyr Trp Gly
            100                 105                 110

Gln Gly Thr Leu Val Thr Val Ser Ser
        115                 120

<210> SEQ ID NO 13
<211> LENGTH: 11
<212> TYPE: PRT
<213> ORGANISM: Artificial Sequence
<220> FEATURE:
<223> OTHER INFORMATION: synthetic sequence

<400> SEQUENCE: 13

Ala Ala Gly Ala Ser His His His His His
1               5                   10

<210> SEQ ID NO 14
<211> LENGTH: 121
<212> TYPE: PRT
<213> ORGANISM: Artificial Sequence
<220> FEATURE:
<223> OTHER INFORMATION: synthetic sequence
```

<400> SEQUENCE: 14

```
Glu Val Gln Leu Val Glu Ser Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Leu
        35                  40                  45

Gly Val Ile Trp Gly Gly Gly Thr Tyr Tyr Thr Ser Ser Leu Met
    50                  55                  60

Ala Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Ala Tyr Gly His Asp Gly Gly Phe Ala Met Asp Tyr Trp Gly
            100                 105                 110

Gln Gly Thr Leu Val Thr Val Ser Ser
        115                 120
```

<210> SEQ ID NO 15
<211> LENGTH: 5
<212> TYPE: PRT
<213> ORGANISM: Artificial Sequence
<220> FEATURE:
<223> OTHER INFORMATION: synthetic sequence

<400> SEQUENCE: 15

```
Gly Gly Gly Gly Ser
1               5
```

<210> SEQ ID NO 16
<211> LENGTH: 121
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: (E/Q)
<220> FEATURE:
<221> NAME/KEY: VARIANT
<222> LOCATION: (14)..(14)
<223> OTHER INFORMATION: (P/S)
<220> FEATURE:
<221> NAME/KEY: VARIANT
<222> LOCATION: (48)..(48)
<223> OTHER INFORMATION: (L/V)
<220> FEATURE:
<221> NAME/KEY: VARIANT
<222> LOCATION: (60)..(60)
<223> OTHER INFORMATION: (A/T)
<220> FEATURE:
<221> NAME/KEY: VARIANT
<222> LOCATION: (61)..(61)
<223> OTHER INFORMATION: (A/S)
<220> FEATURE:
<221> NAME/KEY: VARIANT
<222> LOCATION: (63)..(63)
<223> OTHER INFORMATION: (L/V)
<220> FEATURE:
<221> NAME/KEY: VARIANT
<222> LOCATION: (65)..(65)
<223> OTHER INFORMATION: (A/G)
<220> FEATURE:
<221> NAME/KEY: VARIANT
<222> LOCATION: (97)..(97)
<223> OTHER INFORMATION: (K/R)

```
<220> FEATURE:
<221> NAME/KEY: VARIANT
<222> LOCATION: (98)..(98)
<223> OTHER INFORMATION: (H/N)

<400> SEQUENCE: 16

Xaa Val Gln Leu Val Glu Ser Gly Gly Gly Leu Val Gln Xaa Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Xaa
            35                  40                  45

Gly Val Ile Trp Gly Gly Gly Thr Tyr Tyr Xaa Xaa Ser Xaa Met
    50                  55                  60

Xaa Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Xaa Xaa Ala Tyr Gly His Asp Gly Gly Phe Ala Met Asp Tyr Trp Gly
            100                 105                 110

Gln Gly Thr Leu Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (27)..(27)
<223> OTHER INFORMATION: (E/Q)
<220> FEATURE:
<221> NAME/KEY: VARIANT
<222> LOCATION: (33)..(33)
<223> OTHER INFORMATION: (L/V)
<220> FEATURE:
<221> NAME/KEY: VARIANT
<222> LOCATION: (39)..(39)
<223> OTHER INFORMATION: (K/R)
<220> FEATURE:
<221> NAME/KEY: VARIANT
<222> LOCATION: (60)..(60)
<223> OTHER INFORMATION: (D/A)

<400> SEQUENCE: 17

Glu Ile Val Met Thr Gln Ser Pro Ala Thr Leu Ser Val Ser Pro Gly
1               5                   10                  15

Glu Arg Ala Thr Leu Ser Cys Arg Ala Ser Xaa Ser Val Ser Ser Asn
            20                  25                  30

Xaa Ala Trp Tyr Gln Gln Xaa Pro Gly Gln Ala Pro Arg Leu Leu Ile
            35                  40                  45

Tyr Gly Ala Ser Asn Arg Ala Thr Gly Ile Pro Xaa Arg Phe Ser Gly
            50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gly Gln Ser Tyr Ser Tyr Pro Phe
                85                  90                  95

Thr Phe Gly Gln Gly Thr Lys Leu Glu Ile Lys
            100                 105
```

```
<210> SEQ ID NO 18
<211> LENGTH: 15
<212> TYPE: PRT
<213> ORGANISM: Artificial Sequence
<220> FEATURE:
<223> OTHER INFORMATION: synthetic sequence

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 29
<212> TYPE: DNA
<213> ORGANISM: Artificial Sequence
<220> FEATURE:
<223> OTHER INFORMATION: synthetic sequence

<400> SEQUENCE: 19
gcgtctagaa ctggatggtg ggaagatgg                                      29

<210> SEQ ID NO 20
<211> LENGTH: 330
<212> TYPE: PRT
<213> ORGANISM: Artificial Sequence
<220> FEATURE:
<223> OTHER INFORMATION: synthetic sequence

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 21
<211> LENGTH: 107
<212> TYPE: PRT
<213> ORGANISM: Artificial Sequence
<220> FEATURE:
<223> OTHER INFORMATION: synthetic sequence

<400> SEQUENCE: 21

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 22
<211> LENGTH: 5
<212> TYPE: PRT
<213> ORGANISM: Artificial Sequence
<220> FEATURE:
<223> OTHER INFORMATION: synthetic sequence

<400> SEQUENCE: 22

Ser Tyr Gly Val Asp
1               5

<210> SEQ ID NO 23
<211> LENGTH: 16
<212> TYPE: PRT
<213> ORGANISM: Artificial Sequence
<220> FEATURE:
<223> OTHER INFORMATION: synthetic sequence

<400> SEQUENCE: 23

Val Ile Trp Gly Gly Gly Gly Thr Tyr Tyr Ala Ser Ser Val Met Ala
1               5                   10                  15

<210> SEQ ID NO 24
<211> LENGTH: 16
<212> TYPE: PRT
```

```
<213> ORGANISM: Artificial Sequence
<220> FEATURE:
<223> OTHER INFORMATION: synthetic sequence

<400> SEQUENCE: 24

Val Ile Trp Gly Gly Gly Gly Thr Tyr Tyr Thr Ala Ser Leu Met Gly
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: synthetic sequence

<400> SEQUENCE: 25

Val Ile Trp Gly Gly Gly Gly Thr Tyr Tyr Ala Ser Ser Leu Met Gly
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: synthetic sequence

<400> SEQUENCE: 26

Val Ile Trp Gly Gly Gly Gly Thr Tyr Tyr Thr Ser Ser Leu Met Gly
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: synthetic sequence

<400> SEQUENCE: 27

Val Ile Trp Gly Gly Gly Gly Thr Tyr Tyr Thr Ser Ser Leu Met Ala
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (11)..(11)
<223> OTHER INFORMATION: (A/T)
<220> FEATURE:
<221> NAME/KEY: VARIANT
<222> LOCATION: (12)..(12)
<223> OTHER INFORMATION: (A/S)
<220> FEATURE:
<221> NAME/KEY: VARIANT
<222> LOCATION: (14)..(14)
<223> OTHER INFORMATION: (L/V)
<220> FEATURE:
<221> NAME/KEY: VARIANT
<222> LOCATION: (16)..(16)
<223> OTHER INFORMATION: (A/G)

<400> SEQUENCE: 28

Val Ile Trp Gly Gly Gly Gly Thr Tyr Tyr Xaa Xaa Ser Xaa Met Xaa
1               5                   10                  15

<210> SEQ ID NO 29
```

```
<211> LENGTH: 13
<212> TYPE: PRT
<213> ORGANISM: Artificial Sequence
<220> FEATURE:
<223> OTHER INFORMATION: synthetic sequence

<400> SEQUENCE: 29

His Ala Tyr Gly His Asp Gly Gly Phe Ala Met Asp Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: synthetic sequence

<400> SEQUENCE: 30

Arg Ala Ser Glu Ser Val Ser Ser Asn Val Ala
1               5                   10

<210> SEQ ID NO 31
<211> LENGTH: 11
<212> TYPE: PRT
<213> ORGANISM: Artificial Sequence
<220> FEATURE:
<223> OTHER INFORMATION: synthetic sequence

<400> SEQUENCE: 31

Arg Ala Ser Gln Ser Val Ser Ser Asn Leu Ala
1               5                   10

<210> SEQ ID NO 32
<211> LENGTH: 11
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (4)..(4)
<223> OTHER INFORMATION: (E/Q)
<220> FEATURE:
<221> NAME/KEY: VARIANT
<222> LOCATION: (10)..(10)
<223> OTHER INFORMATION: (L/V)

<400> SEQUENCE: 32

Arg Ala Ser Xaa Ser Val Ser Ser Asn Xaa Ala
1               5                   10

<210> SEQ ID NO 33
<211> LENGTH: 7
<212> TYPE: PRT
<213> ORGANISM: Artificial Sequence
<220> FEATURE:
<223> OTHER INFORMATION: synthetic sequence

<400> SEQUENCE: 33

Gly Ala Ser Asn Arg Ala Thr
1               5

<210> SEQ ID NO 34
<211> LENGTH: 9
<212> TYPE: PRT
<213> ORGANISM: Artificial Sequence
<220> FEATURE:
<223> OTHER INFORMATION: synthetic sequence
```

```
<400> SEQUENCE: 34

Gly Gln Ser Tyr Ser Tyr Pro Phe Thr
1               5

<210> SEQ ID NO 35
<211> LENGTH: 30
<212> TYPE: PRT
<213> ORGANISM: Artificial Sequence
<220> FEATURE:
<223> OTHER INFORMATION: synthetic sequence

<400> SEQUENCE: 35

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: synthetic sequence

<400> SEQUENCE: 36

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: (E/Q)
<220> FEATURE:
<221> NAME/KEY: VARIANT
<222> LOCATION: (14)..(14)
<223> OTHER INFORMATION: (P/S)

<400> SEQUENCE: 37

Xaa Val Gln Leu Val Glu Ser Gly Gly Gly Leu Val Gln Xaa Gly Gly
1               5                   10                  15

Ser Leu Arg Leu Ser Cys Ala Ala Ser Gly Phe Ser Leu Ser
            20                  25                  30

<210> SEQ ID NO 38
<211> LENGTH: 14
<212> TYPE: PRT
<213> ORGANISM: Artificial Sequence
<220> FEATURE:
<223> OTHER INFORMATION: synthetic sequence

<400> SEQUENCE: 38

Trp Val Arg Gln Ala Pro Gly Lys Gly Leu Glu Trp Val Gly
1               5                   10

<210> SEQ ID NO 39
<211> LENGTH: 14
<212> TYPE: PRT
<213> ORGANISM: Artificial Sequence
```

```
<220> FEATURE:
<223> OTHER INFORMATION: synthetic sequence

<400> SEQUENCE: 39

Trp Val Arg Gln Ala Pro Gly Lys Gly Leu Glu Trp Leu Gly
1               5                   10

<210> SEQ ID NO 40
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (13)..(13)
<223> OTHER INFORMATION: (L/V)

<400> SEQUENCE: 40

Trp Val Arg Gln Ala Pro Gly Lys Gly Leu Glu Trp Xaa Gly
1               5                   10

<210> SEQ ID NO 41
<211> LENGTH: 32
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (32)..(32)
<223> OTHER INFORMATION: (K/R)

<400> SEQUENCE: 41

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Xaa
            20                  25                  30

<210> SEQ ID NO 42
<211> LENGTH: 11
<212> TYPE: PRT
<213> ORGANISM: Artificial Sequence
<220> FEATURE:
<223> OTHER INFORMATION: synthetic sequence

<400> SEQUENCE: 42

Trp Gly Gln Gly Thr Leu Val Thr Val Ser Ser
1               5                   10

<210> SEQ ID NO 43
<211> LENGTH: 23
<212> TYPE: PRT
<213> ORGANISM: Artificial Sequence
<220> FEATURE:
<223> OTHER INFORMATION: synthetic sequence

<400> SEQUENCE: 43

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 44
<211> LENGTH: 15
<212> TYPE: PRT
<213> ORGANISM: Artificial Sequence
```

```
<220> FEATURE:
<223> OTHER INFORMATION: synthetic sequence

<400> SEQUENCE: 44

Trp Tyr Gln Gln Arg Pro Gly Gln Ala Pro Arg Leu Leu Ile Tyr
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: synthetic sequence

<400> SEQUENCE: 45

Trp Tyr Gln Gln Lys Pro Gly Gln Ala Pro Arg Leu Leu Ile Tyr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (5)..(5)
<223> OTHER INFORMATION: (K/R)

<400> SEQUENCE: 46

Trp Tyr Gln Gln Xaa Pro Gly Gln Ala Pro Arg Leu Leu Ile Tyr
1               5                   10                  15

<210> SEQ ID NO 47
<211> LENGTH: 32
<212> TYPE: PRT
<213> ORGANISM: Artificial Sequence
<220> FEATURE:
<223> OTHER INFORMATION: synthetic sequence

<400> SEQUENCE: 47

Gly Ile Pro Ala Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: synthetic sequence

<400> SEQUENCE: 48

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
```

<222> LOCATION: (4)..(4)
<223> OTHER INFORMATION: (A/D)

<400> SEQUENCE: 49

Gly Ile Pro Xaa Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 50
<211> LENGTH: 10
<212> TYPE: PRT
<213> ORGANISM: Artificial Sequence
<220> FEATURE:
<223> OTHER INFORMATION: synthetic sequence

<400> SEQUENCE: 50

Phe Gly Gln Gly Thr Lys Leu Glu Ile Lys
1               5                   10

<210> SEQ ID NO 51
<211> LENGTH: 363
<212> TYPE: DNA
<213> ORGANISM: Artificial Sequence
<220> FEATURE:
<223> OTHER INFORMATION: synthetic sequence

<400> SEQUENCE: 51
caggtgcagc tggtggagtc tgggggaggc ttggtacagc ctgggggtc cctgagactc      60 tcctgtgcag cctctggatt ctccctcagc agctatggtg tggactgggt tcgccaggct    120
ccaggaaagg gtctggagtg ggtgggagtt atatgggtg gtggaggcac atattatgct    180
tcttctgtca tggccagatt caccatctcc agagacaatt ccaagaacac gctgtatctg    240
caaatgaaca gcctgagagc tgaggacacg gccgtgtatt actgcgccaa acatgcctat    300
ggccatgatg gcggctttgc tatggattat tggggccagg gtaccttgt gaccgtgagc    360 tca                                                                   363

<210> SEQ ID NO 52
<211> LENGTH: 321
<212> TYPE: DNA
<213> ORGANISM: Artificial Sequence
<220> FEATURE:
<223> OTHER INFORMATION: synthetic sequence

<400> SEQUENCE: 52
gaaatagtga tgacgcagtc tccagccacc ctgtctgttt ctccaggaga aagagccacc     60
ctctcctgca gggccagtga gagtgttagc agtaatgtag cctggtacca gcagagacct    120
ggccaggcac ccaggctcct catctacggg gcatccaacc gggccactgg catcccagcc    180
aggttcagtg gcagtgggtc tgggacagac ttcactctca ccatcagcag actggagcct    240
gaagattttg cagtgtacta ctgcggccag agctatagct atccatttac ctttggccag    300
ggcaccaagc ttgaaattaa g                                               321

<210> SEQ ID NO 53
<211> LENGTH: 363
<212> TYPE: DNA
<213> ORGANISM: Artificial Sequence
<220> FEATURE:
<223> OTHER INFORMATION: synthetic sequence

<400> SEQUENCE: 53

```
caggtgcagc tggtggagtc tgggggaggc ttggtacagc ctgggggtc cctgagactc      60 tcctgtgcag cctctggatt ctccctcagc agctatggtg tggactgggt tcgccaggct    120
ccaggaaagg gtctggagtg gctgggagtt atatggggtg gtggaggcac atattatact    180
gcttctctca tgggcagatt caccatctcc agagacaatt ccaagaacac gctgtatctg    240
caaatgaaca gcctgagagc tgaggacacg gccgtgtatt actgcgccaa acatgcctat    300
ggccatgatg gcggctttgc tatggattat tggggccagg gtaccttgt gaccgtgagc    360 tca                                                                  363
```

```
<210> SEQ ID NO 54
<211> LENGTH: 321
<212> TYPE: DNA
<213> ORGANISM: Artificial Sequence
<220> FEATURE:
<223> OTHER INFORMATION: synthetic sequence

<400> SEQUENCE: 54
gaaatagtga tgacgcagtc tccagccacc ctgtctgtgt ctccagggga aagagccacc     60
ctctcctgca gggccagtca gagtgttagc agcaacttag cctggtacca gcagaaacct   120
ggccaggctc ccaggctcct catctacggg gcatccaacc gggccactgg catcccagac   180
aggttcagtg gcagtgggtc tgggacagac ttcactctca ccatcagcag actggagcct   240
gaagattttg cagtttacta ctgcggccag agctatagct atccatttac ctttggccag   300
ggcaccaagc ttgaaattaa a                                              321
```

```
<210> SEQ ID NO 55
<211> LENGTH: 363
<212> TYPE: DNA
<213> ORGANISM: Artificial Sequence
<220> FEATURE:
<223> OTHER INFORMATION: synthetic sequence

<400> SEQUENCE: 55
gaggtgcagc tggtggagtc cgggggaggc ttagttcagt ctgggggtc cctgagactc     60 tcctgtgcag cctctggatt ctccctcagc agctatggtg tggactgggt tcgccaggct   120
ccaggaaagg gtctggagtg ggtgggagtt atatggggtg gtggaggcac atattatgct   180
tcttctctca tgggcagatt caccatctcc agagacaatt ccaagaacac gctgtatctg   240
caaatgaaca gcctgagagc tgaggacacg gccgtgtatt actgcgccaa acatgcctat   300
ggccatgatg gcggctttgc tatggattat tggggccagg gtaccttgt gaccgtgagc   360 tca                                                                  363
```

```
<210> SEQ ID NO 56
<211> LENGTH: 363
<212> TYPE: DNA
<213> ORGANISM: Artificial Sequence
<220> FEATURE:
<223> OTHER INFORMATION: synthetic sequence

<400> SEQUENCE: 56
gaggtgcagc tggtggagtc cgggggaggc ttagttcagt ctgggggtc cctgagactc     60 tcctgtgcag cctctggatt ctccctcagc agctatggtg tggactgggt tcgccaggct   120
ccaggaaagg gtctggagtg gctgggagtt atatggggtg gtggaggcac atattatact   180
tcttctctca tgggcagatt caccatctcc agagacaatt ccaagaacac gctgtatctg   240
```

-continued

```
caaatgaaca gcctgagagc tgaggacacg gccgtgtatt actgcgccaa acatgcctat      300
ggccatgatg gcggctttgc tatggattat tggggccagg gtaccttgt gaccgtgagc       360 tca                                                                    363
```

<210> SEQ ID NO 57
<211> LENGTH: 363
<212> TYPE: DNA
<213> ORGANISM: Artificial Sequence
<220> FEATURE:
<223> OTHER INFORMATION: synthetic sequence

<400> SEQUENCE: 57

```
gaggtgcagc tggtggagtc cggggggaggc ttagttcagt ctgggggtc cctgagactc      60 tcctgtgcag cctctggatt ctccctcagc agctatggtg tggactgggt tcgccaggct     120
ccaggaaagg gtctggagtg gctgggagtt atatggggtg gtggaggcac atattatact    180
tcttctctca tggccagatt caccatctcc agagacaatt ccaagaacac gctgtatctg    240
caaatgaaca gcctgagagc tgaggacacg gccgtgtatt actgcgccaa acatgcctat    300
ggccatgatg gcggctttgc tatggattat tggggccagg gtaccttgt gaccgtgagc     360 tca                                                                  363
```

<210> SEQ ID NO 58
<211> LENGTH: 321
<212> TYPE: DNA
<213> ORGANISM: Artificial Sequence
<220> FEATURE:
<223> OTHER INFORMATION: synthetic sequence

<400> SEQUENCE: 58

```
aacattgtaa tgacccaatc tcccaaatcc atgtccatgt cagtaggaga gagggtcacc     60
ttgagctgca aggccagtga aatgtggat acttttgtat cctggtatca acagaaacca     120
gaccactctc ctaaactact gatatacggg gcatccaacc ggtacactgg ggtccccgat    180
cgcttcacag gcagtggatc tgcaacagat ttcactctga ccatcagcag tgtgcaggct    240
gaagaccttg cagattatca ctgtggacag agttacagct atccattcac gttcggctcg   300
gggacaaagt tggaaataaa a                                              321
```

<210> SEQ ID NO 59
<211> LENGTH: 107
<212> TYPE: PRT
<213> ORGANISM: Artificial Sequence
<220> FEATURE:
<223> OTHER INFORMATION: synthetic sequence

<400> SEQUENCE: 59

```
Asn Ile Val Met Thr Gln Ser Pro Lys Ser Met Ser Met Ser Val Gly
 1               5                  10                  15

Glu Arg Val Thr Leu Ser Cys Lys Ala Ser Glu Asn Val Asp Thr Phe
            20                  25                  30

Val Ser Trp Tyr Gln Gln Lys Pro Asp His Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95
```

-continued

Thr Phe Gly Ser Gly Thr Lys Leu Glu Ile Lys
            100                 105

<210> SEQ ID NO 60
<211> LENGTH: 363
<212> TYPE: DNA
<213> ORGANISM: Artificial Sequence
<220> FEATURE:
<223> OTHER INFORMATION: synthetic sequence

<400> SEQUENCE: 60
caggtgcagc tgaaggagtc aggacctggc ctggtggcgc cctcacagag cctgtccatc    60
acttgcactg tctctgggtt ttcattaagg agctatggtg tagactgggt tcgccagcct   120
ccaggaaagg gtctggagtg gctgggagtt atatggggtg gtggaggcac aaattataat   180
tcagctctca tggccaaact gagtatcagc aaagacaagt ccaagagcca agttttctta   240
aaaatgaaca gtctgcaaac tgatgacaca gccatgtact actgtgccaa acatgcctat   300
ggtcacgacg gcggttttgc tatggactac tggggtcaag gaacctcagt caccgtctcc   360
tca                                                                  363

<210> SEQ ID NO 61
<211> LENGTH: 121
<212> TYPE: PRT
<213> ORGANISM: Artificial Sequence
<220> FEATURE:
<223> OTHER INFORMATION: synthetic sequence

<400> SEQUENCE: 61

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Arg Ser Tyr
            20                  25                  30

Gly Val Asp Trp Val Arg Gln Pro Pro Gly Lys Gly Leu Glu Trp Leu
        35                  40                  45

Gly Val Ile Trp Gly Gly Gly Thr Asn Tyr Asn Ser Ala Leu Met
    50                  55                  60

Ala Lys Leu Ser Ile Ser Lys Asp Lys Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys His Ala Tyr Gly His Asp Gly Gly Phe Ala Met Asp Tyr Trp Gly
            100                 105                 110

Gln Gly Thr Ser Val Thr Val Ser Ser
        115                 120

<210> SEQ ID NO 62
<211> LENGTH: 16
<212> TYPE: PRT
<213> ORGANISM: Artificial Sequence
<220> FEATURE:
<223> OTHER INFORMATION: synthetic sequence

<400> SEQUENCE: 62

Val Ile Trp Gly Gly Gly Gly Thr Asn Tyr Asn Ser Ala Leu Met Ala
1               5                   10                  15

<210> SEQ ID NO 63
<211> LENGTH: 11
<212> TYPE: PRT

```
<213> ORGANISM: Artificial Sequence
<220> FEATURE:
<223> OTHER INFORMATION: synthetic sequence

<400> SEQUENCE: 63

Lys Ala Ser Glu Asn Val Asp Thr Phe Val Ser
1               5                   10

<210> SEQ ID NO 64
<211> LENGTH: 7
<212> TYPE: PRT
<213> ORGANISM: Artificial Sequence
<220> FEATURE:
<223> OTHER INFORMATION: synthetic sequence

<400> SEQUENCE: 64

Gly Ala Ser Asn Arg Tyr Thr
1               5

<210> SEQ ID NO 65
<211> LENGTH: 451
<212> TYPE: PRT
<213> ORGANISM: Artificial Sequence
<220> FEATURE:
<223> OTHER INFORMATION: synthetic sequence

<400> SEQUENCE: 65
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Val
        35                  40                  45

Gly Val Ile Trp Gly Gly Gly Thr Tyr Tyr Ala Ser Ser Val Met
    50                  55                  60

Ala Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Ala Tyr Gly His Asp Gly Gly Phe Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

```
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 66
<211> LENGTH: 214
<212> TYPE: PRT
<213> ORGANISM: Artificial Sequence
<220> FEATURE:
<223> OTHER INFORMATION: synthetic sequence

<400> SEQUENCE: 66

Glu Ile Val Met Thr Gln Ser Pro Ala Thr Leu Ser Val Ser Pro Gly
1               5                   10                  15
Glu Arg Ala Thr Leu Ser Cys Arg Ala Ser Glu Ser Val Ser Ser Asn
            20                  25                  30
Val Ala Trp Tyr Gln Gln Arg Pro Gly Gln Ala Pro Arg Leu Leu Ile
        35                  40                  45
Tyr Gly Ala Ser Asn Arg Ala Thr Gly Ile Pro Ala Arg Phe Ser Gly
    50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys Gly Gln Ser Tyr Ser Tyr Pro Phe
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 67
<211> LENGTH: 1353
<212> TYPE: DNA
<213> ORGANISM: Artificial Sequence
<220> FEATURE:
<223> OTHER INFORMATION: synthetic sequence

<400> SEQUENCE: 67

| | | | | | |
|---|---|---|---|---|---|
| caggtgcagc | tggtggagtc | tgggggaggc | ttggtacagc | ctgggggtc | cctgagactc | 60 |
| tcctgtgcag | cctctggatt | ctccctcagc | agctatggtg | tggactgggt | tcgccaggct | 120 |
| ccaggaaagg | gtctggagtg | ggtgggagtt | atatggggtg | gtggaggcac | atattatgct | 180 |
| tcttctgtca | tggccagatt | caccatctcc | agagacaatt | ccaagaacac | gctgtatctg | 240 |
| caaatgaaca | gcctgagagc | tgaggacacg | gccgtgtatt | actgcgccaa | acatgcctat | 300 |
| ggccatgatg | gcggctttgc | tatggattat | tggggccagg | gtacccttgt | gaccgtgagc | 360 |
| tcagctagca | ccaagggccc | cagcgtgttc | cccctggccc | cagcagcaa | gagcaccagc | 420 |
| ggcggcacag | ccgccctggg | ctgcctggtg | aaggactact | tccccgagcc | cgtgaccgtg | 480 |
| tcctggaaca | gcggagccct | gacctccggc | gtgcacacct | tccccgccgt | gctgcagagc | 540 |
| agcggcctgt | acagcctgtc | cagcgtggtg | acagtgccca | gcagcagcct | gggcacccag | 600 |
| acctacatct | gcaacgtgaa | ccacaagccc | agcaacacca | aggtggacaa | gagagtggag | 660 |
| cccaagagct | gcgacaagac | ccacacctgc | cccccctgcc | cagccccaga | gctgctgggc | 720 |
| ggaccctccg | tgttcctgtt | cccccccaag | cccaaggaca | ccctgatgat | cagcaggacc | 780 |
| cccgaggtga | cctgcgtggt | ggtggacgtg | agccacgagg | acccagaggt | gaagttcaac | 840 |
| tggtacgtgg | acggcgtgga | ggtgcacaac | gccaagacca | agcccagaga | ggagcagtac | 900 |
| aacagcacct | acagggtggt | gtccgtgctg | accgtgctgc | accaggactg | gctgaacggc | 960 |
| aaggaataca | agtgcaaggt | ctccaacaag | gccctgccag | cccccatcga | aaagaccatc | 1020 |
| agcaaggcca | agggccagcc | acgggagccc | caggtgtaca | ccctgccccc | ctcccgggag | 1080 |
| gagatgacca | agaaccaggt | gtccctgacc | tgtctggtga | agggcttcta | ccccagcgac | 1140 |
| atcgccgtgg | agtgggagag | caacggccag | cccgagaaca | actacaagac | cacccccccca | 1200 |
| gtgctggaca | gcgacggcag | cttcttcctg | tacagcaagc | tgaccgtgga | caagtccagg | 1260 |
| tggcagcagg | gcaacgtgtt | cagctgcagc | gtgatgcacg | aggccctgca | caaccactac | 1320 |
| acccagaaga | gcctgagcct | gtcccccggc | aag | | | 1353 |

<210> SEQ ID NO 68
<211> LENGTH: 642
<212> TYPE: DNA
<213> ORGANISM: Artificial Sequence
<220> FEATURE:
<223> OTHER INFORMATION: synthetic sequence

<400> SEQUENCE: 68

-continued

```
gaaatagtga tgacgcagtc tccagccacc ctgtctgttt ctccaggaga aagagccacc        60
ctctcctgca gggccagtga gagtgttagc agtaatgtag cctggtacca gcagagacct       120
ggccaggcac ccaggctcct catctacggg gcatccaacc gggccactgg catcccagcc       180
aggttcagtg gcagtgggtc tgggacagac ttcactctca ccatcagcag actggagcct       240
gaagattttg cagtgtacta ctgcggccag agctatagct atccatttac ctttggccag       300
ggcaccaagc ttgaaattaa gcgtacggtg gccgctccca gcgtgttcat cttcccccc        360 agcgacgagc agctgaagag cggcaccgcc agcgtggtgt gcctgctgaa caacttctac       420
ccccgggagg ccaaggtgca gtggaaggtg gacaacgccc tgcagagcgg caacagccag       480
gagagcgtca ccgagcagga cagcaaggac tccacctaca gcctgagcag caccctgacc       540
ctgagcaagg ccgactacga aagcataag gtgtacgcct gcgaggtgac ccaccagggc        600
ctgtccagcc ccgtgaccaa gagcttcaac agggcgagt gc                           642
```

<210> SEQ ID NO 69
<211> LENGTH: 451
<212> TYPE: PRT
<213> ORGANISM: Artificial Sequence
<220> FEATURE:
<223> OTHER INFORMATION: synthetic sequence

<400> SEQUENCE: 69

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Leu
        35                  40                  45

Gly Val Ile Trp Gly Gly Gly Thr Tyr Tyr Thr Ala Ser Leu Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Ala Tyr Gly His Asp Gly Gly Phe Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 70
<211> LENGTH: 214
<212> TYPE: PRT
<213> ORGANISM: Artificial Sequence
<220> FEATURE:
<223> OTHER INFORMATION: synthetic sequence

<400> SEQUENCE: 70

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Asn Arg Ala Thr Gly Ile Pro Asp Arg Phe Ser Gly
    50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys Gly Gln Ser Tyr Ser Tyr Pro Phe
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 1353
<212> TYPE: DNA
<213> ORGANISM: Artificial Sequence
<220> FEATURE:
<223> OTHER INFORMATION: synthetic sequence

<400> SEQUENCE: 71
caggtgcagc tggtggagtc tgggggaggc ttggtacagc ctgggggtc cctgagactc      60 tcctgtgcag cctctggatt ctccctcagc agctatggtg tggactgggt tcgccaggct     120
ccaggaaagg gtctggagtg gctgggagtt atatggggtg gtggaggcac atattatact     180
gcttctctca tgggcagatt caccatctcc agagacaatt ccaagaacac gctgtatctg     240
caaatgaaca gcctgagagc tgaggacacg gccgtgtatt actgcgccaa acatgcctat     300
ggccatgatg gcggctttgc tatggattat tggggccagg gtaccttgt gaccgtgagc      360 tcagctagca ccaagggccc cagcgtgttc cccctggccc cagcagcaa gagcaccagc      420 ggcggcacag ccgccctggg ctgcctggtg aaggactact cccccgagcc cgtgaccgtg     480
tcctggaaca gcggagccct gacctccggc gtgcacacct tccccgccgt gctgcagagc     540
agcggcctgt acagcctgtc cagcgtggtg acagtgccca gcagcagcct gggcacccag     600
acctacatct gcaacgtgaa ccacaagccc agcaacacca aggtggacaa gagagtggag     660
cccaagagct gcgacaagac ccacacctgc cccccctgcc cagccccaga gctgctgggc     720
ggaccctccg tgttcctgtt ccccccaag cccaaggaca ccctgatgat cagcaggacc      780
cccgaggtga cctgcgtggt ggtggacgtg agccacgagg acccagaggt gaagttcaac     840
tggtacgtgg acggcgtgga ggtgcacaac gccaagacca gcccagaga ggagcagtac     900 aacagcacct cagggtggt gtccgtgctg accgtgctgc accaggactg gctgaacggc      960
aaggaataca agtgcaaggt ctccaacaag gccctgccag cccccatcga aagaccatc     1020 agcaaggcca agggccagcc acgggagccc caggtgtaca ccctgccccc ctcccgggag    1080
gagatgacca gaaccaggt gtccctgacc tgtctggtga agggcttcta ccccagcgac     1140
atcgccgtgg agtgggagag caacggccag cccgagaaca actacaagac cacccccca     1200 gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagcct gtccccggc aag                                  1353

<210> SEQ ID NO 72
<211> LENGTH: 642
<212> TYPE: DNA
<213> ORGANISM: Artificial Sequence
<220> FEATURE:
<223> OTHER INFORMATION: synthetic sequence

<400> SEQUENCE: 72

```
gaaatagtga tgacgcagtc tccagccacc ctgtctgtgt ctccagggga agagccacc    60
ctctcctgca gggccagtca gagtgttagc agcaacttag cctggtacca gcagaaacct  120
ggccaggctc ccaggctcct catctacggg gcatccaacc gggccactgg catcccagac  180
aggttcagtg gcagtgggtc tgggacagac ttcactctca ccatcagcag actggagcct  240
gaagattttg cagtttacta ctgcggccag agctatagct atccatttac ctttggccag  300
ggcaccaagc ttgaaattaa acgtacggtg gccgctccca gcgtgttcat cttcccccc   360
agcgacgagc agctgaagag cggcaccgcc agcgtggtgt gcctgctgaa caacttctac  420
ccccgggagg ccaaggtgca gtggaaggtg acaacgccc tgcagagcgg caacagccag   480
gagagcgtca ccgagcagga cagcaaggac tccacctaca gcctgagcag caccctgacc  540
ctgagcaagg ccgactacga aagcataag gtgtacgcct gcgaggtgac ccaccagggc  600
ctgtccagcc ccgtgaccaa gagcttcaac aggggcgagt gc                     642
```

<210> SEQ ID NO 73
<211> LENGTH: 451
<212> TYPE: PRT
<213> ORGANISM: Artificial Sequence
<220> FEATURE:
<223> OTHER INFORMATION: synthetic sequence

<400> SEQUENCE: 73

```
Glu Val Gln Leu Val Glu Ser Gly Gly Gly Leu Val Gln Ser Gly Gly
1               5                   10                  15
Ser Leu Arg Leu Ser Cys Ala Ala Ser Gly Phe Ser Leu Ser Ser Tyr
            20                  25                  30
Gly Val Asp Trp Val Arg Gln Ala Pro Gly Lys Gly Leu Glu Trp Val
        35                  40                  45
Gly Val Ile Trp Gly Gly Gly Thr Tyr Tyr Ala Ser Ser Leu Met
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Lys His Ala Tyr Gly His Asp Gly Gly Phe Ala Met Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 74
<211> LENGTH: 1353
<212> TYPE: DNA
<213> ORGANISM: Artificial Sequence
<220> FEATURE:
<223> OTHER INFORMATION: synthetic sequence

<400> SEQUENCE: 74
gaggtgcagc tggtggagtc cggggggaggc ttagttcagt ctggggggtc cctgagactc      60
tcctgtgcag cctctggatt ctccctcagc agctatggtg tggactgggt tcgccaggct     120
ccaggaaagg gtctggagtg ggtgggagtt atatgggggtg gtggaggcac atattatgct     180
tcttctctca tgggcagatt caccatctcc agagacaatt ccaagaacac gctgtatctg     240
caaatgaaca gcctgagagc tgaggacacg gccgtgtatt actgcgccaa acatgcctat     300
ggccatgatg gcggctttgc tatggattat tgggggccagg gtacccttgt gaccgtgagc     360
tcagctagca ccaagggccc cagcgtgttc ccctggccc ccagcagcaa gagcaccagc      420
ggcggcacag ccgccctggg ctgcctggtg aaggactact ccccgagcc cgtgaccgtg      480
tcctggaaca gcggagccct gacctccggc gtgcacacct ccccgccgt gctgcagagc      540
agcggcctgt acagcctgtc cagcgtggtg acagtgccca gcagcagcct gggcacccag     600
acctacatct gcaacgtgaa ccacaagccc agcaacacca aggtggacaa gagagtggag     660
cccaagagct gcgacaagac ccacacctgc ccccccctgcc cagccccaga gctgctgggc     720
ggaccctccg tgttcctgtt ccccccccaag cccaaggaca ccctgatgat cagcaggacc     780
cccgaggtga cctgcgtggt ggtggacgtg agccacgagg acccagaggt gaagttcaac     840
tggtacgtgg acggcgtgga ggtgcacaac gccaagacca gcccagaga ggagcagtac      900
```

```
aacagcacct acagggtggt gtccgtgctg accgtgctgc accaggactg gctgaacggc   960
aaggaataca agtgcaaggt ctccaacaag gccctgccag cccccatcga aaagaccatc  1020
agcaaggcca agggccagcc acgggagccc caggtgtaca ccctgccccc ctcccgggag  1080
gagatgacca agaaccaggt gtccctgacc tgtctggtga agggcttcta ccccagcgac  1140
atcgccgtgg agtgggagag caacggccag cccgagaaca actacaagac acccccccca  1200
gtgctggaca cgacggcag cttcttcctg tacagcaagc tgaccgtgga caagtccagg  1260
tggcagcagg gcaacgtgtt cagctgcagc gtgatgcacg aggccctgca caaccactac  1320
acccagaaga gcctgagcct gtcccccggc aag                               1353

<210> SEQ ID NO 75
<211> LENGTH: 451
<212> TYPE: PRT
<213> ORGANISM: Artificial Sequence
<220> FEATURE:
<223> OTHER INFORMATION: synthetic sequence

<400> SEQUENCE: 75

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Leu
        35                  40                  45

Gly Val Ile Trp Gly Gly Gly Thr Tyr Tyr Thr Ser Ser Leu Met
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
            85                  90                  95

Lys His Ala Tyr Gly His Asp Gly Gly Phe Ala Met Asp Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

|     |     |     |     | 275 |     |     |     |     | 280 |     |     |     |     | 285 |     |
| --- | --- | --- | --- | --- | --- | --- | --- | --- | --- | --- | --- | --- | --- | --- | --- |
| His | Asn | Ala | Lys | Thr | Lys | Pro | Arg | Glu | Glu | Gln | Tyr | Asn | Ser | Thr | Tyr |
|     |     |     |     | 290 |     |     |     |     | 295 |     |     |     |     | 300 |     |
| Arg | Val | Val | Ser | Val | Leu | Thr | Val | Leu | His | Gln | Asp | Trp | Leu | Asn | Gly |
| 305 |     |     |     |     | 310 |     |     |     |     | 315 |     |     |     |     | 320 |
| Lys | Glu | Tyr | Lys | Cys | Lys | Val | Ser | Asn | Lys | Ala | Leu | Pro | Ala | Pro | Ile |
|     |     |     |     | 325 |     |     |     |     | 330 |     |     |     |     | 335 |     |
| Glu | Lys | Thr | Ile | Ser | Lys | Ala | Lys | Gly | Gln | Pro | Arg | Glu | Pro | Gln | Val |
|     |     |     | 340 |     |     |     |     | 345 |     |     |     |     | 350 |     |     |
| Tyr | Thr | Leu | Pro | Pro | Ser | Arg | Glu | Glu | Met | Thr | Lys | Asn | Gln | Val | Ser |
|     |     | 355 |     |     |     |     | 360 |     |     |     |     | 365 |     |     |     |
| Leu | Thr | Cys | Leu | Val | Lys | Gly | Phe | Tyr | Pro | Ser | Asp | Ile | Ala | Val | Glu |
|     | 370 |     |     |     |     | 375 |     |     |     |     | 380 |     |     |     |     |
| Trp | Glu | Ser | Asn | Gly | Gln | Pro | Glu | Asn | Asn | Tyr | Lys | Thr | Thr | Pro | Pro |
| 385 |     |     |     |     | 390 |     |     |     |     | 395 |     |     |     |     | 400 |
| Val | Leu | Asp | Ser | Asp | Gly | Ser | Phe | Phe | Leu | Tyr | Ser | Lys | Leu | Thr | Val |
|     |     |     |     | 405 |     |     |     |     | 410 |     |     |     |     | 415 |     |
| Asp | Lys | Ser | Arg | Trp | Gln | Gln | Gly | Asn | Val | Phe | Ser | Cys | Ser | Val | Met |
|     |     |     | 420 |     |     |     |     | 425 |     |     |     |     | 430 |     |     |
| His | Glu | Ala | Leu | His | Asn | His | Tyr | Thr | Gln | Lys | Ser | Leu | Ser | Leu | Ser |
|     |     | 435 |     |     |     |     | 440 |     |     |     |     | 445 |     |     |     |
| Pro | Gly | Lys |     |     |     |     |     |     |     |     |     |     |     |     |     |
|     | 450 |     |     |     |     |     |     |     |     |     |     |     |     |     |     |

<210> SEQ ID NO 76
<211> LENGTH: 1353
<212> TYPE: DNA
<213> ORGANISM: Artificial Sequence
<220> FEATURE:
<223> OTHER INFORMATION: synthetic sequence

<400> SEQUENCE: 76

```
gaggtgcagc tggtggagtc cggggggaggc ttagttcagt ctggggggtc cctgagactc      60
tcctgtgcag cctctggatt ctccctcagc agctatggtg tggactgggt tcgccaggct     120
ccaggaaagg gtctggagtg gctgggagtt atatgggggt gtggaggcac atattatact     180
tcttctctca tgggcagatt caccatctcc agagacaatt ccaagaacac gctgtatctg     240
caaatgaaca gcctgagagc tgaggacacg gccgtgtatt actgcgccaa acatgcctat     300
ggccatgatg cggctttgc tatggattat tggggccagg gtaccctgt gaccgtgagc      360
tcagctagca ccaagggccc cagcgtgttc cccctggccc cagcagcaa gagcaccagc     420
ggcggcacag ccgccctggg ctgcctggtg aaggactact ccccgagcc cgtgaccgtg     480
tcctggaaca gcggagccct gacctccggc gtgcacacct tcccgccgt gctgcagagc     540
agcggcctgt acagcctgtc cagcgtggtg acagtgccca gcagcagcct gggcacccag     600
acctacatct gcaacgtgaa ccacaagccc agcaacacca aggtggacaa gagagtggag     660
cccaagagct gcgacaagac ccacacctgc ccccctgcc cagccccaga gctgctgggc     720
ggaccctccg tgttcctgtt cccccccaag cccaaggaca ccctgatgat cagcaggacc     780
cccgaggtga cctgcgtggt ggtggacgtg agccacgagg acccagaggt gaagttcaac     840
tggtacgtgg acggcgtgga ggtgcacaac gccaagacca gcccagaga ggagcagtac     900
aacagcacct acagggtggt gtccgtgctg accgtgctgc accaggactg gctgaacggc     960
aaggaataca agtgcaaggt ctccaacaag gccctgccag cccccatcga aaagaccatc    1020
```

```
agcaaggcca agggccagcc acgggagccc caggtgtaca ccctgccccc ctcccgggag    1080
gagatgacca agaaccaggt gtccctgacc tgtctggtga agggcttcta ccccagcgac    1140
atcgccgtgg agtgggagag caacggccag cccgagaaca actacaagac cacccccca     1200 gtgctggaca cgacggcag cttcttcctg tacagcaagc tgaccgtgga caagtccagg     1260
tggcagcagg gcaacgtgtt cagctgcagc gtgatgcacg aggccctgca caaccactac    1320
acccagaaga gcctgagcct gtcccccggc aag                                 1353
```

<210> SEQ ID NO 77
<211> LENGTH: 451
<212> TYPE: PRT
<213> ORGANISM: Artificial Sequence
<220> FEATURE:
<223> OTHER INFORMATION: synthetic sequence

<400> SEQUENCE: 77

```
Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Leu
        35                  40                  45

Gly Val Ile Trp Gly Gly Gly Thr Tyr Tyr Thr Ser Ser Leu Met
    50                  55                  60

Ala Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Ala Tyr Gly His Asp Gly Gly Phe Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 78
<211> LENGTH: 1353
<212> TYPE: DNA
<213> ORGANISM: Artificial Sequence
<220> FEATURE:
<223> OTHER INFORMATION: synthetic sequence

<400> SEQUENCE: 78
gaggtgcagc tggtggagtc cggggggaggc ttagttcagt ctgggggtc cctgagactc      60 tcctgtgcag cctctggatt ctccctcagc agctatggtg tggactgggt tcgccaggct     120
ccaggaaagg gtctggagtg gctgggagtt atatggggtg gtgaggcac atattatact     180 tcttctctca tggccagatt caccatctcc agagacaatt ccaagaacac gctgtatctg     240
caaatgaaca gcctgagagc tgaggacacg gccgtgtatt actgcgccaa acatgcctat     300
ggccatgatg gcggctttgc tatggattat tggggccagg gtacccttgt gaccgtgagc     360
tcagctagca ccaagggccc cagcgtgttc cccctggccc cagcagcaa gagcaccagc     420 ggcggcacag ccgccctggg ctgcctggtg aaggactact ccccgagcc cgtgaccgtg     480 tcctggaaca gcggagccct gacctccggc gtgcacacct ccccgccgt gctgcagagc     540 agcggcctgt acagcctgtc cagcgtggtg acagtgccca gcagcagcct gggcacccag     600
acctacatct gcaacgtgaa ccacaagccc agcaacacca aggtggacaa gagagtggag     660
cccaagagct gcgacaagac ccacacctgc ccccctgcc cagccccaga gctgctgggc     720
ggacccctcg tgttcctgtt cccccccaag cccaaggaca ccctgatgat cagcaggacc     780
cccgaggtga cctgcgtggt ggtggacgtg agccacgagg acccagaggt gaagttcaac     840
tggtacgtgg acggcgtgga ggtgcacaac gccaagacca gcccagaga ggagcagtac     900 aacagcacct acagggtggt gtccgtgctg accgtgctgc accaggactg gctgaacggc     960
aaggaataca agtgcaaggt ctccaacaag gccctgccag ccccatcga aaagaccatc    1020 agcaaggcca agggcagcc acgggagccc caggtgtaca cctgccccc ctcccgggag    1080 gagatgacca gaaccaggt gtccctgacc tgtctggtga agggcttcta ccccagcgac    1140
atcgccgtgg agtgggagag caacggccag cccgagaaca actacaagac caccccccca    1200
```

```
gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaaga gcctgagcct gtccccggc aag                                  1353
```

```
<210> SEQ ID NO 79
<211> LENGTH: 7
<212> TYPE: PRT
<213> ORGANISM: Artificial Sequence
<220> FEATURE:
<223> OTHER INFORMATION: synthetic sequence

<400> SEQUENCE: 79

Gly Phe Ser Leu Arg Ser Tyr
1               5

<210> SEQ ID NO 80
<211> LENGTH: 5
<212> TYPE: PRT
<213> ORGANISM: Artificial Sequence
<220> FEATURE:
<223> OTHER INFORMATION: synthetic sequence

<400> SEQUENCE: 80

Trp Gly Gly Gly Gly
1               5

<210> SEQ ID NO 81
<211> LENGTH: 7
<212> TYPE: PRT
<213> ORGANISM: Artificial Sequence
<220> FEATURE:
<223> OTHER INFORMATION: synthetic sequence

<400> SEQUENCE: 81

Ser Glu Asn Val Asp Thr Phe
1               5

<210> SEQ ID NO 82
<211> LENGTH: 3
<212> TYPE: PRT
<213> ORGANISM: Artificial Sequence
<220> FEATURE:
<223> OTHER INFORMATION: synthetic sequence

<400> SEQUENCE: 82

Gly Ala Ser
1

<210> SEQ ID NO 83
<211> LENGTH: 6
<212> TYPE: PRT
<213> ORGANISM: Artificial Sequence
<220> FEATURE:
<223> OTHER INFORMATION: synthetic sequence

<400> SEQUENCE: 83

Ser Tyr Ser Tyr Pro Phe
1               5

<210> SEQ ID NO 84
<211> LENGTH: 7
<212> TYPE: PRT
<213> ORGANISM: Artificial Sequence
<220> FEATURE:
<223> OTHER INFORMATION: synthetic sequence
```

<400> SEQUENCE: 84

Gly Phe Ser Leu Ser Ser Tyr
1               5

<210> SEQ ID NO 85
<211> LENGTH: 7
<212> TYPE: PRT
<213> ORGANISM: Artificial Sequence
<220> FEATURE:
<223> OTHER INFORMATION: synthetic sequence

<400> SEQUENCE: 85

Ser Glu Ser Val Ser Ser Asn
1               5

<210> SEQ ID NO 86
<211> LENGTH: 7
<212> TYPE: PRT
<213> ORGANISM: Artificial Sequence
<220> FEATURE:
<223> OTHER INFORMATION: synthetic sequence

<400> SEQUENCE: 86

Ser Gln Ser Val Ser Ser Asn
1               5

<210> SEQ ID NO 87
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (2)..(2)
<223> OTHER INFORMATION: (E/Q)

<400> SEQUENCE: 87

Ser Xaa Ser Val Ser Ser Asn
1               5

<210> SEQ ID NO 88
<211> LENGTH: 56
<212> TYPE: PRT
<213> ORGANISM: Artificial Sequence
<220> FEATURE:
<223> OTHER INFORMATION: synthetic sequence

<400> SEQUENCE: 88

Arg Pro Thr Gly Gly Pro Gly Cys Gly Pro Gly Arg Leu Leu Gly Thr
1               5                   10                  15
Gly Thr Asp Ala Arg Cys Cys Arg Val His Thr Thr Arg Cys Cys Arg
                20                  25                  30
Asp Tyr Pro Gly Glu Glu Cys Cys Ser Glu Trp Asp Cys Met Cys Val
            35                  40                  45
Gln Pro Glu Phe His Cys Gly Asp
    50                  55

<210> SEQ ID NO 89
<211> LENGTH: 98
<212> TYPE: PRT
<213> ORGANISM: Artificial Sequence
<220> FEATURE:
<223> OTHER INFORMATION: synthetic sequence -continued

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Arg Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 90
<211> LENGTH: 11
<212> TYPE: PRT
<213> ORGANISM: Artificial Sequence
<220> FEATURE:
<223> OTHER INFORMATION: synthetic sequence

<400> SEQUENCE: 90

Trp Gly Gln Gly Thr Leu Val Thr Val Ser Ser
1               5                   10

<210> SEQ ID NO 91
<211> LENGTH: 15
<212> TYPE: PRT
<213> ORGANISM: Artificial Sequence
<220> FEATURE:
<223> OTHER INFORMATION: synthetic sequence

<400> SEQUENCE: 91

Tyr Phe Asp Tyr Trp Gly Gln Gly Thr Leu Val Thr Val Ser Ser
1               5                   10                  15

<210> SEQ ID NO 92
<211> LENGTH: 95
<212> TYPE: PRT
<213> ORGANISM: Artificial Sequence
<220> FEATURE:
<223> OTHER INFORMATION: synthetic sequence

<400> SEQUENCE: 92

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro
                85                  90                  95

<210> SEQ ID NO 93
<211> LENGTH: 10

```
<212> TYPE: PRT
<213> ORGANISM: Artificial Sequence
<220> FEATURE:
<223> OTHER INFORMATION: synthetic sequence

<400> SEQUENCE: 93

Phe Gly Gln Gly Thr Lys Leu Glu Ile Lys
1               5                   10

<210> SEQ ID NO 94
<211> LENGTH: 12
<212> TYPE: PRT
<213> ORGANISM: Artificial Sequence
<220> FEATURE:
<223> OTHER INFORMATION: synthetic sequence

<400> SEQUENCE: 94

Tyr Thr Phe Gly Gln Gly Thr Lys Leu Glu Ile Lys
1               5                   10

<210> SEQ ID NO 95
<211> LENGTH: 37
<212> TYPE: DNA
<213> ORGANISM: Artificial Sequence
<220> FEATURE:
<223> OTHER INFORMATION: synthetic sequence

<400> SEQUENCE: 95
gggtctagac accatggctg tcttggggct gctcttc                           37

<210> SEQ ID NO 96
<211> LENGTH: 39
<212> TYPE: DNA
<213> ORGANISM: Artificial Sequence
<220> FEATURE:
<223> OTHER INFORMATION: synthetic sequence

<400> SEQUENCE: 96
gcgtctagaa yctccacaca caggrrccag tggatagac                         39

<210> SEQ ID NO 97
<211> LENGTH: 40
<212> TYPE: DNA
<213> ORGANISM: Artificial Sequence
<220> FEATURE:
<223> OTHER INFORMATION: synthetic sequence

<400> SEQUENCE: 97
gggtctagac accatggagw cacakwctca ggtctttrta                        40

<210> SEQ ID NO 98
<211> LENGTH: 88
<212> TYPE: PRT
<213> ORGANISM: Artificial Sequence
<220> FEATURE:
<223> OTHER INFORMATION: synthetic sequence

<400> SEQUENCE: 98

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
```

```
                   50                  55                  60
Ser Gly Ser Gly Thr Asp Phe Thr Leu Thr Ile Ser Arg Leu Glu Pro
 65                  70                  75                  80

Glu Asp Phe Ala Val Tyr Tyr Cys
                 85

<210> SEQ ID NO 99
<211> LENGTH: 121
<212> TYPE: PRT
<213> ORGANISM: Artificial Sequence
<220> FEATURE:
<223> OTHER INFORMATION: synthetic sequence

<400> SEQUENCE: 99

Glu Val Gln Leu Val Glu Ser Gly Gly Gly Leu Val Gln Ser Gly Gly
  1               5                  10                  15

Ser Leu Arg Leu Ser Cys Ala Ala Ser Gly Phe Ser Leu Ser Ser Tyr
                 20                  25                  30

Gly Val Asp Trp Val Arg Gln Ala Pro Gly Lys Gly Leu Glu Trp Val
             35                  40                  45

Gly Val Ile Trp Gly Gly Gly Thr Tyr Tyr Ala Ser Ser Leu Met
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg His Ala Tyr Gly His Asp Gly Gly Phe Ala Met Asp Tyr Trp Gly
            100                 105                 110

Gln Gly Thr Leu Val Thr Val Ser Ser
        115                 120

<210> SEQ ID NO 100
<211> LENGTH: 451
<212> TYPE: PRT
<213> ORGANISM: Artificial Sequence
<220> FEATURE:
<223> OTHER INFORMATION: synthetic sequence

<400> SEQUENCE: 100

Glu Val Gln Leu Val Glu Ser Gly Gly Gly Leu Val Gln Ser Gly Gly
  1               5                  10                  15

Ser Leu Arg Leu Ser Cys Ala Ala Ser Gly Phe Ser Leu Ser Ser Tyr
                 20                  25                  30

Gly Val Asp Trp Val Arg Gln Ala Pro Gly Lys Gly Leu Glu Trp Val
             35                  40                  45

Gly Val Ile Trp Gly Gly Gly Thr Tyr Tyr Ala Ser Ser Leu Met
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg His Ala Tyr Gly His Asp Gly Gly Phe Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 101
<211> LENGTH: 363
<212> TYPE: DNA
<213> ORGANISM: Artificial Sequence
<220> FEATURE:
<223> OTHER INFORMATION: synthetic sequence

<400> SEQUENCE: 101
gaggtgcagc tggtggaatc tggcggcgga ctggtgcagt ccggcggctc tctgagactg      60
tcttgcgctg cctccggctt ctccctgtcc tcttacggcg tggactgggt gcgacaggcc     120
cctggcaagg gcctggaatg ggtgggagtg atctggggcg aggcggcac ctactacgcc      180 tcttccctga tgggccggtt caccatctcc cgggacaact ccaagaacac cctgtacctg     240
cagatgaact ccctgcgggc cgaggacacc gccgtgtact actgcgccag acacgcctac     300
```

```
ggccacgacg gcggcttcgc catggattat tggggccagg gcaccctggt gacagtgtcc    360
tcc                                                                 363

<210> SEQ ID NO 102
<211> LENGTH: 321
<212> TYPE: DNA
<213> ORGANISM: Artificial Sequence
<220> FEATURE:
<223> OTHER INFORMATION: synthetic sequence

<400> SEQUENCE: 102
gagatcgtga tgacccagtc ccccgccacc ctgtctgtgt ctcccggcga gagagccacc     60
ctgagctgca gagcctccga gtccgtgtcc tccaacgtgg cctggtatca gcagagacct    120
ggtcaggccc ctcggctgct gatctacggc gcctctaacc gggccaccgg catccctgcc    180
agattctccg gctccggcag cggcaccgac ttcaccctga ccatctcccg gctggaaccc    240
gaggacttcg ccgtgtacta ctgcggccag tcctactcat accccttcac cttcggccag    300
ggcaccaagc tggaaatcaa g                                              321

<210> SEQ ID NO 103
<211> LENGTH: 1353
<212> TYPE: DNA
<213> ORGANISM: Artificial Sequence
<220> FEATURE:
<223> OTHER INFORMATION: synthetic sequence

<400> SEQUENCE: 103
gaggtgcagc tggtggaatc tggcggcgga ctggtgcagt ccggcggctc tctgagactg     60
tcttgcgctg cctccggctt ctccctgtcc tcttacggcg tggactgggt gcgacaggcc    120
cctggcaagg gcctggaatg ggtgggagtg atctggggcg aggcggcac ctactacgcc    180 tcttccctga tgggccggtt caccatctcc cgggacaact ccaagaacac cctgtacctg    240
cagatgaact ccctgcgggc cgaggacacc gccgtgtact actgcgccag acacgcctac    300
ggccacgacg gcggcttcgc catggattat tggggccagg gcaccctggt gacagtgtcc    360
tccgctagca ccaagggccc aagtgtgttt cccctggccc ccagcagcaa gtctacttcc    420
ggcggaactg ctgccctggg ttgcctggtg aaggactact cccccgagcc cgtgacagtg    480
tcctggaact ctggggctct gacttccggc gtgcacacct tccccgccgt gctgcagagc    540
agcggcctgt acagcctgag cagcgtggtg acagtgccct ccagctctct gggaacccag    600
acctatatct gcaacgtgaa ccacaagccc agcaacacca aggtggacaa gagagtggag    660
cccaagagct gcgacaagac ccacacctgc cccccctgcc cagctccaga actgctggga    720
gggccttccg tgttcctgtt cccccccaag cccaaggaca ccctgatgat cagcaggacc    780
cccgaggtga cctgcgtggt ggtggacgtg tcccacgagg acccagaggt gaagttcaac    840
tggtacgtgg acggcgtgga ggtgcacaac gccaagacca gcccagaga ggagcagtac    900 aacagcacct acagggtggt gtccgtgctg accgtgctgc accaggactg gctgaacggc    960
aaagaataca agtgcaaagt ctccaacaag gccctgccag cccccatcga aaagacaatc   1020
agcaaggcca agggccagcc acgggagccc caggtgtaca ccctgccccc cagccggag   1080 gagatgacca agaaccaggt gtccctgacc tgtctggtga agggcttcta ccccagcgat   1140
atcgccgtgg agtgggagag caacggccag ccgagaaca actacaagac cacccccca   1200 gtgctggaca gcgacggcag cttcttcctg tacagcaagc tgaccgtgga caagtccagg   1260
```

```
tggcagcagg gcaacgtgtt cagctgcagc gtgatgcacg aggccctgca caaccactac   1320
acccagaagt ccctgagcct gagccccggc aag                                1353

<210> SEQ ID NO 104
<211> LENGTH: 642
<212> TYPE: DNA
<213> ORGANISM: Artificial Sequence
<220> FEATURE:
<223> OTHER INFORMATION: synthetic sequence

<400> SEQUENCE: 104
gagatcgtga tgacccagtc ccccgccacc ctgtctgtgt ctcccggcga gagagccacc     60
ctgagctgca gagcctccga gtccgtgtcc tccaacgtgg cctggtatca gcagagacct    120
ggtcaggccc ctcggctgct gatctacggc gcctctaacc gggccaccgg catccctgcc    180
agattctccg gctccggcag cggcaccgac ttcaccctga ccatctcccg gctggaaccc    240
gaggacttcg ccgtgtacta ctgcggccag tcctactcat accccttcac cttcggccag    300
ggcaccaagc tggaaatcaa gcgtacggtg gccgctccca gcgtgttcat cttccccccc    360
agcgacgagc agctgaagag cggcaccgcc agcgtggtgt gcctgctgaa caacttctac    420
ccccgggagg ccaaggtgca gtggaaggtg gacaacgccc tgcagagcgg caacagccag    480
gagagcgtca ccgagcagga cagcaaggac tccacctaca gcctgagcag caccctgacc    540
ctgagcaagg ccgactacga gaagcataag gtgtacgcct gcgaggtgac ccaccagggc    600
ctgtccagcc ccgtgaccaa gagcttcaac aggggcgagt gc                       642

<210> SEQ ID NO 105
<211> LENGTH: 121
<212> TYPE: PRT
<213> ORGANISM: Artificial Sequence
<220> FEATURE:
<223> OTHER INFORMATION: synthetic sequence

<400> SEQUENCE: 105

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Ser Leu Ser Ser Tyr
            20                  25                  30

Gly Val Asp Trp Val Arg Gln Ala Pro Gly Lys Gly Leu Glu Trp Val
        35                  40                  45

Gly Val Ile Trp Gly Gly Gly Thr Tyr Tyr Ala Ser Ser Leu Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Ala Tyr Gly His Asp Gly Gly Phe Ala Met Asp Tyr Trp Gly
            100                 105                 110

Gln Gly Thr Leu Val Thr Val Ser Ser
        115                 120

<210> SEQ ID NO 106
<211> LENGTH: 451
<212> TYPE: PRT
<213> ORGANISM: Artificial Sequence
<220> FEATURE:
<223> OTHER INFORMATION: synthetic sequence

<400> SEQUENCE: 106
```

-continued

```
Glu Val Gln Leu Val Glu Ser Gly Gly Gly Leu Val Gln Ser Gly Gly
 1               5                  10                  15
Ser Leu Arg Leu Ser Cys Ala Ala Ser Gly Phe Ser Leu Ser Ser Tyr
            20                  25                  30
Gly Val Asp Trp Val Arg Gln Ala Pro Gly Lys Gly Leu Glu Trp Val
        35                  40                  45
Gly Val Ile Trp Gly Gly Gly Thr Tyr Tyr Ala Ser Ser Leu Met
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
            85                  90                  95
Arg Asn Ala Tyr Gly His Asp Gly Gly Phe Ala Met Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
```

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 107
<211> LENGTH: 363
<212> TYPE: DNA
<213> ORGANISM: Artificial Sequence
<220> FEATURE:
<223> OTHER INFORMATION: synthetic sequence

<400> SEQUENCE: 107
gaggtgcagc tggtggaatc aggcggcgga ctggtgcagt caggcggtag cctgagactg      60
agctgcgccg cctccggctt tagcctgtct agctacggcg tggactgggt ccgacaggcc     120
cctggcaaag gcctggagtg ggtcggagtg atctggggcg gaggcggaac ctactacgcc     180
tctagcctga tgggccggtt cactatctct agggacaact ctaagaacac cctgtacctg     240
cagatgaact cactgagagc cgaggacacc gccgtctact actgcgctag aaacgcctac     300
ggtcacgacg gcggcttcgc tatggactac tggggtcagg gcaccctggt caccgtgagt     360
tca                                                                   363

<210> SEQ ID NO 108
<211> LENGTH: 1353
<212> TYPE: DNA
<213> ORGANISM: Artificial Sequence
<220> FEATURE:
<223> OTHER INFORMATION: synthetic sequence

<400> SEQUENCE: 108
gaggtgcagc tggtggaatc aggcggcgga ctggtgcagt caggcggtag cctgagactg      60
agctgcgccg cctccggctt tagcctgtct agctacggcg tggactgggt ccgacaggcc     120
cctggcaaag gcctggagtg ggtcggagtg atctggggcg gaggcggaac ctactacgcc     180
tctagcctga tgggccggtt cactatctct agggacaact ctaagaacac cctgtacctg     240
cagatgaact cactgagagc cgaggacacc gccgtctact actgcgctag aaacgcctac     300
ggtcacgacg gcggcttcgc tatggactac tggggtcagg gcaccctggt caccgtgagt     360
tcagctagca ctaagggccc aagtgtgttt cccctggccc cagcagcaa gtctacttcc     420 ggcggaactg ctgccctggg ttgcctggtg aaggactact cccccgagcc cgtgacagtg     480
tcctggaact ctggggctct gacttccggc gtgcacacct ccccgccgt gctgcagagc     540 agcggcctgt acagcctgag cagcgtggtg acagtgccct ccagctctct gggaacccag     600
acctatatct gcaacgtgaa ccacaagccc agcaacacca aggtggacaa gagagtggag     660
cccaagagct gcgacaagac ccacacctgc cccccctgcc cagctccaga actgctggga     720
gggccttccg tgttcctgtt cccccccaag cccaaggaca cctgatgat cagcaggacc     780 cccgaggtga cctgcgtggt ggtggacgtg tcccacgagg acccagaggt gaagttcaac     840
tggtacgtgg acggcgtgga ggtgcacaac gccaagacca gcccagaga ggagcagtac     900 aacagcacct acagggtggt gtccgtgctg accgtgctgc accaggactg gctgaacggc     960
aaagaataca agtgcaaagt ctccaacaag gccctgccag ccccaatcga aaagacaatc    1020
agcaaggcca aggccagcc acgggagccc caggtgtaca ccctgccccc cagccgggag    1080

```
gagatgacca agaaccaggt gtccctgacc tgtctggtga agggcttcta ccccagcgat    1140
atcgccgtgg agtgggagag caacggccag cccgagaaca actacaagac cacccccca     1200 gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaagt ccctgagcct gagccccggc aag                                 1353
```

```
<210> SEQ ID NO 109
<211> LENGTH: 13
<212> TYPE: PRT
<213> ORGANISM: Artificial Sequence
<220> FEATURE:
<223> OTHER INFORMATION: synthetic sequence

<400> SEQUENCE: 109

Asn Ala Tyr Gly His Asp Gly Gly Phe Ala Met Asp Tyr
1               5                   10
```

```
<210> SEQ ID NO 110
<211> LENGTH: 22
<212> TYPE: DNA
<213> ORGANISM: Artificial Sequence
<220> FEATURE:
<223> OTHER INFORMATION: synthetic sequence

<400> SEQUENCE: 110
tctggcgcag taatacacgg cc                                              22
```

```
<210> SEQ ID NO 111
<211> LENGTH: 22
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(3)
<223> OTHER INFORMATION: degenerate trinucleotide codon sequence nnk

<400> SEQUENCE: 111
nnkgcctatg gccatgatgg cg                                              22
```

```
<210> SEQ ID NO 112
<211> LENGTH: 17
<212> TYPE: DNA
<213> ORGANISM: Artificial Sequence
<220> FEATURE:
<223> OTHER INFORMATION: synthetic sequence

<400> SEQUENCE: 112
gcctttctct ccacagg                                                    17
```

```
<210> SEQ ID NO 113
<211> LENGTH: 20
<212> TYPE: DNA
<213> ORGANISM: Artificial Sequence
<220> FEATURE:
<223> OTHER INFORMATION: synthetic sequence

<400> SEQUENCE: 113
ggcaaacaac agatggctgg                                                 20
```